US 9,964,968 B2

(12) United States Patent
Sharpe et al.

(10) Patent No.: US 9,964,968 B2
(45) Date of Patent: May 8, 2018

(54) OPERATORLESS PARTICLE PROCESSING SYSTEMS AND METHODS

(71) Applicant: CYTONOME/ST, LLC, Boston, MA (US)

(72) Inventors: Johnathan Charles Sharpe, Hamilton (NZ); Nemanya Sedoglavich, Dorchester, MA (US); Vladimir Shapiro, Newton, MA (US); Stuart R. Ehrlich, Boston, MA (US); Donald Francis Perrault, Jr., Brighton, MA (US); Blair D. Morad, Ipswich, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 404 days.

(21) Appl. No.: 14/210,381

(22) Filed: Mar. 13, 2014

(65) Prior Publication Data

US 2014/0309782 A1 Oct. 16, 2014

Related U.S. Application Data

(60) Provisional application No. 61/784,170, filed on Mar. 14, 2013.

(51) Int. Cl.
   *G05D 21/02* (2006.01)
   *G01N 15/14* (2006.01)
   *G01N 15/10* (2006.01)

(52) U.S. Cl.
   CPC ......... *G05D 21/02* (2013.01); *G01N 15/1404* (2013.01); *G01N 15/1425* (2013.01);
   (Continued)

(58) Field of Classification Search
   CPC ........... G05D 21/02; G01N 2015/1452; G01N 15/1425; G01N 15/1484;
   (Continued)

(56) References Cited

U.S. PATENT DOCUMENTS 5,135,759 A   8/1992  Johnson
5,199,756 A   4/1993  Bartlett et al.
(Continued)

FOREIGN PATENT DOCUMENTS

EP    1083007 A2    3/2001
WO   01/02836 A1    1/2001
(Continued)

OTHER PUBLICATIONS

DeGrooth et al., "Simple Delay Monitor for Droplet Sorters," Cytometry 12:469-472 (1991).
(Continued)

*Primary Examiner* — Shogo Sasaki
(74) *Attorney, Agent, or Firm* — McCarter & English, LLP; David R. Burns

(57) ABSTRACT

The present disclosure provides improved particle processing (e.g., cytometry and/or cell purification) systems and methods that can operate in an autonomous fashion. More particularly, the present disclosure provides for assemblies, systems and methods for analyzing, sorting, and/or processing (e.g., purifying, measuring, isolating, detecting and/or enriching) particles (e.g., cells, microscopic particles, etc.) where human intervention is not required and/or is minimized. The systems, assemblies and methods of the present disclosure advantageously improve run performance of particle processing systems (e.g., cell purification systems, cytometers) by significantly reducing and/or substantially eliminating the burden of operation for human intervention
(Continued)

by automating numerous functions, features and/or steps of the disclosed systems and methods.

11 Claims, 24 Drawing Sheets

(52) U.S. Cl.
CPC . *G01N 15/1484* (2013.01); *G01N 2015/1006* (2013.01); *G01N 2015/1406* (2013.01); *G01N 2015/149* (2013.01); *G01N 2015/1452* (2013.01)

(58) Field of Classification Search
CPC ..... G01N 2015/1406; G01N 2015/149; G01N 15/1404; G01N 2015/1006
See application file for complete search history.

(56) References Cited

U.S. PATENT DOCUMENTS

| | | | |
|---|---|---|---|
| 5,372,506 A | 12/1994 | Hambright | |
| 5,602,039 A | 2/1997 | Van den Engh | |
| 5,707,808 A * | 1/1998 | Roslaniec | C12N 15/1006 435/6.19 |
| 5,916,449 A | 6/1999 | Ellwart et al. | |
| 6,079,836 A * | 6/2000 | Burr | G01N 15/1404 356/335 |
| 6,248,590 B1 | 6/2001 | Malachowski | |
| 6,277,764 B1 | 8/2001 | Shin et al. | |
| 6,372,506 B1 | 4/2002 | Norton | |
| 6,549,275 B1 | 4/2003 | Cabuz et al. | |
| 6,589,792 B1 | 7/2003 | Malachowski | |
| 6,808,075 B2 | 10/2004 | Bohm et al. | |
| 6,941,005 B2 | 9/2005 | Lary et al. | |
| 6,970,245 B2 | 11/2005 | Fritz et al. | |
| 7,012,589 B1 | 3/2006 | Satou et al. | |
| 7,012,689 B2 | 3/2006 | Sharpe | |
| 7,215,425 B2 | 5/2007 | Rezachek et al. | |
| 7,311,476 B2 | 12/2007 | Gilbert et al. | |
| 7,417,734 B2 | 8/2008 | Kanda | |
| 7,492,522 B2 | 2/2009 | Gilbert et al. | |
| 7,569,788 B2 | 8/2009 | Deshpande et al. | |
| 7,671,987 B2 * | 3/2010 | Padmanabhan | G01N 15/1484 356/338 |
| 7,691,636 B2 | 4/2010 | Frazier et al. | |
| 7,758,811 B2 | 7/2010 | Durack et al. | |
| 7,855,078 B2 * | 12/2010 | Evans | G01N 15/1404 324/71.4 |
| 8,123,044 B2 | 2/2012 | Johnson et al. | |
| 8,140,300 B2 | 3/2012 | Dunne et al. | |
| 8,277,764 B2 | 10/2012 | Gilbert et al. | |
| 8,358,412 B2 | 1/2013 | Kanda | |
| 8,681,335 B2 | 3/2014 | Sharpe et al. | |
| 8,705,031 B2 | 4/2014 | Sedoglavich et al. | |
| 8,731,860 B2 | 5/2014 | Charles et al. | |
| 8,922,646 B2 | 12/2014 | Neckels et al. | |
| 9,029,724 B2 | 5/2015 | Hashimoto et al. | |
| 2009/0116005 A1 | 5/2009 | Furuki et al. | |
| 2011/0196637 A1 | 8/2011 | Sharpe et al. | |
| 2012/0009025 A1 | 1/2012 | Gilbert et al. | |
| 2012/0200857 A1 | 8/2012 | Sharpe et al. | |
| 2012/0202237 A1 | 8/2012 | Sedoglavich et al. | |
| 2012/0277902 A1 | 11/2012 | Sharpe et al. | |
| 2013/0256136 A1 | 10/2013 | Muraki et al. | |
| 2013/0258075 A1 | 10/2013 | Muraki et al. | |
| 2013/0334407 A1 | 12/2013 | Perrault, Jr. et al. | |

FOREIGN PATENT DOCUMENTS

| | | |
|---|---|---|
| WO | 2004/088283 A2 | 10/2004 |
| WO | 2012/106294 A1 | 8/2012 |

OTHER PUBLICATIONS

International Preliminary Report on Patentability issued in International Application No. PCT/US2014/026858, mailed Sep. 15, 2015.
International Search Report and Written Opinion issued in International Application No. PCT/US2014/026858, mailed Sep. 22, 2014.
Invitation to Pay Additional Fees issued in International Application No. PCT/US2014/026858, mailed Jul. 7, 2014.
Lazebnik, et al., "Drop-Delay Measurement Using Enzyme-Coated Particles," Cytometry, 13:649-652 (1992).
M.G. Macey: Flow Cytometry: Principles and Applications. May 3, 2007, pp. 257-276.
H. Shapiro, Practical Flow Cytometry, 2003, pp. 257-271.
Timothy W. Petersen and Ger van den Engh, "Stability of the Breakoff Point in a High-Speed Cell Sorter," Cytometry Part A, 56A:63-70 (2003).
English Translation of First Office Action for CN application 201480028017.6 dated Jun. 26, 2017, pp. 1-10.
T.R. Akylas: Advanced Fluid Dynamics, Lecture 5: Fluid Jets, http://web.mit.edu/2.21/www/Lec-notes/Surfacetension/Lecture5.pdf., Jan. 2014.

* cited by examiner

US 9,964,968 B2

OPERATORLESS PARTICLE PROCESSING SYSTEMS AND METHODS

RELATED APPLICATION

This application claims the benefit of priority to U.S. Provisional Application Ser. No. 61/784,170, titled "Operatorless Particle Processing Systems and Methods," and filed Mar. 14, 2013, the content of which is hereby incorporated by reference in its entirety.

TECHNICAL FIELD

The present disclosure relates to particle processing systems and methods that can operate in an operatorless fashion and, more particularly, to assemblies, systems, methods and steps associated with processing particles where human intervention is not required and/or is minimized.

BACKGROUND

In general, particle processing (e.g., cytometry) systems (e.g., cytometers) and methods are known. For example, some approaches to particle processing or analyzing (e.g., cell purification) systems such as sorting flow cytometers and other particle processing systems have proven to be useful in life science research, industrial, agricultural, diagnostics, and other medical applications.

In general, a cytometer can be described as a system that can measure large numbers of homogeneous and/or heterogeneous particle sets to achieve statistically relevant data sets that can be used to group and/or identify subpopulations that reside within a given particle population (e.g., within one or more samples). These measurements are sometimes performed optically (whether they are intrinsic or responsive to an optical stimulus), or they may be electrical in nature (or some other physical, chemical, or biological characteristic) as a stream of particles passes through a measurement or inspection zone. The particle sets may include biological entities such as cells (e.g., bacteria, viruses, organelles, yeasts, spores, genetic material, spermatozoa, egg cells, multicellular organisms), or other organisms, or other naturally occurring or synthetic/synthetically derived objects.

With the addition of sort functionality, a cytometer can also be used to isolate (e.g., physically separate) one or more particles of interest from a given/presented sample through human/operator control. See, e.g., U.S. Pat. No. 6,248,590, the entire content of which is hereby incorporated by reference in its entirety. In general, this technique can be used to classify and/or separate (e.g., purify or enrich) one or more populations as defined by the operator.

SUMMARY

The present disclosure relates to particle processing systems, methods, and steps that can operate in an autonomous fashion and, more particularly, to assemblies, systems, methods, and steps for analyzing, sorting, and/or processing particles where human intervention is not required. The present disclosure also relates to particle processing systems and methods that can operate in a semi-autonomous fashion and, more particularly, to assemblies, systems and methods for analyzing, sorting, and/or processing particles where human intervention is minimized.

The present disclosure provides advantageous particle processing or analyzing systems and methods that can operate autonomously (i.e., without operator intervention and/or having remote-controlled features). In general, the systems, assemblies and methods of the present disclosure advantageously improve run performance of particle processing systems (e.g., cell purification systems, cytometers) by providing systems and methods that significantly automate numerous functions, features and/or steps of the disclosed systems and methods. In exemplary embodiments, the present disclosure provides for improved assemblies, systems, methods, and process steps associated with setting up, calibrating, aligning, analyzing, sorting, and/or processing (e.g., purifying, measuring, isolating, detecting, monitoring and/or enriching) particles (e.g., cells, microscopic particles, etc.) where human intervention is not required and/or is minimized.

The present disclosure provides for a particle processing system including a detection region; a particle processing region; one or more sensors sensing one or more operational characteristics of the particle processing system; and a processor programmed and/or configured to automatically change one or more parameters of the particle processing system based on the one or more operational characteristics sensed by the one or more sensors.

The present disclosure also provides for a particle processing system including a particle delivery assembly; a signal source assembly; a particle analysis region assembly; a particle collection assembly; a signal detector assembly; at least one sensor assembly adapted to sense or monitor at least one processing feature of the particle delivery assembly, signal source assembly, particle analysis region assembly, particle collection assembly or signal detector assembly; at least one processor in communication with the at least one sensor assembly and the particle delivery assembly, signal source assembly, particle analysis region assembly, particle collection assembly or signal detector assembly; wherein the at least one processor and the at least one sensor assembly, and the particle delivery assembly, signal source assembly, particle analysis region assembly, particle collection assembly or signal detector assembly are configured and adapted to process particles in an operatorless fashion.

The present disclosure also provides for a particle processing system including a particle delivery assembly in communication with a first sensing member, the first sensing member adapted to sense or monitor at least one processing feature of the particle delivery assembly; a signal source assembly in communication with a second sensing member, the second sensing member adapted to sense or monitor at least one processing feature of the signal source assembly; a particle analysis region assembly in communication with a third sensing member, the third sensing member adapted to sense or monitor at least one processing feature of the particle analysis region assembly; a particle collection assembly in communication with a fourth sensing member, the fourth sensing member adapted to sense or monitor at least one processing feature of the particle collection assembly; a signal detector assembly in communication with a fifth sensing member, the fifth sensing member adapted to sense or monitor at least one processing feature of the signal detector assembly; at least one processor in communication with: (i) the first sensor assembly, second sensor assembly, third sensor assembly, fourth sensor assembly and fifth sensor assembly, and (ii) the particle delivery assembly, signal source assembly, particle analysis region assembly, particle collection assembly and signal detector assembly; wherein the at least one processor and the first sensor assembly, second sensor assembly, third sensor assembly, fourth sensor assembly, fifth sensor assembly, particle delivery assembly, signal source assembly, particle analysis region assembly, particle collection assembly and signal detector assembly are configured and adapted to process particles in an operatorless fashion.

The present disclosure also provides for a particle processing system including a particle delivery assembly, the particle delivery assembly configured to deliver a stream containing particles to an inspection region; an electromagnetic radiation source assembly; a particle collection assembly; a signal detector assembly; at least one sensor assembly adapted to sense or monitor at least one processing feature of the particle delivery assembly, electromagnetic radiation source assembly, particle inspection region, particle collection assembly or signal detector assembly; at least one processor in communication with the at least one sensor assembly and the particle delivery assembly, electromagnetic radiation source assembly, particle inspection region, particle collection assembly or signal detector assembly; wherein the at least one processor and the at least one sensor assembly, and the particle delivery assembly, electromagnetic radiation source assembly, particle inspection region, particle collection assembly or signal detector assembly are configured and adapted to process particles in an operatorless fashion.

The present disclosure also provides for a particle processing system including a particle delivery assembly; an electromagnetic radiation source assembly; a microfluidic assembly, the microfluidic assembly including a particle inspection region; a particle collection assembly; an optical detector assembly; at least one sensor assembly adapted to sense or monitor at least one processing feature of the particle delivery assembly, electromagnetic radiation source assembly, microfluidic assembly, particle collection assembly or optical detector assembly; at least one processor in communication with the at least one sensor assembly and the particle delivery assembly, electromagnetic radiation source assembly, microfluidic assembly, particle collection assembly or optical detector assembly; wherein the at least one processor and the at least one sensor assembly, and the particle delivery assembly, electromagnetic radiation source assembly, microfluidic assembly, particle collection assembly or optical detector assembly are configured and adapted to process particles in an operatorless fashion.

The present disclosure also provides for a particle processing system including a plurality of particle processing assemblies, each particle processing assembly including: a detection region; a particle processing region; one or more sensors, the one or more sensors sensing one or more operational characteristics of the associated particle processing assembly; and a processor programmed and/or configured to automatically change one or more parameters of its associated particle processing assembly based on the one or more operational characteristics sensed by the one or more sensors.

The present disclosure also provides for a particle processing system including a detection region; a particle processing region; one or more sensors sensing one or more operational characteristics of the particle processing system; and a remote processor, the remote processor programmed and/or configured to remotely control or change one or more parameters of the particle processing system based on the one or more operational characteristics sensed by the one or more sensors.

Any combination or permutation of embodiments is envisioned. Additional advantageous features, functions and applications of the disclosed systems, assemblies and methods of the present disclosure will be apparent from the description which follows, particularly when read in conjunction with the appended figures.

BRIEF DESCRIPTION OF THE DRAWINGS

Exemplary embodiments of the present disclosure are further described with reference to the appended figures. It is to be noted that the various features and combinations of features described below and illustrated in the figures can be arranged and/organized differently to result in embodiments which are still within the spirit and scope of the present disclosure. To assist those of ordinary skill in the art in making and using the disclosed systems, assemblies and methods, reference is made to the appended figures.

FIGS. 4(i) and 4(ii) illustrate screen shots of an exemplary embodiment of an aspect of a particle processing system according to the present disclosure.

In the description which follows, like parts are marked throughout the specification and drawings with the same reference numerals, respectively. Drawing figures are not necessarily to scale and in certain views, parts may have been exaggerated for purposes of clarity.

DETAILED DESCRIPTION

Figure 1:
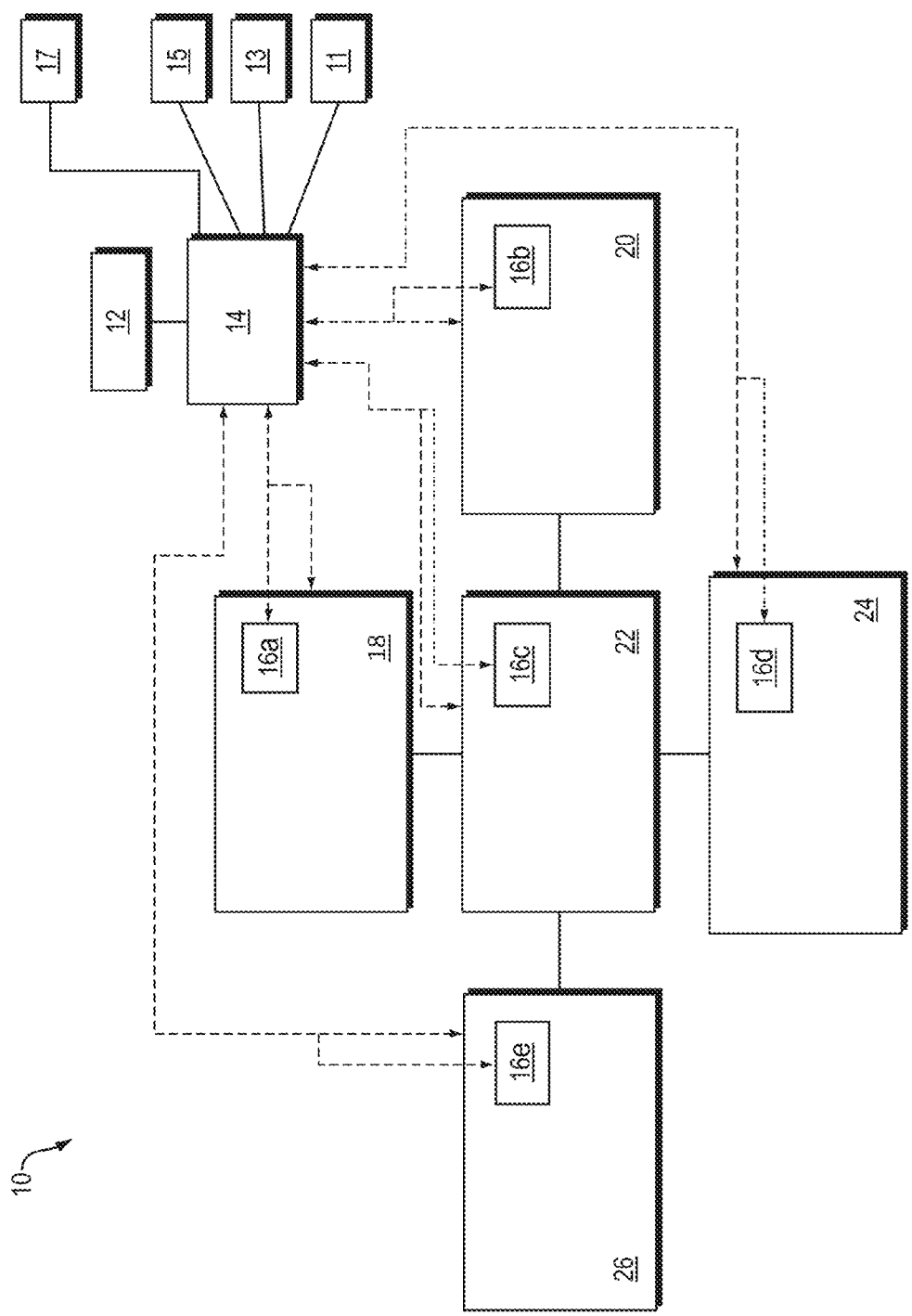
FIG. 1 is a block diagram of an exemplary embodiment of a particle processing system according to the present disclosure.

The present disclosure relates to particle processing (e.g., cytometry including flow cytometry using drop sorters and microfluidic based sorters, and/or cell purification) systems and methods that can operate in an autonomous fashion and, more particularly, to assemblies, systems and methods for analyzing, sorting, and/or processing (e.g., purifying, measuring, isolating, detecting, monitoring and/or enriching) particles (e.g., cells, microscopic particles, etc.) where human intervention is not required and/or is minimized.

The present disclosure provides improved particle processing (e.g., cytometry and/or cell purification) systems and methods that can operate in an autonomous fashion (or in a substantially autonomous fashion). In general, the present disclosure provides for assemblies, systems and methods for analyzing, sorting, and/or processing particles where human intervention is not required or is minimized. Stated another way, the systems, assemblies and methods of the present disclosure advantageously improve run performance or operational characteristics of particle processing systems (e.g., cell purification systems, cytometers) by significantly reducing and/or substantially eliminating the burden of operation for human intervention by automating numerous functions, features and/or steps of the disclosed systems and methods.

In current practice, some of the challenges that arise when utilizing or operating a particle processing system or assembly place many demands and skill requirements on human operators to ensure run performance or instrument operation. In general, run performance may be measured in terms of: 1) the time taken to prepare a sample or the cytometer for initiating measurements or sorting (including instrument start-up, calibration, preparation, and/or the insertion of sample and any other associated components such as collection vessels); 2) the rate at which a particular measurement and/or sort is performed (e.g., presenting sample to measurement region and obtaining required data set and/or isolated particle fraction); 3) the quality of run (e.g., sustained calibration and performance during a particular measurement or sort operation), the efficiency of the process, the recovery and/or yield of the desired particles, the handling (and therefore state) of sample that is in contact or used with the cytometer; 4) the reliability and accuracy of obtaining data from the measurement; 5) the successful identification, enumeration, isolation, purification, enrichment and/or sorting of particles or particle populations; 6) the removal of input and/or output samples; 7) the careful/controlled post-measurement cleaning procedures prior to running further samples or instrument shut-down; and 8) the on-going monitoring of all system functions related to preventative or unplanned maintenance or repair.

In exemplary embodiments, the present disclosure provides for improved particle processing (e.g., cytometry and/or cell purification) systems and methods where for some or all of the particle processing steps human intervention is not required or is minimized, thereby providing a significant commercial and/or operational advantage as a result.

Operation in an autonomous or (substantially autonomous) fashion, where human intervention is not required (or is substantially not required) is referred to herein as "operatorless." A process or subprocess that can operate in an operatorless mode does not require a skilled operator and does not require decisions to be made based on a knowledge of the particles being processed or of the inner workings of the system. Thus, for example, a system may be considered "operatorless" even if it requires a user to periodically press a button or interact with system in some way to continue the operatorless operation, to direct the results to a specific computer storage location, to otherwise maintain the status quo, or make other non-process specific, non-functional, non-characterizing, non-analytical and/or non-diagnostic decisions, or the like. The present disclosure relates to particle processing systems and methods that can operate in an operatorless fashion and, more particularly, to assemblies, systems, methods and steps associated with processing particles where human intervention is not substantively required.

Referring now to the drawings, and in particular to FIG. 1, there is illustrated a block diagram of an exemplary embodiment of a particle processing system 10 according to the present disclosure. In general, particle processing system 10 is configured, dimensioned and adapted for analyzing, sorting, and/or processing (e.g., purifying, measuring, isolating, detecting, monitoring and/or enriching) particles (e.g., cells, microscopic particles, etc.) or the like, and wherein human intervention is not required and/or is minimized for some or all of the particle processing steps.

For example, system 10 may be a cytometry and/or a cell purification system or the like, although the present disclosure is not limited thereto. It is noted that exemplary cytometry systems 10 can include, without limitation, drop sorters (e.g., droplet or continuous jet systems) or the like, or microfluidic flow sorters (e.g., microfluidic chip based systems that do not form drops) or the like.

As shown in FIG. 1, system 10 includes at least one processor 14 (e.g., a central automation processor or master processor). System 10 also includes at least one display device 12 in communication with the processor 14. It is noted that processor 14 may be the main central processing unit of system 10, or it may be an access point to system 10. Further, processor 14 may be a distributed processor.

In exemplary embodiments, system 10 includes a particle delivery assembly 18, a signal source assembly 20, a particle analysis or processing region assembly 22, a particle collection assembly 24 and a signal detection assembly 26. Processor 14 is in communication with particle delivery assembly 18, signal source assembly 20, particle analysis region assembly 22, particle collection assembly 24 and/or signal detection assembly 26. These assemblies may be physical assemblies or groupings of physical subassemblies, functional assemblies or groupings of functional subassemblies, or a combination of physical and functional subassemblies.

In general, system 10 includes at least one sensor assembly/member 16 that is configured and adapted to sense or monitor at least one operational characteristic or processing feature of system 10 (e.g., sense or monitor at least one characteristic or feature of particle delivery assembly 18, signal source assembly 20, particle analysis region assembly 22, particle collection assembly 24 and/or signal detector assembly 26). The at least one sensor assembly 16 may include a plurality of individual sensors or detectors. These individual sensors or detectors may be distributed over any given assembly 18, 20, 22, 24, 26 and have any functionality. The sensor assembly 16 is in signal communication (e.g., wired and/or wireless communication) with processor 14.

Sensor assembly/member 16 may include by way of non-limiting examples, photodetectors and or imaging devices.

As shown in FIG. 1, processor 14 may be in communication with (e.g., one or a plurality) keypads and/or user stations 11, third-party devices 13 and/or additional processors or controllers 15. Moreover, processor 14 may be capable of communication with a network or internet 17, and may be capable of sending or receiving audio, video and/or data or the like.

Processor 14 is generally programmed and/or configured to monitor and change as necessary (e.g., automatically change) one or more parameters of system 10 (e.g., of particle delivery assembly 18, signal source assembly 20, particle analysis region assembly 22, particle collection assembly 24 and/or signal detector assembly 26) based on the one or more operational characteristics sensed by the one or more sensor members 16. More particularly, system 10 includes at least one sensor assembly 16 adapted to sense or monitor at least one processing feature of the particle delivery assembly 18, signal source assembly 20, particle analysis region assembly 22, particle collection assembly 24 and/or signal detector assembly 26. Processor 14 is generally configured and adapted to enable or facilitate system 10 to process particles in an operatorless fashion (e.g., to automatically change one or more parameters of system 10 based on the one or more operational characteristics sensed by the one or more sensor members 16). In general, processor 14 is configured to transmit and/or receive signals (e.g., command and/or status signals) or the like to or from sensor assemblies 16 and/or particle delivery assembly 18, signal source assembly 20, particle analysis region assembly 22, particle collection assembly 24 and/or signal detector assembly 26, in order to change the status and/or operating parameters of particle delivery assembly 18, signal source assembly 20, particle analysis region assembly 22, particle collection assembly 24 and/or signal detector assembly 26. Stated another way, processor 14 generally is in communication with sensors 16 and/or the components of system 10 for control and/or communication purposes.

For example, processor 14 may send command signals to a sensor assembly 16 (e.g., based on an operational characteristic sensed by that sensor 16) associated with particle delivery assembly 18 (and/or directly to assembly 18) to control and/or change the status or operating parameter of particle delivery assembly 18. Moreover, processor 14 may receive status signals from sensor assemblies 16 regarding the status of the components of system 10 (e.g., status of signal detector assembly 26, etc.).

It is to be noted that each sensor assembly 16 may include or be associated with a local processor and/or processing or control unit (e.g., signal processing control unit) or the like. As such, each sensor assembly 16 may be in communication with at least one component (e.g., assembly 18) of system 10 for control and/or communication purposes (e.g., independent of and/or in conjunction with processor 14). For example, a processor and/or processing control unit local to and/or associated with each sensor assembly 16 may send command signals directly to a component (e.g., assembly 18) of system 10 to control and/or change the status or operating parameter of that component. Such command signals may or may not be directed from processor 14, and may be communicated to and/or from processor 14, although the present disclosure is not limited thereto. In exemplary embodiments, each assembly 18, 20, 22, 24 and/or 26 may include a processor or the like that may operate independent of and/or in conjunction with processor 14 for control and/or communication purposes associated with the components of system 10.

In exemplary embodiments and as shown in FIG. 1, system 10 includes a first sensor assembly 16a that is configured and adapted to sense or monitor at least one operational characteristic or processing feature of the particle delivery assembly 18, a second sensor assembly 16b that is configured and adapted to sense or monitor at least one operational characteristic or processing feature of the signal source assembly 20, a third sensor assembly 16c that is configured and adapted to sense or monitor at least one operational characteristic or processing feature of the particle analysis region assembly 22, a fourth sensor assembly 16d that is configured and adapted to sense or monitor at least one operational characteristic or processing feature of the particle collection assembly 24, and a fifth sensor assembly 16e that is configured and adapted to sense or monitor at least one operational characteristic or processing feature of the signal detector assembly 26. As such, processor 14 may be configured and adapted to enable or facilitate system 10 or certain aspects of system 10 to process particles in an operatorless fashion based on the operational characteristics sensed by the first, second, third, fourth and/or fifth sensor assemblies 16a-e. It is to be noted that one or more sensor assemblies may be associated with each assembly 18, 20, 22, 24 and/or 26. Further, it is to be noted that system 10 may have any number of sensor assemblies 16a-"n" in communication with processor 14.

As discussed further below, some of the operational characteristics that may be monitored/sensed (e.g., via sensors 16) and/or run/maintained in an operatorless fashion (e.g., via processor 14 and sensors 16) may include, without limitation, the following aspects and/or or features of the components of system 10:

(i) instrument start-up (e.g., power sources; electrical sources; laser sources; excitation sources; fluidics; air/vacuum; pumps; detection system; processors/computers; sub-systems; safety mechanisms; self-tests; self-calibration; self-diagnose issues; self-identification of current state (e.g., readiness) for sorting; communication of status);

(ii) input sample (e.g., identification of input sample (what is it for recording, traceability, acceptance, sequencing, measurement or sorting) and/or input sample vessel; presence of sample; quantity of sample at any given time);

(iii) insertion of sample (e.g., initial insertion of sample to system 10 (from or within container); running (flow) of sample; regulation and/or control of sample flow and/or sample flow rate dynamically (periodically and/or to a set-point that is defined automatically or in advance during instrument set-up/manufacture/calibration); monitoring sample volume or level; monitoring event rate and altering sample pressure and/or expulsion rates to achieve a desired set-point for particle event (input) rate);

(iv) sort collection (e.g., vessel insertion/removal; position of vessels (waste, sorted fraction) or of unitary cartridge; sealing of fluidic and/or other necessary connections required to enable system 10 operation; identification and/or selection of particles or particle populations of interest for measurement and/or sorting);

(v) sort mode and/or automated adjustment/alignment of operating conditions (e.g., to enable predefined/user specified purity/efficiency and/or recovery/yield modes (event rate, gating schemes, sort rate, abort rate, peak-to-valley ratio); applying various data manipulation algorithms to calculate and/or automatically adjust data that may be visualized as a rotation or other translation function on one or more dimensions on data sets and/or on bivariate data plots to assist with the projection of data in histogram views; adjustment of parameters to bring particle population within acceptable signal limits to enable reliable measurement of particles or to enable certain data to be displayed visually (sensitivity/gain/position and/or photodetector amplification) using software/firmware or hardware);

(vi) monitoring of particle clusters/populations and/or cluster positions based on certain data representations (e.g., monitor and then adjust data/sort region conditions or boundaries (tracking) to account for minor fluctuations in measured signal levels so that sorting (particle processing) may continue with minimal impact on sort purity and recovery);

(vii) adjusting a sort mechanism (e.g., sort monitor and/or drop monitor and/or side streams/calibration/timing and/or particle/drop trajectory and/or velocity and expected arrival at sort position/mechanism to enable reliable/reproducible/stable performance of particle separation to meet the desired outcome (such as given number of particles, purity, ratio, recovery, yield, characteristic property, homogeneity, heterogeneity, size, morphology, fluorescence, light scatter properties, DNA content, and the like);

(viii) adjusting optical measurement apparatus (e.g., through positioning various mechanical or optical components, or by effecting the direction or position of one or more optical paths or particle paths to enable reliable and consistent measurement and/or sorting of particles flowing within system 10 (e.g., within or associated with the cytometer apparatus);

(ix) monitor and control functions (e.g., system leaks (gas/liquid); out-of-bounds (power, safe shut-down, universal power supply, safety and control network, etc.); trending (e.g., sample quality, sort rate, sort fraction, assessment of live to dead cell ratio within a sample, scheduling of samples, alarm conditions and alarms); intelligent error handling such as self-fixing, self-regulation or other act such as by reacting to system 10 parameters (e.g., temperature, pressure, vacuum, alignment movement, etc.) and/or parameter changes that may affect system operation);

(x) various alerts and/or alarms (e.g., alerts/alarms that caution device/user that system is nearing or operating outside acceptable limits; run and control fluid (sheath, waste, sample, sort fraction and trajectory of sort and non-sort fractions) level monitor and refill; cleaning lines; sample waste; etc.);

(xi) safety aspects (e.g., safety of environment or environment of operator or sample or system/instrument); potential exposure of sample to the environment, the apparatus, and other samples;

(xii) automated and/or robotic feeding of samples, sheath fluid(s), sort output fractions, waste and other required fluids, consumables, calibration parts, cleaning supplies, etc. (e.g., systems/methods to enable continuous operation over extended periods (e.g., for different samples) without the need for human intervention);

(xiii) remote-controlled features and/or operations (e.g., reduce requirement for operator to be in front of system 10, system 10 could be controlled from a remote location/room with respect to the system 10; remote-controlled features that may be particularly useful if there are concerns over sample contamination issues (between samples, or sample and system/environment, or sample and operator, as non-limiting examples), or concerns where pathogens, communicable diseases, or the like or other vectors are involved (e.g., Hepatitis C, Influenza strains, Malaria, H1N1, HIV, BSE, TB, etc.));

(xiv) other aspects or features of system 10 (e.g., nozzle alignment; laser alignment; excitation source alignment; detector alignment; data manipulation for identification and zooming; population identification; population sort regions; set-point purity; etc.);

(xv) auto-rotation and/or translation (e.g., calculating and automatically adjusting data rotation on one or more bivariate plots to assist with projection of data in histogram views and related gating or sort strategies; adjusting fluorescence compensation parameters);

(xvi) fluidic stability (e.g., monitoring droplet break-off image and automatically adjusting amplitude and phase controls to maintain position and profile/shape at neck of last attached drop);

(xvii) sort timing (e.g., determine droplet break-off or timed microfluidic actuation/switch delay without the need for user intervention);

(xviii) sample flow rate (e.g., monitoring event rate and controlling sample pressure to achieve a desired set-point for particle event rate);

(xix) optical alignment of jet or microfluidic channel (e.g., image-based alignment of nozzle and/or excitation source to predefined position where image is adjusted with respect to expected conditions);

(xx) data-based alignment (e.g., data-based alignment of nozzle, microfluidic chip channel(s), excitation source(s) and/or detector position(s) using feedback from measured photodetector signals (e.g., from calibration or target particles; identify and locate sort regions around desired cell or other particle populations) (Non-limiting examples include: using system 10 for the sorting of sperm by measuring DNA content to identify and isolate X- and/or Y-chromosome-bearing sperm; isolating cells for human therapeutic applications such as those isolated using immunophenotypic, internal, surface, markers or other intrinsic characteristics; isolating cells in industrial processes, or in life science research, where cells can be identified and selected based on intrinsic characteristics, or some other attribute following a sample preparation step (such as by adding a stain as a non-limiting example)); and/or (xxi) sort stream path and/or trajectory (e.g., determine droplet deflection conditions such as position, fanning, charge timing, waste centering, etc.).

The present disclosure will be further described with respect to the following examples; however, the scope of the disclosure is not limited thereby. The following examples illustrate the systems and methods of the present disclosure of analyzing, sorting, and/or processing (e.g., purifying, measuring, isolating, detecting, monitoring and/or enriching) particles (e.g., cells, microscopic particles, etc.) or the like in an autonomous fashion.

EXAMPLE 1

Drop Sorter Particle Processing System

Figure 2:
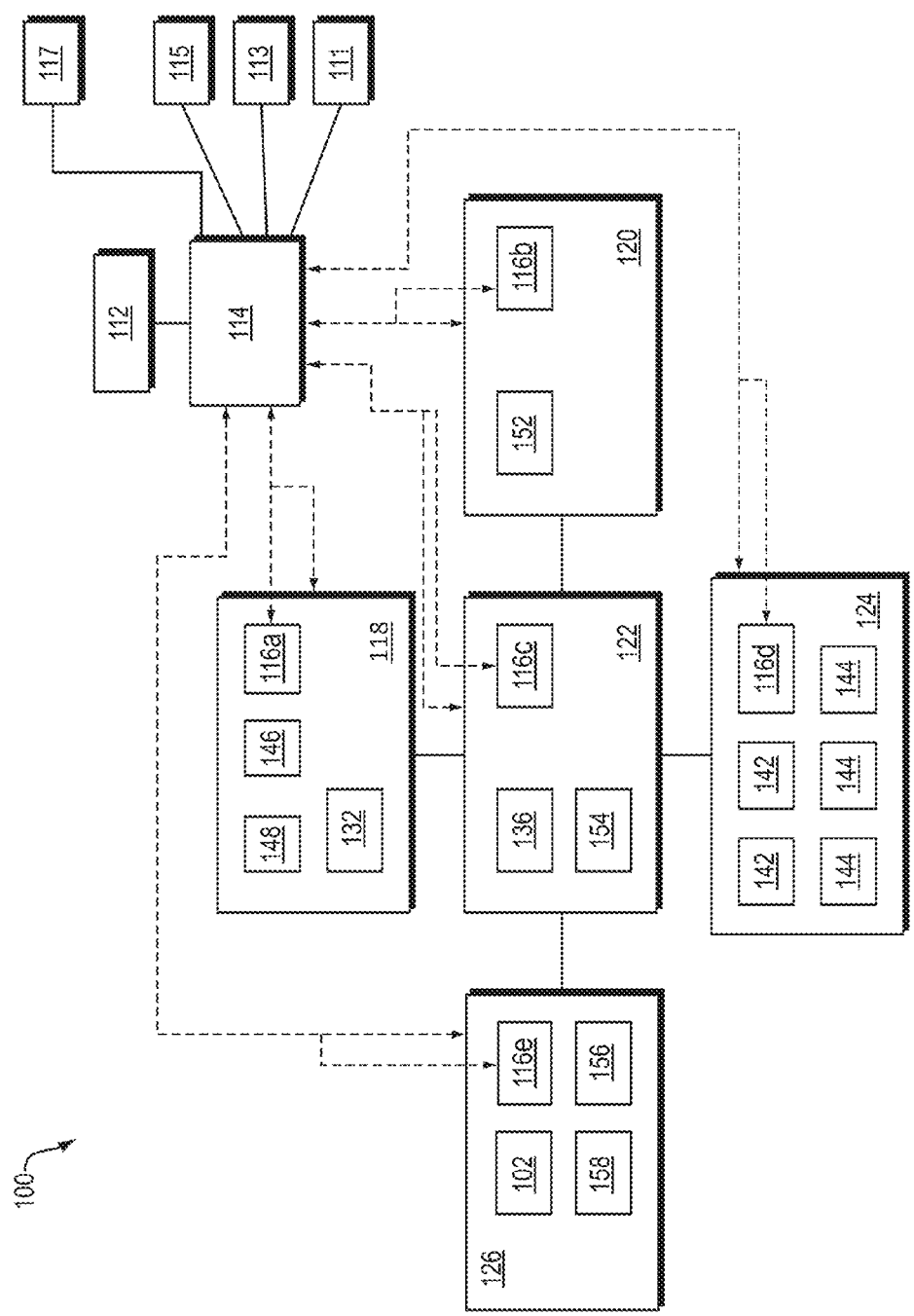
FIG. 2 is a block diagram of another exemplary embodiment of a particle processing system according to the present disclosure.

Referring again to the drawings, and in particular to FIG. 2, there is illustrated a block diagram of another exemplary embodiment of a particle processing system 100 according to the present disclosure. Similar to system 10, particle processing system 100 is configured, dimensioned and adapted for analyzing, sorting, and/or processing (e.g., purifying, measuring, isolating, detecting, monitoring and/or enriching) particles (e.g., cells, microscopic particles, etc.) or the like, and wherein human intervention is not required or is minimized.

For example, system 100 may be a cytometry and/or a cell purification system or the like, although the present disclosure is not limited thereto. In exemplary embodiments, system 100 is a drop sorter particle processing system 100 (e.g., a cytometer system; a droplet or continuous jet system, etc.) or the like. Exemplary drop sorter particle processing systems/components are disclosed, for example, in U.S. Pat. Nos. 8,277,764; 7,012,689; 6,372,506 and 6,248,590; and U.S. Patent Publication Nos. 2012/0200857 and 2012/0202237; the foregoing being incorporated herein by reference in their entireties.

Similar to system 10 and as shown in FIG. 2, system 100 includes at least one processor 114 (e.g., a central automation processor or master processor). At least one display device 112 is in communication with processor 114. Processor 114 may also be in communication with (e.g., one or a plurality of) keypads and/or user stations 111, third-party devices 113 and/or additional processors or controllers 115. Processor 114 may be capable of communication with a network or internet 117, and may be capable of sending and/or receiving audio, video and/or data or the like.

Figure 3:
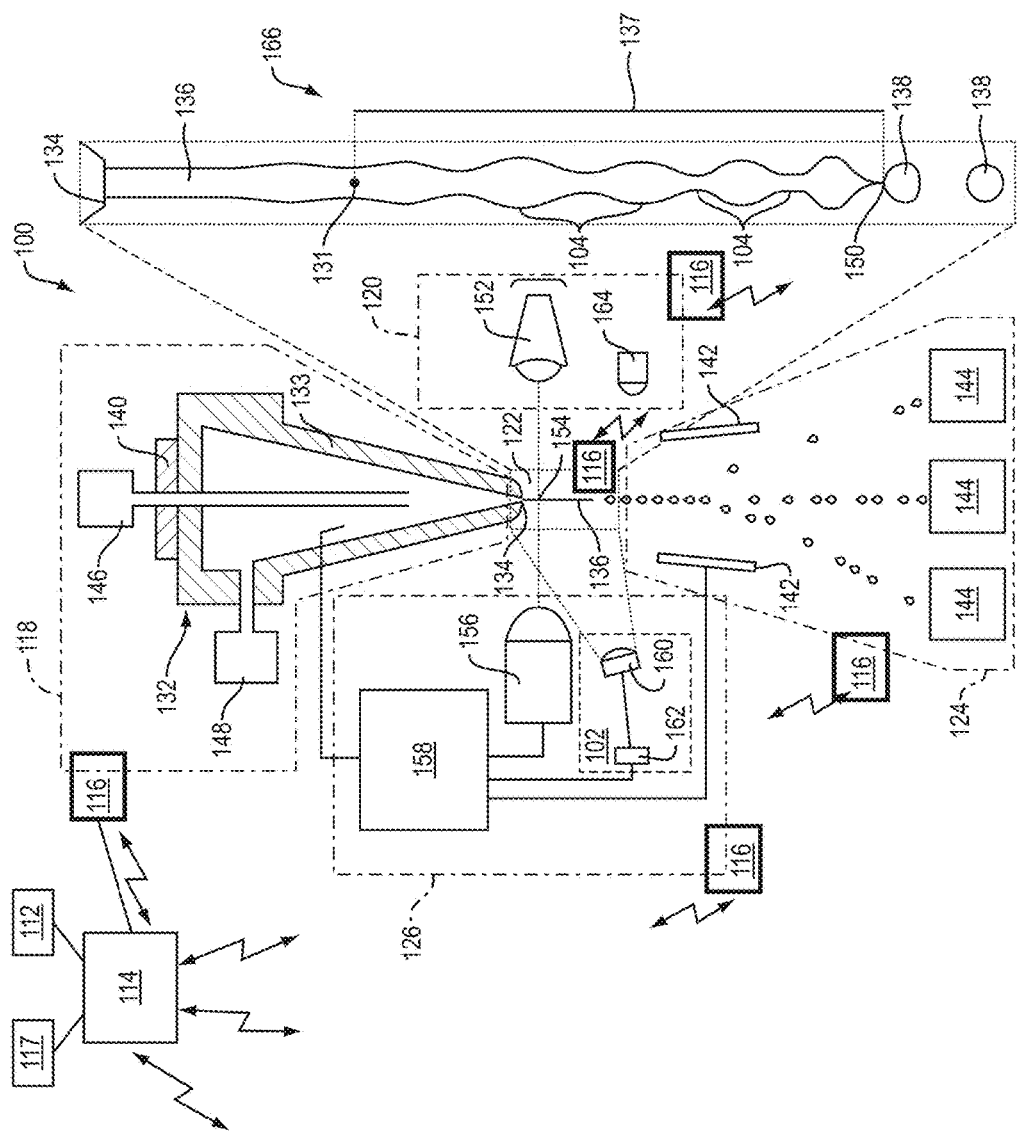
FIG. 3 illustrates an exemplary particle processing system of FIG. 2.

In exemplary embodiments, system 100 includes a particle delivery assembly 118, the particle delivery assembly 118 generally configured and dimensioned to deliver a stream 136 containing particles or the like to a particle inspection region assembly 122 (FIGS. 2-3). System 100 also includes signal source assembly provided as an electromagnetic radiation source assembly 120, a particle collection assembly 124 and a signal detector/detection assembly 126. Processor 114 is in communication with particle delivery assembly 118, electromagnetic radiation source assembly 120, particle inspection region assembly 122, particle collection assembly 124 and/or signal detector assembly 126.

Like system 10, particle processing system 100 includes at least one sensor assembly/member 116 that is configured and adapted to sense or monitor at least one operational characteristic or processing feature of system 100 (e.g., sense or monitor at least one characteristic or feature of particle delivery assembly 118, electromagnetic radiation source assembly 120, particle inspection region assembly 122, particle collection assembly 124 and/or signal detector assembly 126). Each sensor assembly 116a-"n" may be in communication with (e.g., electrical communication, wireless communication, etc.) and/or operatively coupled to processor 114. System 100 may include a plurality of sensor assemblies 116a-e.

Referring to FIGS. 2 and 3, it is to be noted that system 100 may be a droplet sorter system or the like, and may include a processor 114, a plurality of assemblies 118, 120, 122, 124 and/or 126, and a plurality of sensors 116a-"n". Further, system 100 may be a multi-nozzled droplet sorter system or the like, and may include a plurality of processors 114, a plurality of any or all of the assemblies 118, 120, 122, 124, 126, and a plurality of any or all of the sensors 116a-"n".

In general, processor 114 is configured to change or adjust one or more parameters, features, characteristics and/or components of system 100 based on the one or more operational characteristics sensed by the one or more sensor members 116. In certain embodiments, a modicum of input may be requested of an operator. In certain preferred embodiments, system 100 may be configured to automatically change or adjust one or more parameters, features, characteristics and/or components based on the one or more operational characteristics sensed by the one or more sensor members 116. As such, processor 114 may generally be configured and adapted to enable or facilitate system 100 to process particles or to perform certain particle processing steps in an operatorless fashion.

In general, processor 114 is configured to transmit or receive signals (e.g., command/status signals) or the like to/from sensor assemblies 116a-e and/or particle delivery assembly 118, electromagnetic radiation source assembly 120, particle inspection region assembly 122, particle collection assembly 124 and/or signal detector assembly 126, in order to change the status and/or operating parameters of particle delivery assembly 118, electromagnetic radiation source assembly 120, particle inspection region assembly 122, particle collection assembly 124 and/or signal detector assembly 126. Stated another way, processor 114 is in communication with sensors 116a-e and/or the components of system 100 for control and/or communication purposes.

For example, processor 114 may send command signals to a sensor assembly 116a associated with particle delivery assembly 118 (and/or directly to a component within particle delivery assembly 118) to control an operating parameter of the particle delivery assembly 118. Moreover, processor 114 may receive status signals from sensor assemblies 116a-e regarding the status of the components of system 100.

Each sensor assembly 116 may include or be associated with a local processor and/or processing control unit (e.g., signal processing control unit) or the like. As such, each sensor assembly 116 may be in communication with at least one component (e.g., assembly 118) of system 100 for control and/or communication purposes (e.g., independent of and/or in conjunction with processor 114). For example, the processor or control unit local to and/or associated with each sensor assembly 116 may send command signals directly to a component (e.g., assembly 118) of system 100 to control an operating parameter of that component. Such command signals may or may not be directed from processor 114, and may be communicated to and/or from processor 114, although the present disclosure is not limited thereto. In exemplary embodiments, each assembly 118, 120, 122, 124 and/or 126 can include a local processor or the like that can operate independent of and/or in conjunction with processor 114 for control and/or communication purposes associated with the components of system 100.

Processor 114 and/or sensors 116a-e may advantageously be configured and adapted to enable or facilitate system 100 or certain aspects of system 100 to process particles in an operatorless fashion based on the operational characteristics sensed by the sensor assemblies 116a-e. Again, system 100 may have any number of sensor assemblies 116a-"n" in communication with processor 114.

Turning now to FIG. 3, an example of a drop sorter particle processing system 100 or the like is illustrated as a drop cytometer system 100 (e.g., jet-in-air flow cytometer system), although the present disclosure is not limited thereto. Rather, it is noted that the systems and methods described may be applied to other particle processing systems.

As noted above, exemplary system 100 includes a particle and/or fluid delivery assembly 118. Assembly 118 may include a nozzle 132 having a nozzle orifice 134 for delivering a fluid stream 136 to a particle inspection region 122 proximal to radiation source assembly 120.

The fluid stream 136 may be perturbed into droplets 138 by an oscillator 140. The droplets 138 may pass through an electromagnetic field produced by deflection plates 142 of particle collection assembly 124. In exemplary embodiments, a charge applied to each droplet 138 defines a path into one of one or more collection containers or members 144 of particle collection assembly 124.

In certain embodiments, the fluid stream 136 may define a substantially coaxial fluid stream having an inner core stream of sample or particles 146 and an outer stream of sheath fluid 148. The particles may be single cell organisms such as bacteria or individual cells in a fluid, such as various blood cells, sperm or nuclei derived from tissue. Depending on the application the particles may be stained with a variety of stains, probes, or markers selected to differentiate particles or particle characteristics. Some stains or markers only bind to particular structures, while others, such as DNA/RNA dyes, may bind in some manner to nuclear DNA or RNA. The particles may be stained with a fluorescent dye which emits fluorescence in response to an excitation source. As one non-limiting example, sperm may be stained with Hoechst 3334 which binds to X-chromosomes and Y-chromosomes. U.S. Pat. Nos. 5,135,759 and 7,758,811 describe exemplary methods for staining sperm, and are each incorporated herein by reference.

In oriented sperm, the relative quantity of Hoechst 33342 can be determined providing means for differentiating X-chromosome bearing sperm from Y-chromosome bearing sperm. Additionally, certain embodiments are envisioned to work with DNA sequence specific dyes and sex specific dyes.

The fluid stream 136 may exit the nozzle orifice 134 with increasingly pronounced undulations 104 or decreasing neck 106 thicknesses in a downstream direction until a break off point 150 is reached where droplets 138 break away from the fluid stream 136. The break off point 150 is illustrated as the substantially last point at which a droplet 138 contacts the fluid stream 136. In general, this location represents the last point in time a charge may be applied to a droplet 138, as a means for providing a physical sort mechanism.

Radiation source assembly 120 may include an excitation energy source 152 for providing energy (e.g., a laser, a light emitting diode, or an arc lamp, as non-limiting examples) to the fluid stream 136 and particles of interest contained in the sample 146. In exemplary embodiments, the excitation energy source 152 is aligned with an inspection zone 154 on the fluid stream 136 for interrogating particles as they pass the inspection zone 154 of particle inspection region 122. It is noted that the inspection zone 154 may be located downstream of the nozzle orifice 134, may be located within a cuvette, or may be located a flow chamber upstream or downstream of the nozzle orifice 134.

Reflected and/or emitted electromagnetic radiations from the fluid stream 136 and particles in the fluid stream 136 can be collected by a detector or sensor assembly 156 of signal detector assembly 126. The detector assembly 156 may include any number of detectors or devices configured in the forward, side, and/or back direction relative to the excitation energy source 152. For example, assembly 126 may utilize various optics (e.g., filters, minors, dichroic minors, splitters, and other reflective and/or refractive elements, etc.) to detect electromagnetic radiation at any number of wavelengths and/or in any number of directions and in a variety of combinations.

In exemplary embodiments, detected signals may be processed for the classification of particles within the fluid stream 136, and sort decisions may be made at a controller 158. Controller 158 may be a local controller associated with the signal detector assembly 126. The controller 158 may include acquisition and sort electronics in the form of analog and/or digital components for processing signals from the detector assembly 156 and applying a sort logic. Once a sort decision is made, the controller 158 may send a signal to a charge device to charge (or not charge) the fluid stream 136 through the sample 146 in the nozzle 132 so that the droplets 138 are deflected (or are not deflected) by deflection plates 142 into the appropriate container 144.

In general, the timing at which the appropriate charge is applied to the fluid stream 136 should closely match to the time a particle of interest is in a droplet 138' at the break off point 150 in order to ensure an accurate sort action. Further, a drop delay value (DDV) may be determined from when the particle of interest in detected in the detection zone 154 to when it is located in the droplet 138' at the break off point 150. In exemplary embodiments, an imaging assembly 102 may be provided to monitor or update the distance between the break off point 150 and the inspection zone 154 and to determine, monitor and update the number of undulations 104 in the fluid stream 136 to predict a current or updated drop delay value. Such drop delay information may then be communicated or transmitted to sensor assembly or assemblies 116 and/or to processor 114 for control and/or communication purposes.

For example, in one embodiment the imaging assembly 102 may include an optical system 160 and a sensing element 162 for capturing an image 166 of the fluid stream 136 for the purpose of modifying or detecting the appropriate drop delay value for accurate sort decisions. The sensing element 162 (e.g., a charge coupled device) may be capable of converting an image into a series of electrical or digital signals. Other sensors and configurations for detecting the light intensity of an image in high resolution may also be used (e.g., a photodiode array or a sensor array). A strobe 164 or the like may illuminate the fluid stream 136 at predicted intervals to create an image of the fluid stream 136 as photons interacting with the object of the fluid stream 136. The optical system 160 may include a series of optical elements for manipulating the image 166 of the fluid stream 136. As one example, the optical system 160 may comprise multiple lenses or multiple minors, other reflective or refractive elements, and combinations of different reflective and refractive elements.

In one embodiment, the optical system 160 in operation may manipulate the aspect ratio of the image 166 of the fluid stream 136, such as compressing the length of the fluid stream and/or expanding the width of the fluid stream, as disclosed and described in U.S. Patent Publication No. 2012/0200857, the content of which is hereby incorporated by reference in its entirety. By manipulating the aspect ratio to form a manipulated image of the fluid stream, exemplary optical system 160 may serve to acquire and preserve relevant information pertaining to the drop delay value. Such an optical system 160 for modifying an image of a fluid stream 166 may provide, in a single image, enough information to determine or modify drop delay values. In exemplary embodiments, such information may be communicated to sensor assembly or assemblies 116 and/or to processor 114 for control and/or communication purposes. However, it is to be noted that optical system 160 and/or imaging assembly 102 may take a variety of other forms and/or be utilized for a variety of other steps, features, or functions, as discussed further below.

The optical system 160 and/or imaging assembly 102 of assembly 126 may have its own processor or the like that is configured, programmed and adapted to monitor and/or control (independent of and/or in conjunction with processor 114) the operational characteristics or features of at least one component of system 100 (e.g., of assembly 126). In certain embodiments, optical system 160 and/or imaging assembly 102 of assembly 126 may have its own processor in communication with processor 114 and may make changes based on instructions received from processor 114 (or based on monitored characteristics of at least one sensor 116 of system 100).

As noted above and as shown in FIG. 3, particle processing system 100 includes at least one sensor assembly/member 116 that is configured and adapted to sense or monitor at least one operational characteristic or processing feature of system 100. In exemplary embodiments, system 100 includes a plurality of sensor assemblies 116a-"n". In certain embodiments and as shown in FIG. 2, system 100 includes a first sensor assembly 116a that is configured and adapted to sense or monitor at least one operational characteristic or processing feature of the particle delivery assembly 118, a second sensor assembly 116b that is configured and adapted to sense or monitor at least one operational characteristic or processing feature of the electromagnetic radiation source assembly 120, a third sensor assembly 116c that is configured and adapted to sense or monitor at least one operational characteristic or processing feature of the particle inspection region 122, a fourth sensor assembly 116d that is configured and adapted to sense or monitor at least one operational characteristic or processing feature of the particle collection assembly 124, and a fifth sensor assembly 116e that is configured and adapted to sense or monitor at least one operational characteristic or processing feature of the signal detector assembly 126. It is noted that system 100 may have any number of sensor assemblies 116a-"n" in communication with processor 114.

Exemplary processor 114 is configured to transmit and/or receive signals (e.g., command and status signals) or the like to and/or from sensor assemblies 116 and/or particle delivery assembly 118, electromagnetic radiation source assembly 120, particle inspection region 122, particle collection assembly 124 and/or signal detector assembly 126, in order to change the status and/or operating parameters of the components of system 100. In short, processor 114 is in communication with sensors 116 and/or the components of system 100 for control and/or communication purposes. As such, exemplary processor 114 is configured and adapted to enable or facilitate system 100 to process particles in an operatorless fashion based on the operational characteristics sensed by the sensor assemblies 116.

In general, sensor assembly 116a associated with particle delivery assembly 118 may be configured to sense or monitor at least one characteristic or feature of nozzle 132, nozzle orifice 134, oscillator 140, sample 146, sheath fluid 148 and/or the fluid delivery system (e.g., pumps, reservoirs, valves, tubing, etc.) of particle delivery assembly 118 so that processor 114 may monitor and/or change one or more parameters or characteristics of assembly 118 based on the sensed or monitored features to enable assembly 118 to operate in an operatorless fashion.

For example and without limitation, sensor assembly 116a associated with particle delivery assembly 118 may sense or monitor such exemplary characteristics or features of nozzle 132, oscillator 140, sample 146, sheath fluid 148 and/or other components of particle delivery assembly 118 and/or system 100 including: appropriate pressure levels, pump speeds, vacuum levels, sample 146 characteristics, sheath fluid 148 characteristics, waste status and control, stability, alignment adjustment issues, flow rates, identifications, durations, presence (e.g., of sample 146 and/or sheath fluid 148), insertion (e.g., of sample 146 and/or sheath fluid 148), removal (e.g., of sample 146 and/or sheath fluid 148), replacement and/or temperatures.

Likewise, sensor assembly 116b associated with electromagnetic radiation source assembly 120 may sense or monitor such exemplary characteristics or features of energy source 152 and/or other components of electromagnetic radiation source assembly 120/system 100 including, without limitation: appropriate power, intensity, beam size, wavelength, position, stability and/or motion.

Similarly, sensor assembly 116c associated with particle inspection region assembly 122 may sense or monitor such exemplary characteristics of droplets 138, stream 136 and/or other components of particle inspection region 122 and/or system 100 including, without limitation: monitoring the stream, monitoring drop formation, and/or determining sort timing.

Furthermore, sensor assembly 116d associated with particle collection assembly 124 may sense or monitor such exemplary characteristics of deflection plates 142, droplets 138, collection members 144 and/or other components of particle collection assembly 124 and/or system 100 including, without limitation: appropriate sort control (e.g., amplitude, charge, rate if charging, etc.), appropriate deflection, stream stability, non-spraying, direction, insertion (e.g., of members 144), identification, removal (e.g., members 144), level monitor (144, 146, 148), volume presence, optical alignment and/or position, time and/or duration, number of sorted drops, particles and/or cells, purity, yield and/or recovery.

Also, sensor assembly 116e associated with signal detector assembly 126 may sense or monitor such exemplary characteristics of detector assembly 156, controller 158, imaging assembly 102, optical system 160 and/or other components of signal detector assembly 126 and/or system 100 including, without limitation: alarms, progress, safety, instrument start-up, optical alignment, direction, position, and/or monitor and/or control functions.

In general, processor 114 is configured to monitor and adjust (e.g., automatically change) one or more parameters, features, characteristics and/or components of system 100 based on the one or more operational characteristics sensed by the one or more sensor members 116. As such, processor 114 is generally configured and adapted to enable or facilitate system 100 to process particles in an operatorless fashion.

In exemplary embodiments, other operational characteristics or features of the components of system 100 that may be monitored or sensed (e.g., via sensors 116) and/or run in an operatorless fashion (e.g., via processor 114 and sensors 116) may include, without limitation, the following:

(i) instrument start-up (e.g., power sources; electrical sources; laser sources (laser 152 may switched on automatically to ensure it has warmed up or reached equilibrium state prior to use, may be remotely controlled, or may be controlled based on some other condition); excitation sources; fluidics (sample 146, sheath 148); air/vacuum; pumps; detection system (assembly 156); processors/computers; sub-systems; safety mechanisms; self-tests; self-calibration; self-diagnose issues; self-identification of current state (e.g., readiness) for sorting; communication of status);

(ii) input sample (e.g., identification of input sample 146 (what is it for recording, traceability, acceptance, sequenced, measurement or sorting) and/or input sample vessel; presence of sample 146; quantity of sample 146 at any given time);

(iii) insertion of sample 146 (e.g., initial insertion of sample 146 to system 100 (from or within container); running (flow) or pausing of sample 146; regulation and/or control of sample flow and/or sample flow rate dynamically (periodically and/or to a set-point that is defined automatically or in advance during instrument set-up/manufacture/calibration); monitoring sample volume or level; monitoring event rate and altering sample pressure and/or expulsion rates to achieve a desired set-point for particle event (input) rate);

(iv) sort collection (e.g., vessel 144 insertion/removal; position of vessels 144 (waste, sorted fraction(s)) or of unitary cartridge; sealing of fluidic and/or other necessary connections required to enable system 100 operation; identification and/or selection of particles or particle populations of interest for measurement and/or sorting (the identification and/or location of sort gates on desired particle population); the automated placement of sort regions on or around live, suitably oriented or aligned, or other characteristics of cell populations or of other particles (e.g., identify live and dead populations, identify oriented or aligned fractions, apply conditioning such as data manipulation, rotation, translation, zoom, identify cell or other particle populations, create sort gate with suitable geometry to ensure desired purity, recovery, enrichment, efficiency and/or sort rate. Applying appropriate signal and/or electrical gain to move or maintain population within acceptable signal range, field of view, and/or region of interest);

(v) sort mode and/or automated adjustment or alignment of operating conditions (e.g., to enable predefined/user specified purity/efficiency and/or recovery/yield modes (event rate, gating schemes, sort rate, abort rate, peak to valley ratio, etc.); applying various data manipulation algorithms to calculate and/or automatically adjust data that may be visualized as a rotation or other translation function on one or more dimensions on data sets and/or on bivariate data plots to assist with the projection of data in histogram views; adjustment of parameters to bring particle population within acceptable signal limits to enable reliable measurement of particles or to enable certain data to be displayed visually (sensitivity/gain/position and/or photodetector amplification) using software/firmware or hardware (examples include adjust photodetector voltage and/or gain (until population is in desired location), optical alignment functions enabled (excitation source and/or associated optical and/or mechanical elements, flow chamber (particles), detectors) using particles/mimic particles or other optical schemes such as light sources/image processing/machine vision));

(vi) monitoring of particle clusters/populations and/or cluster positions based on certain data representations (e.g., monitor and then adjust data/sort region conditions or boundaries (tracking) to account for minor fluctuations in measured signal levels so that sorting (particle processing) may continue with minimal impact on sort purity and recovery);

(vii) adjusting a sort mechanism (e.g., sort monitor and/or drop monitor and/or side streams/calibration/timing and/or particle/drop trajectory and/or velocity and expected arrival at sort position/mechanism to enable reliable/reproducible/stable performance of particle separation to meet the desired outcome (such as given number of particles, purity, ratio, recovery, yield, characteristic property, homogeneity, heterogeneity, size, morphology, fluorescence, light scatter properties, DNA content, and the like));

(viii) adjusting optical measurement apparatus (e.g., through positioning various mechanical or optical components, or by effecting the direction or position of one or more optical paths or particle paths to enable reliable and consistent measurement and/or sorting of particles flowing within or associated with system 100);

(ix) monitor and control functions (e.g., system leaks (gas/liquid); out of bounds (power, safe shut-down, universal power supply, safety and control network, etc.); trending (e.g., sample quality, sort rate, sort fraction, assessment of live to dead ratio within a sample, scheduling of samples, alarm conditions and alarms); intelligent error handling such as self-fixing, self-regulation or other act such as by reacting to system 100 parameters (e.g., parameter change such as temperature, pressure, vacuum, alignment movement, etc.) that may affect system/instrument operation);

(x) alerts and/or alarms (e.g., alerts or alarms that caution device or user that system is nearing or operating outside acceptable limits/window; run and control fluids (sheath, waste, sample, sort fraction and trajectory of sort and non-sort fractions) level monitor and refill; cleaning lines; sample waste; etc.);

(xi) safety aspects (e.g., safety of environment or from environment of operator or sample or system/instrument); potential exposure of sample to the environment, the apparatus, and other samples; automated and/or robotic feeding of samples, such as sheath fluid(s) 148, sort output fractions, waste and other required fluids, consumables, calibration parts, cleaning supplies, etc. (e.g., systems/methods to enable continuous operation over extended periods (e.g., for different samples 146) without the need for human intervention);

(xii) remote-controlled features and/or operations (e.g., reduce requirement for operator to be in front of system 100, system 100 could be controlled from a remote location/room with respect to the system 100; remote-controlled features that may be particularly useful if there are concerns over sample contamination issues (between samples, or sample and system/environment, or sample and operator, as non-limiting examples), or concerns where pathogens, communicable diseases or the like or other human or non-human vectors are involved (e.g., Hepatitic C, Influenza strains, Malaria, H1N1, HIV, BSE, TB, etc));

(xiii) other aspects or features of system 100 (e.g., nozzle 132 alignment; laser 152 alignment; excitation source 152 alignment; detector 156 alignment; data manipulation for identification and zooming; population identification; population sort regions; set-point purity; etc.);

(xiv) auto-rotation (e.g., calculating and automatically adjusting data rotation on one or more bivariate plots to assist with projection of data in histogram views and related gating or sort strategies);

(xv) fluidic stability (e.g., monitoring droplet 138 break-off image and automatically adjusting amplitude and phase controls to maintain position and profile/shape at neck of last attached drop 138);

(xvi) sort timing (e.g., determine droplet 138 break-off without the need for user intervention);

(xvii) sample flow rate (e.g., monitoring event rate and controlling sample pressure to achieve a desired set-point for particle event rate);

(xviii) optical alignment of jet (e.g., image-based alignment of nozzle 132 and/or excitation source 152 to predefined position where image is adjusted with respect to expected conditions);

(xix) data-based alignment (e.g., data-based alignment of nozzle 132, excitation source 152 and/or detector 156 position using feedback from measured photodetector signals (e.g., from calibration or target particles; identify and locate sort regions around cell or other particle populations));

(xx) sort stream (e.g., determine droplet 138 deflection conditions such as position, fanning, charge timing, waste centering, etc.); and/or (xxi) event rate (e.g., monitoring event rate and controlling sample pressure to achieve a desired set-point for particle event rate).

Moreover, the processor 114 and sensor assemblies 116 of the present disclosure may be advantageously utilized to sense/monitor even other characteristics/aspects of system 100, including, for example, other characteristics/aspects disclosed and described in U.S. Pat. Nos. 8,277,764; 7,012,689; 6,372,506 and 6,248,590; and U.S. Patent Publication Nos. 2012/0200857 and 2012/0202237; each incorporated by reference herein in their entirety.

Figure 4:
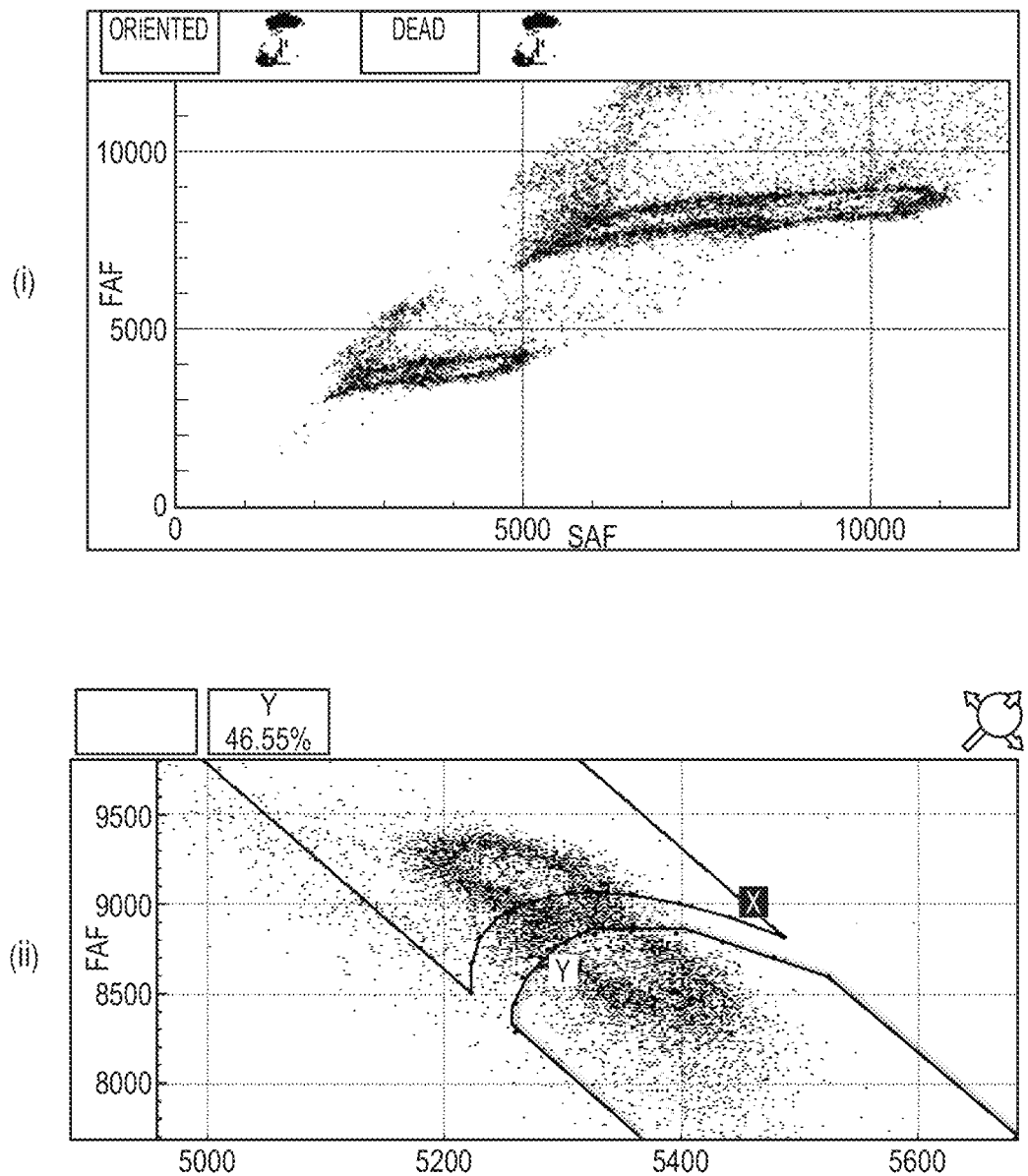

Exemplary Determination of Particle Sub-Populations:

In certain embodiments, system 100 may be configured to automatically determine one or more cell or particle sub-populations. Referring to FIGS. 4(i) and 4(ii), cell populations may be displayed, for example, on one or more bivariate plots (e.g., side scatter versus fluorescence; area versus peak; etc.). Previously, an operator would define a gating region that enclosed a cell sub-population of interest by drawing an enclosed region on the bivariate plot around a cell sub-population of interest. The gating region, for example, to define sub-populations for sorting, would be selected based on an understanding of the expected characteristics of the cell population and the experience of the operator in applying selection criteria to the expected characteristics of the cell population. Thus, for example, the cells of interest may be known reside in a region of the bivariate plot having strong side scatter signals and strong fluorescence signals. When a sub-population or cluster of cells exhibiting these predetermined characteristics could be discerned, the operator would draw a gate that would surround these cells. An experienced operator would select and draw the gating region to exclude unwanted cells and/or include desired cells. Should the gating region be drawn too broadly then unwanted cells may be undesirably included in the sorted sub-population. Should the gating region be drawn more specifically then purity of the sorted sub-population may be enhanced but yield may be undesirably decreased. Thus, the size, shape, orientation, perimeter, etc. of the gating region affect both the purity and the yield of the sorted sub-population.

In exemplary embodiments of system 100, cell sub-populations may be identified and/or gating regions may be automatically drawn based on measured or sensed characteristics of the cells and selection criteria. For example, a cell population may be identified based on a first characteristic, such as a light scatter or fluorescence signal. A first characteristic sub-population of cells may be identified as those cells having a first measured or sensed characteristic that satisfies a first selection criteria, e.g., predetermined upper and/or lower thresholds of this first characteristic. A statistical analysis of the first characteristic sub-population may be conducted to determine its distribution and/or other attributes of interest. The statistical analyses may be used to further refine the first characteristic sub-population of cells. The cell population may also be identified based on a second characteristic, such as a scatter or fluorescence signal. A second characteristic sub-population of cells may be identified as those cells having a second measured or sensed characteristic that satisfies a second selection criteria, e.g., predetermined threshold(s) of this second characteristic. A statistical analysis of the second characteristic sub-population may be conducted to determine its distribution and/or other attributes of interest. The statistical analyses may be used to further refine the second characteristic sub-population of cells. A combined sub-population of cells satisfying both the first selection criteria and the second selection criteria may be defined. A statistical analysis of the combined sub-population of cells may be conducted to determine its distribution and/or other attributes of interest. The statistical analyses of the combined sub-population of cells may be used to further refine the combined sub-population of cells. Optionally, third, fourth, etc. measured or sensed characteristics may be used identify sub-populations and/or refined the sub-populations.

A characteristic used to identify a particular sub-population of cells (or particles) may be provided as a number or a quantitative value (relative or absolute), as a percentage, as a difference, as a ratio, as a mathematical equation or algorithm, as a look-up table, as a statistical event, as a function of another characteristic, as a combination thereof, etc.

According to some embodiments, a particular sub-population of cells may be defined based on a first set of measured, sensed and/or determined characteristics of the cells satisfying a first set of selection criteria. As a non-limiting exemplary embodiment, a sub-population of cells may be defined as those cells having a scatter signal intensity above a predetermined scatter threshold and a fluorescence signal intensity above a predetermined fluorescence threshold. Upper thresholds may also be predetermined and applied as a condition for inclusion within the sub-population of cells. These predetermined thresholds may be absolute and/or relative values. For example, the predetermined scatter lower threshold may be set at a value equal to 70% of the side scatter range for the entire population.

The cells falling within this first sub-population, as determined using the first set of measured, sensed and/or determined characteristics, may then be subjected to a second set of measured, sensed and/or determined characteristics of the cells satisfying a second set of selection criteria so as to further be sub-grouped. As a non-limiting exemplary embodiment, a sub-grouping of the sub-population of cells may be defined as those cells having an area under a fluorescence signal above a predetermined area threshold and/or a peak fluorescence intensity signal value above a predetermined peak intensity threshold. Upper thresholds may also be predetermined and applied as a condition for inclusion within the sub-group of the sub-population of cells. These predetermined thresholds may be absolute and/or relative values. For example, the predetermined area lower threshold may be set to a value equal to the mean area of the fluorescence signal for the entire sub-population.

Thus, it is understood that selection of cell populations of interest may be a multi-step process using any of various measured, sensed and/or determined characteristics and predetermined threshold or other selection criteria.

According to certain embodiments, for a multi-channel particle processing system, the selection criteria for particles or cells flowing through any single micro-fluidic channel may be based on real-time data from other micro-fluidic channels in the particle processing system. Thus, for example, a selection criteria may require that a particle's signal fall within a standard deviation (or any other measurement criteria) of the mean of all particles flowing through the plurality of micro-fluidic channels that meet a lower threshold. This mean value may be calculated over a certain time interval, over a certain number of particle events, and/or a combination thereof.

Exemplary Determination of Gating Regions:

According to certain aspects, and referring to FIG. 4(ii), gating regions may be automatically defined around the sub-populations and/or sub-groups of cells. Predetermined gating selection criteria may be used to draw a gating region around the combined sub-population. For example, a gating region may be defined to include 100% of the combined sub-population. Optionally, a gating region may be defined to include that portion of the combined sub-population residing within two standard deviations of a mean of a measured, sensed, or determined characteristic of the sub-population. As a non-limiting example, a gating region may be drawn around that portion of a combined sub-population that falls with a range of fluorescence signal intensities centered on the mean fluorescence signal intensity and/or that falls with 2.5 standard deviations of the scatter signal.

Gating regions may be automatically defined around sub-populations or sub-groups of cells and may be adapted in real-time and/or may be updated periodically at regular intervals and/or when a gating update criteria is triggered.

In general, the predetermined gating selection criteria may be any selection criteria that assists in satisfying the purity and/or yield desired for the to-be-sorted population. The gating selection criteria may be set based on absolute signal values, based on relative signal values, based on statistical parameters, etc. for any individually identified sub-populations and/or for any combination of the individually identified sub-populations. The gating region selection criteria may be based on any measured, sensed, and/or determined characteristic(s) as may be reflected on characteristic versus time graphs, single variable histograms, bivariate plots, set thresholds (absolute and/or relative), statistical analyses thereof, and the like, and/or any combination thereof.

The actual gating region may be determined using any suitable mathematical algorithm. Thus, for example, the gating region may be a regular or irregular polygon, i.e., a region defined by a plurality of straight-line segments. Optionally, one or more segments of the perimeter of the gating region may be defined by a multi-ordered curve fit program. For example, where the to-be-sorted sub-population generally forms a circular or elliptical cluster based on the predetermined characteristics, a circular or elliptical gating region may be defined around the cluster. When the population to-be-gated is expected to assume a characteristic or signature shape, a predetermined gating shape may be applied. This predefined boundary shape may be located with respect to a center of mass of the particle sub-population and/or may be sized to encompass a predetermined percentage of the sub-population. Optionally, a portion or segment of the gating region's boundary may be provided as a segment having a predetermined shape or defined by a predetermined mathematical algorithm. A second-order curve may provide sufficient definition.

According to another aspect, gating regions may be defined around more than one cell sub-population. Thus, in certain embodiments, a first gating region may be defined around a cluster of cells that are to be sent to a first reservoir (e.g., a sort or keep chamber) and a second gating region may be defined around a cluster of cell that are to be sent to second reservoir (e.g., a waste chamber). In other embodiments, a first gating region may be defined around a cluster of cells to be subjected to a primary sorting operation, a second gating region may be defined around a cluster of cells that are to be subjected to a secondary sorting operation, and a third gating region or the absence of a gating region may be defined around a cluster of cells that are to remain unsorted. Alternatively, one or more gating regions may be used to identify and sort (i.e. reject) a cell population therefore enriching a cell population for those cells or particles that were not gated.

Each of these cell sub-populations may be independently identified according to predetermined selection criteria and measured, sensed and/or determined characteristics. Further, each of the cell sub-populations may be independently gated according to predetermined gating selection criteria. Independently identifying and gating cell sub-populations may provide a means of assuring the quality and confidence in the cell sub-population of interest. For example, identifying a second gated sub-population may be important if it is a prime concern to ensure that cells from the identified sub-population are not sorted with the primary gated sub-population (i.e., that the primary gated sub-population is not contaminated by cells from the second gated sub-population).

In some applications involving more than one independently-determined gating region, the gating regions may be substantially isolated from one other. However, in other applications, the independently-determined gating regions may lie adjacent one another and may even overlap. Thus, according to one aspect, when two clusters or gating regions of cell sub-populations (e.g., desired and undesired) have potential significant overlap, automatically determining a gating region for the desired cell sub-population may include defining a buffer zone between the two clusters.

In one example embodiment, one or both of the gating regions may be decreased until there is no overlap. Optionally, one or both of the gating regions may be decreased until there is a buffer zone or gap between the gating regions. The overall shape of the gating region may be maintained even as the size of the gating region decreases. Optionally, the adjacent side(s) of one or both of the adjacent gating regions may be pulled inward (i.e., away from the other gating region), while the remaining boundary portions of the gating regions remain stationary. In general, if maintaining the purity of the desired or primary gating region is important, then altering (i.e. increasing or decreasing) the primary gating region may be advantageous.

In another example embodiment, a common boundary between the two adjacent or overlapping gating regions may be determined. This common boundary may be provided as a line located equidistant from a center of mass of each of the cell sub-populations, as a line equidistance from two predetermined points on a plot of the cell sub-populations, as a predetermined shape or a predetermined mathematical algorithm, as a segment that is coincident with one of the boundary segments of one of the adjacent or overlapping gating regions, and/or as a segment equidistant between adjacent boundary segments of the two adjacent or overlapping gating regions, etc. Further, it can be seen that this common boundary may be shifted toward or away from either of the gating regions. For example, rather than being located equidistant (i.e., 50/50) from the center of mass of each of the cell sub-populations, the common boundary may be positioned more toward the center of mass of one of the sub-populations (e.g., a 60/40 or 70/30 or 80/20 split) than the other.

Additionally, according to certain embodiments, the commonly-defined boundary between the adjacent gating regions may be used to further isolate the gating regions. The common boundary may be split into two boundaries (each having the same shape of the common boundary) and moved apart (in parallel or along some other desired geometry) to create a buffer zone or gap between the two adjacent gating regions. This buffer zone or gap may extend over any percent of the distance between the centers of mass of each the gated cell sub-populations. For example, if the buffer zone is centered between the two gating regions, the percentage distances (from the center of mass to the first gating boundary/across the buffer zone/from the second gating boundary to the center of mass) may range from 50/0/50 to 45/10/45 to 40/20/40 to 35/30/35, etc. Further, as discussed with respect to the common boundary above, the buffer zone may be shifted toward or away from the primary gating region. Thus, by way of non-limiting example, the percentage distances may be split 30/30/40, 40/30/30, 50/20/30, 60/10/40, etc.

Operators are familiar with using histograms to confirm that the gated cell sub-populations are sufficiently distinct and/or isolated. When cell sub-populations are substantially isolated from one other, a histogram plot of the cells taken along an axis of the bivariate plot will display a so called high 'valley-to-peak' ratio. The more isolated the cell sub-populations, the deeper and wider the valley between cell populations. However, in some applications, the gating regions may lie adjacent one another and may even overlap (i.e., occupy a common portion of the characterizing landscape). In such cases a histogram plot of the cells taken along an axis of the bivariate plot may display a low valley to peak ratio and even, in some instances, may fail to clearly display any valley. A failure of such a histogram to display distinct peaks (or failure to display a sufficiently high valley to peak ratio) may be due to an actual overlap of the gating regions and/or may be due to the gated regions extending over the same data range charted by the histogram even though occupying distinct portions of the bivariate plot.

According to certain aspects, a histogram may be developed using the common boundary described above and plotting the normal distances of the cells from the common boundary. This may provide a visual verification that the gating region is properly defined.

According to even further aspects, automatically determining a cell sub-population and/or gating regions may be based on one, two, three, four, . . . "n"-dimensional cell data.
Exemplary Monitoring and/or Tracking of Particle Populations:

In exemplary embodiments, system 100 (e.g., via sensors 116 and processor 114) may be configured and adapted to track a cell population or populations for operatorless operation, and/or for sorting particles to account for varying operating conditions of system 100 (e.g., instruments and/or instrument component variations, varying environment around system 100, and/or variations between samples, as non-limiting examples). In general, particle populations (e.g., a grouping of cells that are considered similar), and/or cluster positions based on certain data representations, may be monitored, and the data and/or sort gate and/or region conditions or boundaries may then be adjusted (or "tracked") to account for minor fluctuations in measured signal levels so that sorting (particle processing) may continue with minimal impact on sort purity and recovery.

For example, in one exemplary system 100 region tracking algorithm, the algorithm adjusts the position of the active sort region (e.g., a sort gate) with respect to a particle population, as displayed on a bivariate data plot, in response to data from a Field Programmable Gate Array ("FPGA") or other suitable processor containing particle event information (e.g., light pulse characteristics that may include pulse height, width, area or other characteristics).

According to certain aspects, once a region is defined (whether by human or by machine/operatorless technique as described above) around some or all of a particle sub-population, the centroid of a tracked region may be calculated. A tracked region may apply to a population or sub-population of cells or particles to designate, track and/or monitor cells or particles, and may also be used for sorting purposes. As particles are processed, the center of mass for particle events in a set of current data packets (e.g., a specified amount of data for one or more particle events) from the processor may then be calculated. The specified number of particle events for each data packet may be preset. Further, the number of data packets included in a set may be adjusted to make the tracking more or less responsive. Next, the difference between the region's centroid and the particle events center of mass may be calculated.

In an exemplary embodiment, the following steps may then be performed by system 100: (i) the current centroid of the tracked region is calculated; (ii) for each new set of data packets from the processor, the current center of mass of the new or cumulative data is calculated; (iii) the difference between the current centroid of the tracked region and the current center of mass of the data is calculated; (iv) if the difference is above a defined threshold, this may indicate a so-called "sample boost" operation or some other unusual event of the sorter, and may not require moving the gating region; (v) if the difference is below a defined threshold, the gating region's position is adjusted by the difference; (vi) steps i through v are repeated. These steps may be performed in real-time, effectively tracking the data location and therefore particle or cell population.

With respect to step (ii) above, the center of mass may be calculated for the new set of data packets only, or the center of mass may be calculated for the cumulative particle data, and/or the center of mass may be calculated for certain subsets of the new data and/or the earlier acquired particle data. For example, the center of mass may be calculated based on the newly acquired data packet and a predetermined number of previously acquired data packets. The size of the data packets may be associated with the event rate. For example, a high event rate may limit the data packet to that data collected over only a few seconds of processing.

Optionally, other thresholds may be considered. For example, if the difference is below a lower threshold, the position of the sort region may be considered within the target zone and no adjustment may be made. Further, if the difference is above the upper threshold for a predetermined number of queries at step (iv), the gating region may be adjusted by the difference.

Further, the gating region may be tracked and/or adjusted using datum other than a centroid of the gating region and the center or mass of the data packets. By way of non-limiting example, if the height, width, shape, density, etc. of the population changes, the region may be expanded, contracted, reshaped, etc. to ensure inclusion of relevant events in the region.
Exemplary Droplet Break-off and/or Droplet Neck Thickness Monitoring:

The droplet break-off of droplets in particle processing systems might fluctuate for various reasons (e.g., temperature or sample effects) affecting the purity, thus requiring periodic attention by a human operator. Moreover, maintaining steady operation of conventional particle processing systems is a tedious task, and exceptions during operation of such systems might go unnoticed for some time.

Thus, according to even other aspects, system 100 (e.g., via imaging assembly 102 or the like) may be configured and adapted to monitor the droplet 138' break-off image and automatically adjust the amplitude and phase controls of the droplet generator to maintain the position and/or profile at the neck of the last attached droplet 138'.

In certain embodiments, system 100 is configured to maintain steady break-off point and neck thickness of droplet 138' via the adjustment of the Drop Drive Amplitude ("DDA") and the Drop Drive Phase ("DDP"). System 100 may also calculate and set-up the drop delay.

In exemplary embodiments of the present disclosure, system 100 assists a user by providing a real-time measurement, monitoring and adjustment of the break-off point and neck thickness of droplet 138'. The droplet break-off point and the droplet neck thickness may be controlled via real-time and or on-demand operatorless adjustment of the Drop Drive Amplitude ("DDA") and the Drop Drive Phase ("DDP") parameters.

A high speed camera may take pictures of droplet stream, including the droplet break-off point and/or the droplet neck region, as rapidly as between every microsecond and every 50 microseconds. The high speed camera may operate in phase or out of phase with the droplet formation signal or with a particular phase offset. Features extracted from the camera images of the fluid stream may include: edge detection, fluid stream features (e.g., thicknesses, wavelengths, droplet shape and position, neck geometry and position, aspect ratio, contrast, statistical characteristics such as means and standard deviation any parameter, etc. Further, images may be acquired at a lower frequency, but mimicking high speed acquisition through rapid lighting sequences in a synchronous or asynchronous fashion with droplet formation dynamics.

As a non-limiting example, the following steps may then be performed by system 100 in an operatorless fashion: (i) driving a stream with a droplet generator at a predetermined input oscillation frequency, amplitude and phase to form droplets; (ii) generating images of the droplet stream in the vicinity of a predetermined droplet breakoff point—these images are synchronized with the frequency of the droplet generator; (iii) comparing sequential images of the stream (i.e., compare sequential pixel counts associated with the stream width at a fixed z-axis location (i.e., along the length of the stream) to determine if the sequential pixel counts are changing or remaining substantially the same; (iv) stabilizing the images of the stream, if necessary, by adjusting the frequency of the image generator until pixel counts associated with the fixed z-axis location are substantially constant; (v) determining a z-axis "zero" location where the width of the stream first goes to zero (i.e., where the pixel count of the image of the width of the stream is zero); (vi) repeating step (v) and calculating a "zero" location difference between the sequentially determined z-axis "zero" locations; (vii) adjusting the DDP to reduce or eliminate the "zero" location difference; (viii) determining a "neck" width where the width of the stream first achieves a local minimum above the z-axis "zero" location by comparing stream width pixel counts at adjacent z-axis stations; (ix) repeating step (viii) and calculating a "neck" width difference between the sequentially determined "neck" widths; (x) adjusting the DDA to reduce or eliminate the "neck" width difference; and (xi) repeating steps (iii) to (x). With respect to step (v), the width of the stream goes to zero right below the last attached droplet 138'. With respect to step (vi), the local minimum immediately above the z-axis "zero" location corresponds to the droplet breakoff point. These steps may be performed in real-time, effectively maintaining the fluid stream in a constant configuration and eliminating fluctuations or variability in the droplet formation without requiring operator intervention. Other algorithms, including variations of the above-disclosed algorithm, may be used to maintain the droplet breakoff point at a fixed station.

Figure 5:
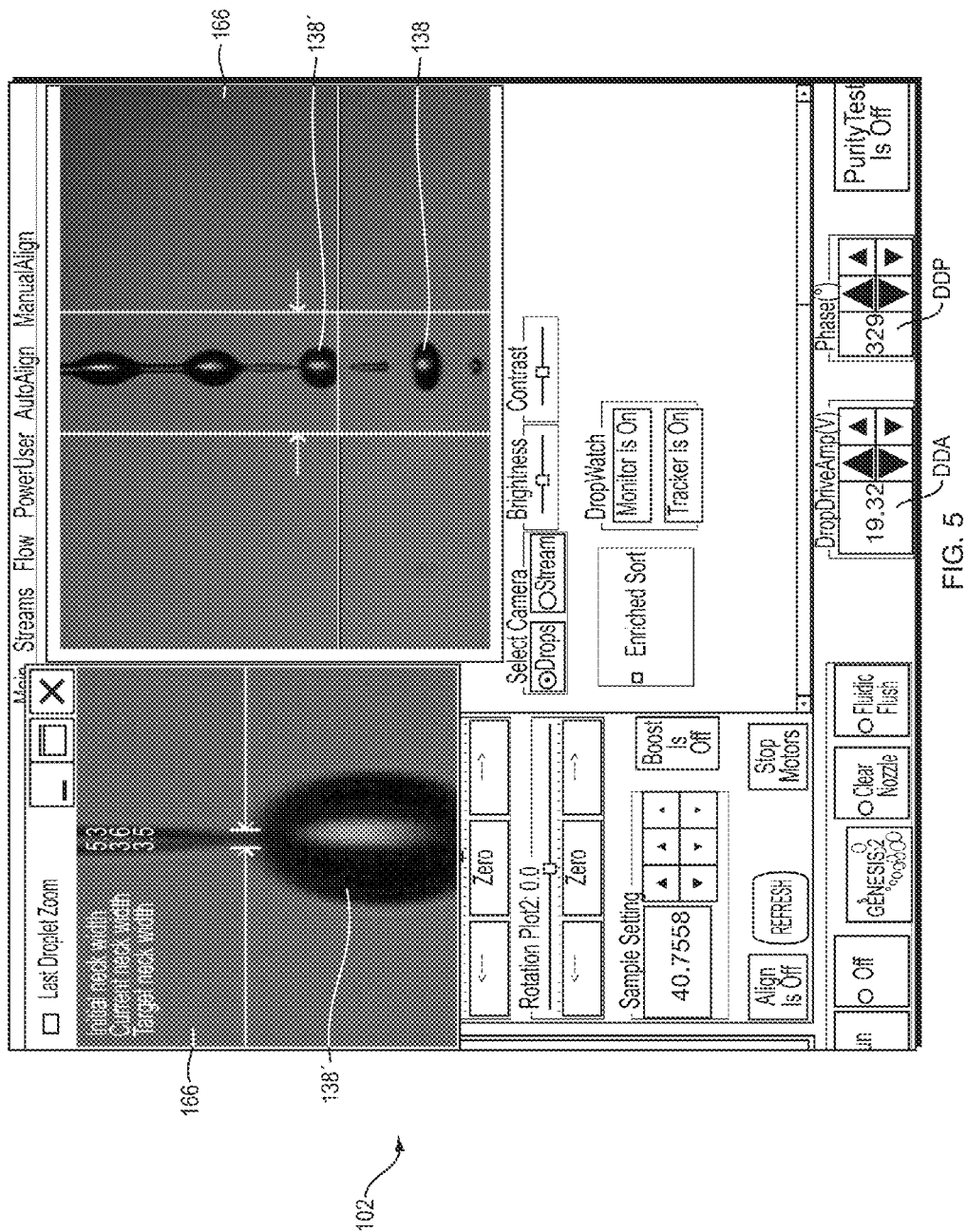
FIG. 5 depicts a screenshot from an exemplary fluidic stability monitor of the system of FIG. 3.

FIG. 5 depicts a screenshot from an exemplary droplet break-off monitor associated with system 100. In exemplary embodiments, the operatorless monitoring of the droplet break-off and/or neck thickness of system 100 allows the break-off point and/or neck thickness targets of droplet 138' to be set, and automatically adjusts the DDA and/or the DDP when required. Exemplary droplet break-off monitoring of system 100 may include spreadsheet ready files, and may include plotting neck thickness versus time and/or break-off point versus time. FIG. 5 shows a zoomed-in view of the jet and neck thickness at the last attached droplet 138'.

Exemplary Drop Delay Monitoring:

In particle processing systems, the time between detection of a particle (or cell) in a detection zone and charging of a droplet containing that detected particle (i.e., the drop delay) might fluctuate for various reasons (e.g., temperature, pressure, sample characteristics, etc.), thus requiring periodic attention by a human operator. Thus, according to even other aspects, system 100 (e.g., via imaging assembly 102 or the like) may be configured and adapted to automatically monitor and/or calculate the drop delay. Based on the operatorless real-time determination of drop delay, a charge may be applied to the last attached droplet 138'.

In certain embodiment of a particle processing system 100, a fluid stream may be perturbed into droplets by an oscillator (i.e., a droplet generator) as the stream exits an orifice. Typically, after exiting the nozzle or orifice, the fluid stream exhibits increasingly pronounced undulations and/or decreasing neck thicknesses in a downstream direction until a break-off point is reached where droplets break away from the fluid stream. The break-off point is defined as the last point at which a droplet contacts the fluid stream, and thus, this location represents the last point in time a charge may be applied to a droplet to effect a net retention of charge on a droplet for subsequent electrostatic deflection. The appropriate time to apply this charge is known as the drop delay. Typically, the drop delay is calculated or determined from the time at which a particle is detected. As droplets may be formed at a rate of between about 20,000 per second and 200,000 per second, the drop delay must be very precisely calculated. After the application of charge and break-off, the droplets may pass through an electromagnetic field produced by deflection plates. Thus, the charge applied to each droplet determines which path the droplet will follow and which collection container or other location and/or object it will fall into or on.

In exemplary embodiments, system 100 is configured to automatically calculate and set-up the drop delay based on a real-time measured stream fluctuation. In other word, droplets may be charged based on (i) a time of particle detection in the detection zone; (ii) a distance between the particle detection zone and the droplet break-off location; and (iii) the real-time measurement and determination of the time for the stream to traverse this detection-zone to break-off distance.

As a non-limiting example, the following steps may be performed by system 100 in an operatorless fashion: (i) driving a stream with a droplet generator at a predetermined input oscillation frequency, amplitude and phase to form droplets; (ii) generating at least one image of the droplet stream so as to encompass at least one undulation between the detection zone and the break-off point; (iii) determining a characteristic undulation length of the stream (e.g., determine pixel counts associated with a distance between adjacent local minimums (i.e., necks) of the undulating stream and/or determine pixel counts associated with a distance between adjacent local maximums (i.e., droplet maximum diameters) of the undulating stream); (iv) calculating a characteristic speed of the stream based on the determined characteristic undulation length and an characteristic oscillation frequency associated with the droplet generator; (iv) calculating time for the stream to travel from the detection zone to the break-off point based on the determined instantaneous speed of the stream and a determined distance between the detection zone and the break-off point. The determined distance between the detection zone and the break-off point may be: provided as an input; determined based on stream characteristics and measured oscillation frequency and/or phase; determined based on instantaneous real-time calculation of the stream's "zero" location and/or "neck" location, as presented above; etc.

According to some embodiments, the multiple images may be taken and each (or select) images may be used to determine an instantaneous undulation length of the stream. The instantaneous undulation length in conjunction with an instantaneous oscillation frequency associated with the droplet generator may be used to calculate an instantaneous speed of the stream. The delta time between the examined images in conjunction with the calculated instantaneous speed of the stream may be used to determine a delta distance traveled by the stream between images. The drop delay may be calculated by dividing the distance between the detection zone and the break-off point by the delta distance (i.e., the distance traveled between images) and then multiplying the delta time (i.e., the time between images) by this ratio. Optionally, a series of multiple images may be examined, and multiple delta times and associated delta distances may be repeatedly determined to account for variations in the speed of the stream during a drop delay time span. A high resolution imaging element may be used in conjunction with high speed data acquisition and processing (e.g., using a field programmable gate array) in order to take multiple images of the stream and to determine the precise distances traveled between image capture. The drop delay may be instantaneously determined on a droplet-by-droplet basis. Other algorithms, including variations of the above-disclosed algorithms, may be used to determine drop delay without requiring operator intervention.

First Exemplary Alignment Algorithm:

In exemplary embodiments, the alignment of system 100 (e.g., via sensors 116 and processor 114) may be accomplished in the presence or absence of particles. In general, the optical measurement devices of system 100 may be adjusted (e.g., via sensors 116 and processor 114) by positioning various mechanical and/or optical components, or by effecting the direction or position of one or more optical paths or particle paths to enable reliable and consistent measurement and/or sorting of particles flowing within system 100.

Basic alignment of the excitation energy source 152, the detectors, and optical components in the excitation beam path, and optical components in the collection beam path may be performed during assembly of the system 100. These alignment positions may be locked in or may be used as nominal positions for any further adjustment using translational and/or rotational stages.

For example, the position of excitation energy source 152 may be altered at the measurement point (e.g., by altering the position of source 152 and/or mirrors or lenses associated with source 152). The position of nozzle 132 and/or particle inspection region 122 may also be altered. Additionally the position of detectors of detector assembly 156 may be altered (one or more of these detectors may be fixed and others may move around such fixed components).

An automated alignment of a stream (with or without samples, target particles, calibration beads, etc.) may then be performed. This stream alignment may utilize translational and/or rotational positioning of the stream so that the intersection of the stream with the optical path extending from the excitation energy source 152 to the detector assemblies is optimized. In a preferred embodiment, the stream-forming element, e.g., nozzle 132 may be moved along three translational axes. Additional adjustment degrees of freedom may be utilized if desired.

For example, the positions of these components may be altered based upon an open loop that uses machine vision or the like, and/or based upon a closed loop that may use feedback from signal signature, e.g., image-based alignment of nozzle 132 and/or excitation source 152 to a pre-defined position where an image is adjusted with respect to expected conditions at which point a user may take control to fine-tune system 100 if desired, and/or data-based alignment of nozzle 132, excitation source 152 and/or detector positions using feedback from measured photodetector signal (e.g., from calibration or target particles).

Finally, according to certain embodiments, in a fine-tuning alignment procedure, using feedback from a photo-detector signal based on illumination of the sample, particles, beads etc. with the excitation energy source 152, one or more components of a signal collection and/or transmission path(s) for a sample's emitted signal (e.g., using calibration or target cells/particles) may be physically adjusted to optimize the signals received by the photodetector. For example, a calibration sample may be run and one or more components along the collection and transmission paths may be physically tweaked or fine-tuned to optimize the reception of the various signals (scatter, fluorescence, etc.) by the detector assemblies. Motorized adjustment stages (translational and/or angular axes) may be controlled based on signals received by the detector assemblies and analyzed by the electronics.

As a non-limiting example, the scatter signal may be fine-tuned so that a scatter histogram would show distinct peaks and valleys and/or the peak-to-valley ratio would be maximized. Such physical fine-tuning of the collection/transmission path typically may be accomplished by translating and/or rotating optical elements within the collection/transmission path. For example, the detector assembly may be moved laterally (side-to-side and/or up and down) to the beam path so as to ensure that the signal intensity is maximized.

These stream alignment and/or full alignment sequences may be executed each time a particle analysis and/or sorting process is performed. Alternatively, a conditional and/or adaptive alignment algorithm may be provided. As an example embodiment, parameters of previous runs may be compared to threshold parameters to determine if an alignment sequence should be performed. Parameters may include environmental conditions (e.g., temperature, humidity, pressure, etc., and changes thereof); operational conditions (e.g., time between runs, number of runs since last alignment, machine updates (software, firmware and/or hardware), user experience, user identification, etc., and changes thereof); sample conditions (e.g., sample batch or lot, sample protocols, sample age, sample uniqueness, etc., and changes thereof); run conditions (e.g., desired purity, yield, flow rate, sort rate, etc., and changes thereof); and anomalies in past runs (e.g., clogs, unexpected data, etc.). Comparing certain predetermined parameters to predetermined fine-tuning criteria and/or thresholds may trigger an instruction to perform a fine-tuning alignment procedure or a portion thereof. Comparing the same or other predetermined parameters to predetermined operational criteria and/or thresholds may trigger an instruction to perform an operational alignment procedure or a portion thereof, followed by a fine-tuning alignment procedure or portion thereof. Thus, depending upon the extent to which conditions have been altered or have not been altered, there may be no need to perform any alignment sequence. Such a conditional and/or adaptive alignment algorithm may reduce the amount of time a stable processing system spends in alignment mode.

Second Exemplary Alignment Algorithm:

According to certain aspects, system 100 may be fully aligned without requiring a sample (or other calibration particles) to flow through the detection region. In other words, system 100 may be aligned without using feedback from a photodetector receiving an emitted signal from a set of excited calibration or target particles. This may be referred to as a streamlined or reduced alignment algorithm.

In a non-streamlined or full alignment procedure, using feedback from a photodetector signal, the components of a signal collection and/or transmission path(s) for a sample's emitted signal (e.g., using calibration or target cells/particles) may be physically adjusted to optimize the signals received by the photodetector. For example, in the past, a calibration sample may have been run and the collection and transmission paths may have been physically tweaked or fine-tuned to optimize the reception of the various signals (scatter, fluorescence, etc.) by the detector assemblies. Thus, additional adjustment stages (translational and/or angular axes) would have been necessary to move/adjust one or more of the optical elements in the emitted signal collection/transmission path. As a non-limiting example, the scatter signal may have been fine-tuned so that a scatter histogram would show distinct peaks and valleys and/or the valley to peak ratio would be maximized. Such physical fine-tuning of the collection/transmission path typically requires several additional stages and would take anywhere from ten to fifteen minutes, even when automated. This full alignment sequence may be executed each time a particle analysis and/or sorting process is performed.

This fine-tuning alignment of system 100 may be eliminated in the streamlined or reduced alignment algorithm.

In an exemplary embodiment, the physical alignment of system 100 may be accomplished using only two steps. In a first step, the excitation energy source 152 may be physically aligned to a detector assembly 156 when the system 100 is first assembled. In a second step, the position of nozzle 132 and/or particle inspection region assembly 122 may also be adjusted with respect to the excitation energy source 152 using three translational stages (X, Y and Z). This may be an image-based physical alignment of nozzle 132, which may be automated as described above. These two alignment steps do not require the presence of detectable sample (e.g., calibration beads, cells, particles, etc.).

Thus, according to certain embodiments, post-assembly alignment of the particle detection subsystem (i.e., an excitation energy source 152, an excitation energy source optical assembly, a detector assembly 156, a signal collection optical assembly (or assemblies), and the nozzle 132) may be accomplished with only three relative translations. During assembly, the excitation energy source 152, the excitation energy source optical assembly, the detector assembly 156, and the signal collection optical assembly may be aligned and then locked down. Post-assembly and prior to processing a sample (or calibration beads), the nozzle 132 may be moved in the X, Y and/or Z directions in order to aligned the sample stream in the path of the excitation beam. No further physical movement or adjustment of the elements or components comprising the particle detection subsystem needs to be performed.

Thus, advantageously, the components comprising the excitation energy source 152, the excitation energy source optical assembly, the detector assembly 156, and the signal collection optical assembly do not require adjustable mounting stages.

Optionally, even if adjustable mounting stages are provided for one or more of the components comprising the excitation energy source 152, the excitation energy source optical assembly, the detector assembly 156, and the signal collection optical assembly, an alignment algorithm involving these adjustable mounting stages need not be invoked after the sample stream is located within the excitation beam and/or prior to every particle processing run.

According to certain embodiments, a data-based signal manipulation may be used to fine-tune the data collection, thus eliminating the need to physically adjust the collection and/or transmission paths of a sample's emitted signal (e.g., using calibration or target cells/particles) to optimize the signals received by the photodetector. In other words, the sample's emitted signal (e.g., side scatter, fluorescence, etc.) in a potentially less-than-optimal condition may be received by the detector assembly 156 and automatically analyzed to identify target sub-populations, identify non-target sub-populations, determine gating regions and/or conduct sorting operations. As described above with respect to the determination of particle clusters/sub-populations and/or gating regions, sub-populations of particles or cells emitting less than optimal side scatter signals may still be identified and gated with confidence that the desired cells are being captured with the desired purity and yield. Thus, the physical fine-tuning of the collection/transmission path of the sample's emitted signal may be eliminated.

EXAMPLE II

Microfluidic Flow Sorter Particle Processing System

Figure 6:
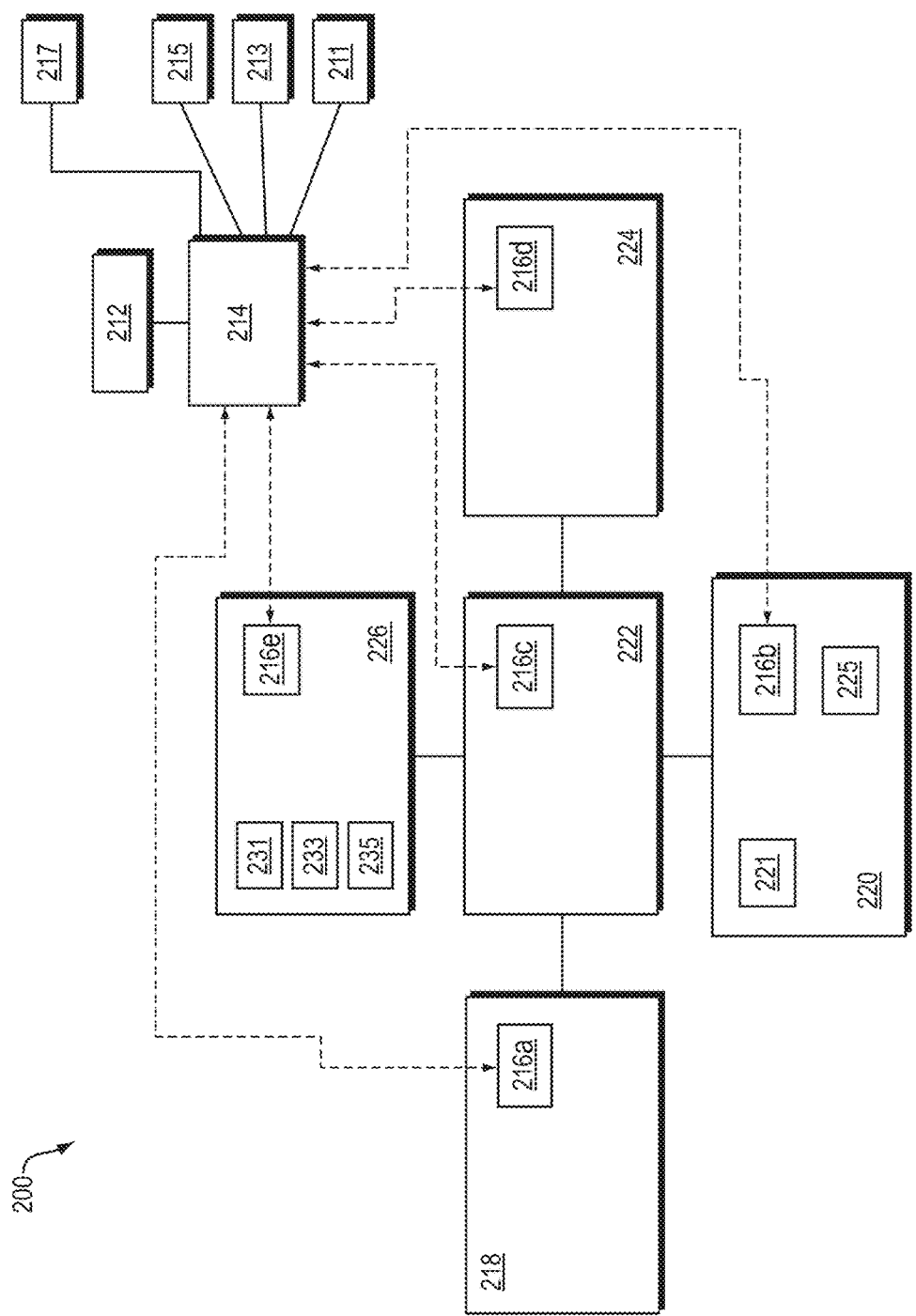
FIG. 6 is a block diagram of another exemplary embodiment of a particle processing system according to the present disclosure.

Referring now to FIG. 6, there is illustrated a block diagram of another exemplary embodiment of a particle processing system 200 according to the present disclosure. Similar to systems 10 and 100, particle processing system 200 is configured, dimensioned and adapted for analyzing, sorting, and/or processing (e.g., purifying, measuring, isolating, detecting, monitoring and/or enriching) particles (e.g., cells, microscopic particles, etc.) or the like, and wherein human intervention is not required and/or is minimized.

For example, system 200 may be a cytometer and/or a cell purification system or the like, although the present disclosure is not limited thereto. In exemplary embodiments, system 200 is a microfluidic flow sorter particle processing system 200 (e.g., microfluidic chip based system) or the like. Exemplary microfluidic flow sorter particle processing systems/components or the like are disclosed, for example, in U.S. Pat. Nos. 8,277,764; 8,123,044; 7,569,788; 7,492,522 and 6,808,075; U.S. Patent Publication Nos. 2012/0009025; 2012/0277902; 2011/0196637 and 2009/0116005; and U.S. Patent Application Ser. Nos. 61/647,821 and 61/702,114, the foregoing being incorporated herein by reference in their entireties.

Similar to systems 10 and 100 and as shown in FIG. 6, system 200 includes at least one processor 214 (e.g., a central automation processor or master processor). At least one display device 212 is in communication with processor 214. Processor 214 may also be in communication with (e.g., one or a plurality of) keypads and/or user stations 211, third-party devices 213 and/or additional processors and/or controllers 215. Processor 214 is generally capable of communication with a network or internet 217, and capable of sending and/or receiving audio, video and/or data or the like.

System 200 includes a microfluidic assembly 218, the microfluidic assembly 218 in communication with a particle inspection region assembly 222. System 200 also includes an electromagnetic radiation or light source assembly 220, a particle collection assembly 224 and an optical detector assembly 226. Processor 214 is in communication with microfluidic assembly 218, electromagnetic radiation source assembly 220, particle inspection region assembly 222, particle collection assembly 224 and/or an optical detector assembly 226.

Similar to systems 10 and 100, particle processing system 200 includes at least one sensor assembly/member 216 that is configured and adapted to sense or monitor at least one operational characteristic or processing feature of system 200 (e.g., sense at least one characteristic of microfluidic assembly 218, electromagnetic radiation source assembly 220, particle inspection region assembly 222, particle collection assembly 224 and/or an optical detector assembly 226). Each sensor assembly 216 is in electrical communication with processor 214, and system 200 may include a plurality of sensor assemblies 216a-"n".

It is to be noted that system 200 may include a plurality of assemblies 218, 220, 222, 224 and/or 226, and/or a plurality of processors 214 and sensors 216. Further, microfluidic assembly may include a plurality of microfluidic channels.

In general, processor 214 is configured to change (e.g., automatically change) one or more parameters, features, characteristics and/or components of system 200 based on the one or more operational characteristics sensed by the one or more sensor members 216. As such, processor 214 is generally configured and adapted to enable or facilitate system 200 to process particles in an operatorless fashion.

Processor 214 is generally configured to transmit and/or receive signals (e.g., command and/or status signals) or the like to and/or from sensor assemblies 216 and/or microfluidic assembly 218, electromagnetic radiation source assembly 220, particle inspection region assembly 222, particle collection assembly 224 and/or an optical detector assembly 226, in order to change the status and/or operating parameters of microfluidic assembly 218, electromagnetic radiation source assembly 220, particle inspection region assembly 222, particle collection assembly 224 and/or an optical detector assembly 226. Stated another way, processor 214 is in communication with sensors 216 and/or the components of system 200 for control and/or communication purposes.

For example, processor 214 may send command signals to a sensor assembly 216 associated with microfluidic assembly 218 (and/or directly to microfluidic assembly 218) to control or change the status or operating parameter of microfluidic assembly 218. Moreover, processor 214 may receive status signals from sensor assemblies 216 regarding the status of the components of system 200.

Each sensor assembly 216 may include or be associated with a local processor and/or processing unit (e.g., signal processing and/or control unit) or the like. As such, each sensor assembly 216 may be in communication with at least one component (e.g., assembly 218) of system 200 for control and/or communication purposes (e.g., independent of and/or in conjunction with processor 214). For example, the processor or processing control unit local to and/or associated with each sensor assembly 216 may send command signals directly to a component (e.g., assembly 218) of system 200 to control or change the status or operating parameter of that component.

Such command signals may or may not be directed from processor 214, and can be communicated to and/or from processor 214, although the present disclosure is not limited thereto. In exemplary embodiments, each assembly 218, 220, 222, 224 and/or 226 can include a processor or the like that can operate independent of and/or in conjunction with processor 214 for control and/or communication purposes associated with the components of system 200.

In general, processor 214 and/or sensors 216 are configured to enable system 200 to process particles in an operatorless fashion based on the operational characteristics sensed by the sensor assemblies 216. System 200 may have any number of sensor assemblies 216 in communication with processor 214.

Figure 7:
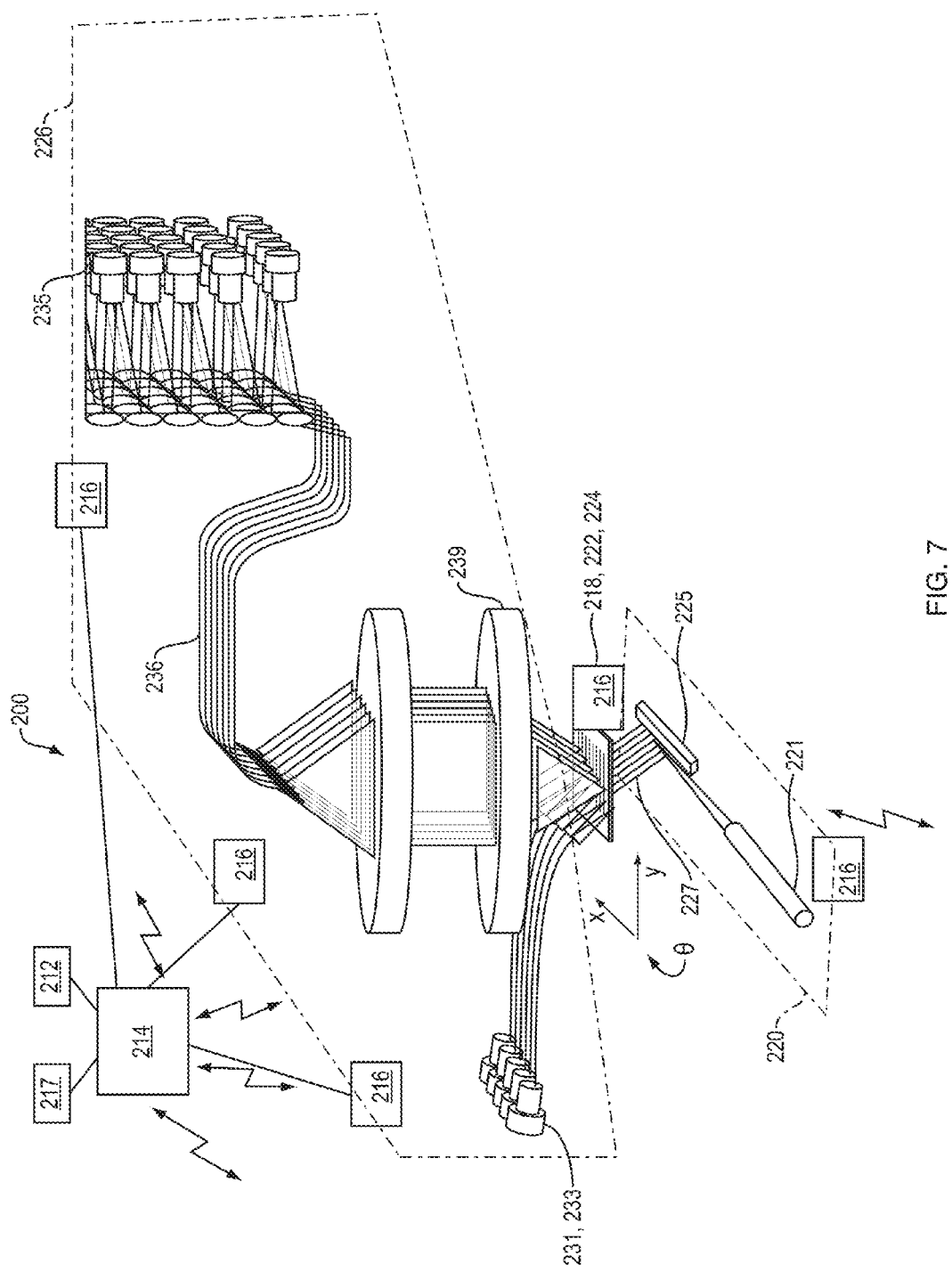
FIG. 7 illustrates an exemplary particle processing system of FIG. 6.

Turning now to FIG. 7, an example of a microfluidic flow sorter particle processing system 200 or the like is illustrated, although the present disclosure is not limited thereto. Rather, it is noted that the systems and methods described may be applied to other particle processing systems.

Figure 8:
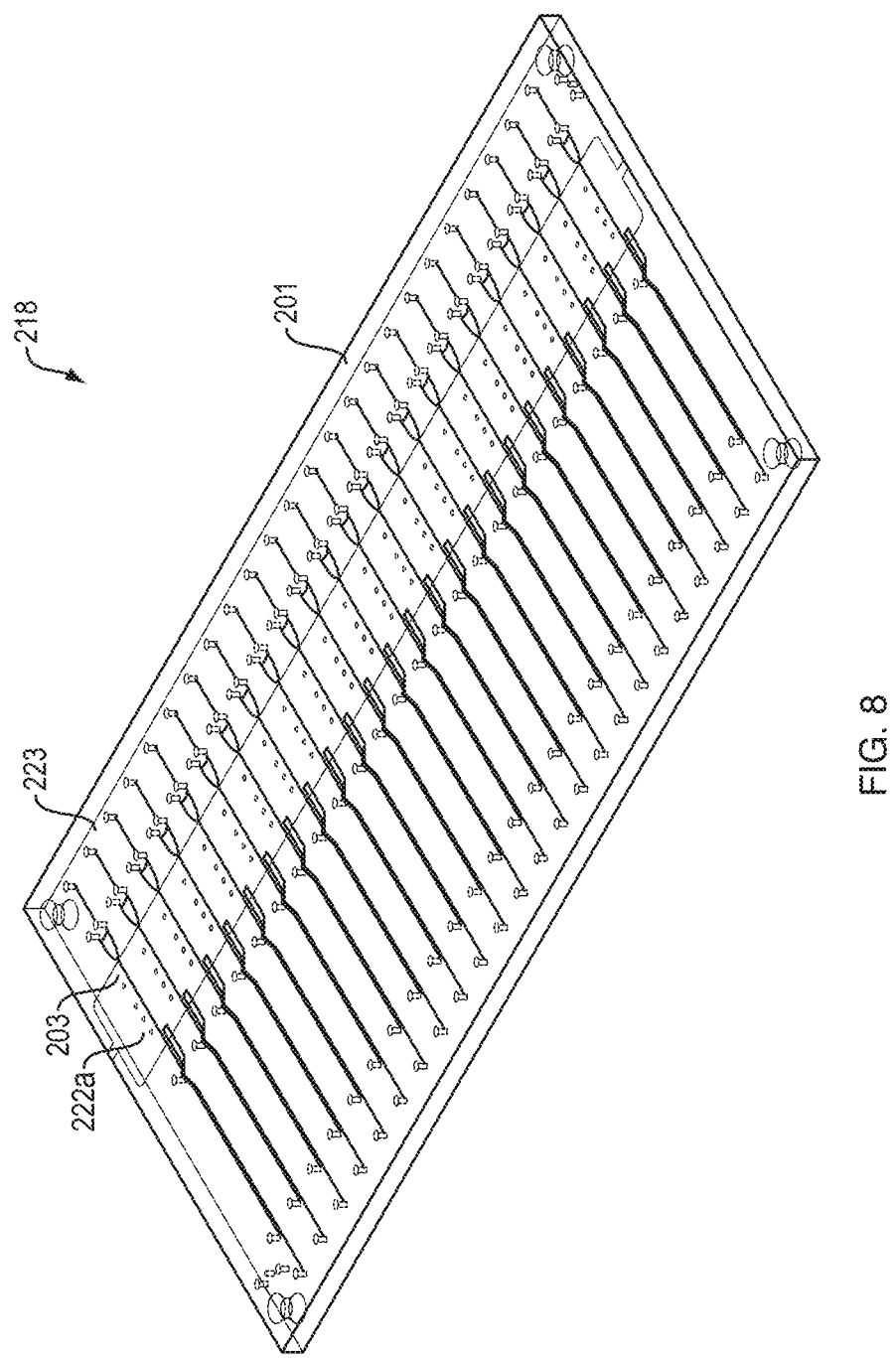
FIG. 8 illustrates an exemplary microfluidic assembly of the present disclosure.

FIG. 7 illustrates a system 200 suitable for implementing an illustrative embodiment of the present disclosure. As shown in FIGS. 7-8, system 200 includes a microfluidic assembly 218 (e.g., microfluidic chip). Assembly 218 includes a plurality of channels 203 for conveying a substance, such as particles or cells, therethrough. As discussed below, microfluidic assembly 218 includes and/or is communication with a particle inspection region assembly 222 and a particle sample fluid input region 223.

As shown in FIG. 8, microfluidic assembly 218 generally includes a substrate 201 having a plurality of channels 203 (e.g., microchannels) disposed therein. The channels transport fluid and/or particles through the assembly 218 for processing, handling, and/or performing any suitable operation (e.g., on a liquid sample). Assembly 218 may include any suitable number of microchannels 203 for transporting fluids through assembly 218.

In exemplary embodiments, an optical detector assembly 226 (FIG. 7) for use with microfluidic assembly 218 is provided. At least a portion of optical detector assembly 226 may be implemented in particle inspection region assembly 222 to interrogate the particles in this region. At least a portion of optical detector assembly 226 may monitor flow through a plurality of channels 203 simultaneously. In exemplary embodiments, assembly 226 can inspect individual particles for one or more particular characteristics, such as size, form, fluorescence, optical scattering, as well as other characteristics. It is noted that assembly 226 is not limited for use in particle or cell sorting systems and may be implemented in any suitable system having a substance, such as particles, to be monitored flowing through one or more channels.

FIG. 7 illustrates an overview of an optical detection assembly 226, which may be implemented for use with microfluidic assembly 218. However, assembly 226 may be implemented in any suitable system and is not limited for use with microfluidic assembly 218.

System 200 also includes electromagnetic radiation source assembly 220. In certain embodiments, electromagnetic radiation source assembly 220 includes one or more electromagnetic radiation or light sources 221 (e.g., a laser source(s) or the like) coupled to and/or in communication with beam shaping optics 225 (e.g., segmented mirror/ mirrors or the like, flat top elements, and/or other optical elements) for producing and forming one or more beams of electromagnetic radiation (e.g., light) 227 that pass through an optical mask 229 (FIG. 9), illustrated as an array of pinholes 229*a*, 229*b* (FIG. 9) aligned with an array of particle conveying channels 203 in the microfluidic chip assembly 218.

The electromagnetic radiation 227 admitted by the pinholes subsequently passes through the conveying channels 203 themselves. The portion of electromagnetic radiation beam 227 admitted to each channel 203 via one or more associated pin holes intersects particles that are conveyed through the channel 203 to create optical signals. Examples of optical signals that can be produced in optical particle analysis, cytometry and/or sorting when a beam 227 intersects a particle include, without limitation, optical extinction, angle dependent optical scatter and fluorescence. Optical extinction refers to the amount of electromagnetic radiation or light that a particle extinguishes, absorbs, or blocks. Angle dependent optical scatter refers to the fraction of electromagnetic radiation that is scattered or bent at each angle away from or toward the incident electromagnetic radiation beam. Fluorescent electromagnetic radiation is electromagnetic radiation that is absorbed by molecules in the particle and re-emitted at a longer wavelength.

In exemplary embodiments, detector optics including, for example, an optical extinction detection subsystem 231, optical scatter detection subsystem 233, and fluorescence detection subsystem 235 of optical detector assembly 226, which in some embodiments are located on an opposite side of the channels 203 from the electromagnetic radiation source assembly 220, capture and observe the optical signals generated by the intersection of an electromagnetic radiation beam with a particle in a channel 203. In certain embodiments, optical extinction detection subsystem 231 are placed directly opposite the electromagnetic radiation source 221 and aligned with the incident electromagnetic radiation path 227 for detecting optical extinction. Optical scatter detection subsystem 233 may be placed substantially perpendicular to the incident electromagnetic radiation path 227 in the plane formed by the incident light vector and the microfluidic channel it intersects. Alternatively, optical scatter detection subsystem 233 may be placed substantially perpendicular to the microfluidic chip substrate. A fluorescence detection subsystem 235 captures optical signals from particle fluorescence. The fluorescence detection subsystem 235 may include a large high numerical aperture lens 239 and/or other accompanying optical elements. As shown, the fluorescence detection subsystem 235 is placed above the microfluidic chip 218 to capture as many fluorescent photons as possible and image them onto detector 235. A fiber array 236 extends from the image plane and conveys signals to detector 235 for analyzing the signal. The detectors 231, 233, 235 may be photomultiplier tubes, photodiodes, avalanche photodiodes, a camera(s) or other suitable devices.

Electromagnetic radiation source assembly 220 and optical detector assembly 226 are implemented in an interrogation area or particle inspection region assembly 222 of the chip 218. In general, any suitable number of channels 203 may be observed using system 200.

Figure 9:
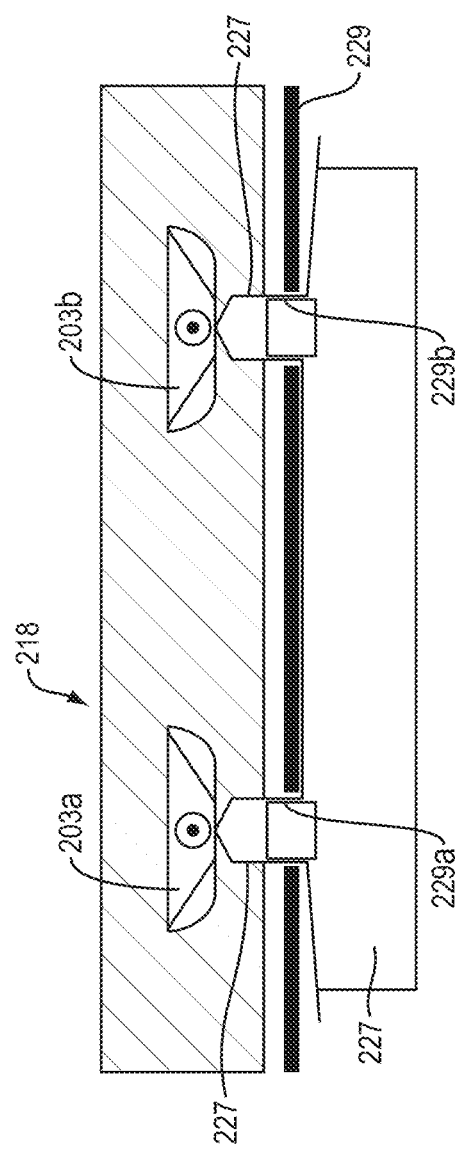
FIG. 9 illustrates a cross-section through channels of an exemplary microfluidic assembly of the present disclosure.

FIG. 9 shows an illustrative picture of the cross section through a portion of a microfluidic chip 218 containing a pair of microchannels 203*a* and 203*b*. The cross-section is in a plane that cuts through the microchannels and the pinholes 229*a*, 229*b* of the mask 229. The incident electromagnetic radiation 227 is partly blocked by the pinhole layer 229 and narrows the initial beam 227 to focused beams defined by each pinhole 229*a*, 229*b*. The focused beams intersect each channel to illuminate the region in which particles are permitted to flow in a core flow.

According to some embodiments, stray electromagnetic radiation may be blocked by the pinhole layer 229, which may be a separate part from the microfluidic chip 218 or may be fabricated on the surface of the chip 218 by suitable methods (e.g., photolithography).

As noted above and as shown in FIGS. 8-11, particle processing system 200 includes at least one sensor assembly/member 216 that is configured and adapted to sense or monitor at least one operational characteristic or processing feature of system 200 (e.g., sense at least one characteristic of microfluidic assembly 218, electromagnetic radiation source assembly 220, particle inspection region assembly 222, particle collection assembly 224 and/or optical detector assembly 226). As shown in FIGS. 8-11, exemplary system 200 includes a plurality of sensor assemblies 216*a*-"*n*".

In certain embodiments and as shown in FIG. 6, system 200 includes a first sensor assembly 216*a* that is configured and adapted to sense or monitor at least one operational characteristic or processing feature of the microfluidic assembly 218, a second sensor assembly 216*b* that is configured and adapted to sense or monitor at least one operational characteristic or processing feature of the electromagnetic radiation source assembly 220, a third sensor assembly 216*c* that is configured and adapted to sense or monitor at least one operational characteristic or processing feature of the particle inspection region assembly 222, a fourth sensor assembly 216*d* that is configured and adapted to sense or monitor at least one operational characteristic or processing feature of the particle collection assembly 224, and a fifth sensor assembly 216*e* that is configured and adapted to sense or monitor at least one operational characteristic or processing feature of the optical detector assembly 226. System 200 may have any number of sensor assemblies 216*a*-"*n*" in communication with processor 214.

Exemplary processor 214 is programmed and/or configured to transmit and/or receive signals (e.g., command and/or status signals) or the like to and/or from sensor assemblies 216 and/or microfluidic assembly 218, electromagnetic radiation source assembly 220, particle inspection region assembly 222, particle collection assembly 224 and/or optical detector assembly 226, in order to change the status and/or operating parameters of the components of system 200. As such, processor 214 generally is in communication with sensors 216 and/or the components of system 200 for control and/or communication purposes. Exemplary processor 214 is programmed, configured and/or adapted to enable or facilitate system 200 to process particles in an operatorless fashion based on the operational characteristics sensed by the sensor assemblies 216.

Sensor assembly or assemblies 216*a* associated with microfluidic assembly 218 may be configured to sense or monitor at least one characteristic or feature of sample particle input region 223, channels 203, particle inspection region assembly 222 and/or particle collection assembly 224 so that processor 214 can change one or more parameters or characteristics of assembly 218, assembly 222, and/or assembly 224 based on the sensed or monitored features to enable system 200 to operate in an operatorless fashion.

For example and without limitation, sensor assembly or assemblies 216*a* associated with assembly 218 may sense or monitor such exemplary characteristics of sample input region 223, channels 203, particle inspection region assembly 222, particle collection assembly 224, and/or other components of assembly 218 or system 200 including: insertion and/or removal of chip 218, alignment and/or positioning of chip 218, appropriate pressure levels, sample characteristics, sheath fluid characteristics, waste status and control, stability, alignment adjustment issues, flow rates, identifications, durations, appropriate sort control, signal processing, level monitors, volume presence, number of sorts, purity, yield and/or recovery.

Likewise, sensor assembly 216*b* associated with electromagnetic radiation source assembly 220 may sense or monitor such exemplary characteristics of electromagnetic radiation or light source 221, beam shaping optics 225, and/or other components of assembly 220/system 200 including, without limitation: beam shaping/preparation, excitation source, appropriate power, intensity, beam/light size, wavelength, position, stability and/or motion.

Also, sensor assembly 216*e* associated with optical detector assembly 226 may sense or monitor such exemplary characteristics of detector optics 231, 233, 235 and/or other components of assembly 226 or system 200 including, without limitation: alarms, run progress, safety aspects, instrument start-up, adjustment and/or alignment, direction, position, and/or monitor or control functions.

In general, processor 214 is configured to change (e.g., automatically change) one or more parameters, features, characteristics and/or components of system 200 based on the one or more operational characteristics sensed by the one or more sensor members 216. As such, processor 214 is generally programmed, configured, and/or adapted to enable or facilitate system 200 to process particles in an operatorless fashion.

In certain embodiments, other characteristics/aspects of the components of system 200 that may be monitored or sensed (e.g., via sensor assemblies 216) and/or operated in an operatorless fashion or manner (e.g., via processor 214 and/or sensors 216) may include, without limitation, the following:

(i) instrument start-up (e.g., power sources; electrical sources; laser sources; excitation sources; fluidics; air/vacuum; pumps; detection system; processors/computers; sub-systems; safety mechanisms; self-tests; self-calibration; self-diagnose issues; self-identification of current state (e.g., readiness) for sorting; communication of status);

(ii) input sample (e.g., identification of input sample (what is it for recording, traceability, acceptance, sequenced, measurement or sorting) and/or input sample vessel; presence of sample; quantity of sample at any given time);

(iii) insertion of sample (e.g., initial insertion of sample to system 200 (from or within container); running (flow) of sample; regulation and/or control of sample flow and/or sample flow rate dynamically (periodically and/or to a set-point that is defined automatically or in advance during instrument set-up/manufacture/calibration); monitoring sample volume or level; monitoring event rate and altering sample pressure and/or expulsion rates to achieve a desired set-point for particle event (input) rate);

(iv) sort collection (e.g., vessel insertion/removal; adjust position of vessels (waste, sorted fraction(s)) or of unitary cartridge; sealing of fluidic and/or other necessary connections required to enable system 200 operation; identification and/or selection of particles or particle populations of interest for measurement and/or sorting);

(v) sort mode and/or automated adjustment and/or alignment of operating conditions (e.g., to enable predefined and/or user-specified purity, efficiency, and/or recovery and/or yield modes (event rate, gating schemes, sort rate, abort rate, population resolution, etc.); applying various data manipulation algorithms to calculate and/or automatically adjust data that may be visualized as a rotation or other translation function on one or more dimensions and/or on bivariate data plots to assist with the projection of data in histogram views; adjustment of parameters to bring particle population within acceptable signal limits to enable reliable measurement of particles or to enable certain data to be displayed visually (sensitivity, gain, position of population(s) and/or photodetector amplification) using software, firmware and/or hardware (Example—adjust photodetector voltage and/or gain (until population is in desired location), optical alignment functions are then enabled (excitation source and/or associated optical and/or mechanical elements, flow chamber (particles), detectors) using particles and/or mimic particles or other optical schemes such as light sources, image processing methods or machine vision as non-limiting examples));

(vi) adjusting a sort mechanism (e.g., side calibration timing and/or velocity and expected arrival at sort position/mechanism to enable reliable and stable performance of particle separation to meet the desired outcome (such as given number of particles, desired purity, ratio, recovery, yield, characteristic property, homogeneity, heterogeneity, size, morphology, fluorescence, light scatter properties, immunophenotypic marker profile, DNA content, etc.) (Example—determine either directly (e.g., measuring actual time) or indirectly (e.g., velocity) the time of flight for a particle to travel from an inspection zone to a processing region, such as a sort/switch region);

(vii) adjusting optical measurement apparatus (e.g., through positioning various mechanical or optical components, or by effecting the direction or position of one or more optical paths or particle paths to enable reliable and consistent measurement and/or sorting of particles flowing within system 200 (e.g., within the cytometer apparatus); monitor and control functions (e.g., system leaks (gas or liquid); out of bounds (power, safe shut-down, instrument safety and control network, universal power supply, etc.); trending (e.g., sample quality, sort rate, sort fraction, assessment of live to dead ratio within a sample, scheduling of samples, alarm conditions and alarms); intelligent error handling such as self-fixing, self-regulation or other act such as by reacting to system 200 parameters (e.g., parameter change such as temperature, pressure, vacuum, alignment movement, etc.) that may affect system/instrument operation);

(viii) various alerts and/or alarms (e.g., alerts or alarms that caution device or user that system is nearing or operating outside acceptable limits/window; run and control sheath (waste, sample, sort fraction and trajectory of sort and non-sort fractions) level monitor and refill; cleaning lines; sample waste; etc.);

(ix) safety aspects (e.g., safety of environment or from environment of operator or sample or system/instrument); potential exposure of sample to the environment, the apparatus, and other samples;

(x) automated and/or robotic feeding of samples, such as sheath fluid(s), sort output fractions, waste and other required fluids, consumables, calibration parts, cleaning supplies, etc. (e.g., systems/methods to enable continuous operation over extended periods (e.g., for different samples) without the need for human intervention);

(xi) remote-controlled features and/or operations (e.g., reduce requirement for operator to be in front of system 200, system 200 could be controlled from a remote location or room with respect to the system 200; remote-controlled features that may be particularly useful if there are concerns over sample contamination issues (between samples, or sample and system or environment, or sample and operator, as non-limiting examples), or concerns where pathogens, communicable diseases or the like or other human or non-human vectors are involved (e.g., Hepatitic C, Influenza strains, Malaria, H1N1, HIV, BSE, TB, etc.));

(xii) other aspects of system 200 (e.g., laser alignment; excitation source alignment; detector alignment; data manipulation for identification and zooming; population identification; population sort regions; set-point purity; etc.);

(xiii) auto-rotation (e.g., calculating and automatically adjusting data rotation on one or more bivariate plots to assist with projection of data in histogram views and related gating or sort strategies);

(xiv) event rate (e.g., monitoring event rate and controlling sample pressure to achieve a desired set-point for particle event rate);

(xv) course alignment (e.g., image-based alignment of chip and/or excitation source to predefined position where image is adjusted with respect to expected conditions); and/or (xvi) fine alignment (e.g., data-based alignment of chip, excitation source and/or detector position using feedback from measured photodetector signals (e.g., from calibration or target particles; identify and locate specific sort regions around certain cell populations, such as cells that have been identified as providing therapeutic potential, further use in research or industrial activities, or live oriented X and/or Y sperm cells as non-limiting examples)).

Moreover, the processors 214 and sensor assemblies 216 of the present disclosure may be advantageously utilized to sense or monitor even other characteristics of system 200, including, for example, other characteristics or aspects disclosed and described in U.S. Pat. Nos. 8,277,764; 8,123,044; 7,569,788; 7,492,522 and 6,808,075; U.S. Patent Publication Nos. 2012/0009025; 2012/0277902; 2011/0196637 and 2009/0116005; and U.S. Patent Application Ser. Nos. 61/647,821 and 61/702,114, each incorporated by reference herein in their entireties.

In exemplary embodiments, the alignment of system 200 (e.g., via sensors 216 and processor 214) may be accomplished in the presence or absence of particles or cells. In general, the optical measurement devices of system 200 may be adjusted (e.g., via sensors 216 and processor 214) by positioning various mechanical or optical components, or by effecting the direction or position of one or more optical paths or particle paths to enable reliable and consistent measurement and/or sorting of particles flowing within system 200. In certain embodiments, system 200 is configured and adapted for the operatorless alignment (in the presence or absence of particles) of one or more microfluidic chips 218 (e.g., sorter structures).

In exemplary embodiments, system 200 (e.g., via sensors 216 and processor 214) is configured and adapted to pre-align various optical components of system 200 prior to the insertion of one or more microfluidic chips 218 by utilizing optical techniques and/or by utilizing another one or more microfluidic chip or chips 218. In certain embodiments, system 200 is configured to adjust its optical components to produce one or more electromagnetic radiation or excitation beams 227 that are of a predefined and/or acceptable profile, size, energy density, divergence and/or convergence, wavelength, spatial and/or temporal characteristic.

System 200 may also be configured to align the beams 227 with respect to electromagnetic radiation collection path and/or detectors of optical detector assembly 226. For example, such alignment may be determined by sensor 216 types of which include photodetectors (e.g. photodiodes, photomultiplier tubes, multi-element devices such as photomultiplier arrays, linear CCD arrays, cameras and the like).

System 200 may be configured to introduce and/or move microfluidic chip 218 into place so that electromagnetic radiation beam 227 is incident on or near a region of interest such as particle interrogation region 222a. System 200 can then adjust the chip 218 and/or optical path positions in one or more axes (e.g., including one or more of x, y, z, yaw or theta, pitch, or roll axes), and for the case of a plurality of microfluidic sorters within a single chip 218 on substrate 201, a global translation or rotation in one or more axes. System 200 may further fine-tune alignment steps to further adjust particle measurement such as utilizing optical apertures (on- or off-chip 218, or a combination of both) to isolate particular regions of excitation and/or light collection. For example, it may be desirable to provide a tighter position of chip 218 by putting optical apertures in place (in addition to masks that may already be in use).

The chip 218, various optical components of system 200, and/or optical paths may be modified by the system (e.g., via motion control stages) to determine or set the location of any parameter of system 200. For example, a linear scan may be performed one or more times to sweep through multiple locations so that the peak signal (e.g., excitation, fluorescence, scatter, etc.) intensity or power or some other position may be found. Moreover, a combination of rotation and/or linear scan actions may also be conducted by system 200 to achieve similar purposes.

Furthermore the shape and/or location of any apertures of chip 218 may be used as yet further aids for aligning. For example, without limitation, the relative amount (e.g., ratio) of electromagnetic radiation transmitted by two or more apertures of chip 218 may be measured as the alignment of components within the system 200 is changed. A peak ratio or the like may be used to identify when an electromagnetic radiation or excitation source 221 is appropriately positioned with respect to a microfluidic sorter 218, and/or a particle measurement location 222a.

Further, optical alignment techniques of system 200 may include alignment by monitoring a plurality of particle measurement locations 222a, and/or a plurality of electromagnetic radiation or light collection components or optical paths. In certain embodiments, optical fibers or optical fiber bundles and/or arrays (e.g., detectors 231) may be used for electromagnetic radiation collection, and may be moved individually or collectively to adjust electromagnetic radiation detection with respect to an electromagnetic radiation source 221 and one or more microfluidic sorters 218.

Such functions may be performed in an automated fashion that uses algorithms that monitor and/or adjust certain signals and/or positions of one or more components of system 200. For example, a processor 214 or the like programmed with software algorithms may be used to determine and/or control optical alignment of system 200. In other embodiments, software algorithms may be implemented in other devices such as, without limitation, microprocessors, field programmable gate arrays, etc. Other suitable mechanical components and/or movable elements of system 200 may be utilized to perform required motions in any one or more dimensions. As noted, measurements and/or operatorless optical alignment functions may be performed in the presence or absence of particles flowing through the one or more microfluidic sorters 218.

Exemplary Microfluidic Alignment:

In exemplary embodiments, system 200 (e.g., via sensors 216 and processor 214) is configured and adapted for aligning a plurality of microfluidic sorters within one or more microfluidic chips 218 without operator intervention, by following the below noted steps. For example, processor 214 may control (e.g., programmatically control or perform) the following steps to facilitate operatorless alignments:

1) Processor 214 of system 200 aligns a detector (e.g., the axial electromagnetic radiation extinction fiber ribbon (linear array) assembly 231) with respect to the electromagnetic radiation 227 from segmented minor 225 (for multiple electromagnetic radiation beams, it is noted that there may be a one to one or other relationship of beams and/or paths and electromagnetic radiation collection and detection paths).
   a. System 200 programmatically sets electromagnetic radiation 221 to low power, to avoid damage to any part of electromagnetic radiation fiber assembly 231.
   b. Microfluidic chip 218 is then homed (e.g., returned to a known reference position or starting position) using, for example, chip stage y-axis, to remove it from the electromagnetic radiation path (e.g., no interference). As used herein "x-axis" and "y-axis" extend in directions within the plane of the cross-section of the electromagnetic radiation beam and "z-axis" extends in a direction along the axis of the electromagnetic radiation beam. As such, the movement or adjustment of any particular component, if described in terms of x-axis, y-axis or z-axis stages, is relative to that component's position in the path of the electromagnetic radiation beam. In addition the y-axis extends in a direction across (i.e., lateral) to the fluidic flow. The x-axis extends in a direction aligned (i.e., longitudinal) with the fluidic flow.
   c. System 200 positions the detector assembly (e.g., the electromagnetic radiation extinction detector) stage x- and y-axes to nominal (e.g., pre-determined, calibrated, or taught) positions.
   d. System 200 aligns the detector assembly (e.g., the extinction detector) stage x-axis to a desired position for most electromagnetic radiation by scanning the nominal range (field of interest which may be equal to or smaller than the full range of motion of one or more axes), then determining measured optical power values, and averaging desired positions for all microfluidic sorter detection channels 203. Two scans may be used. The first produces a coarse-aligned position by scanning a nominally wide range with a large step value. From the desired position from the coarse scan, system 200 then scans a narrow range about the desired position with small step values. This produces a fine-aligned position.
   e. System 200 aligns electromagnetic radiation extinction y-axis to a desired position for most electromagnetic radiation, (same scan method as discussed above).

2) System 200 aligns chip 218 with respect to electromagnetic radiation 227 from segmented minor 225
   a. System 200 then provides fluid flow through chip 218 (flow may be provided by sheath only; sample, particles or beads are not required).
   b. System 200 moves chip 218 into nominal (e.g., a known, previous, expected, and/or reference) position in electromagnetic radiation path.
   c. System 200 sets laser to high(er) power.
   d. System 200 jogs (e.g., moves) extinction source in x-axis to compensate for refraction of electromagnetic radiation (e.g., laser light) through chip 218.
   e. System 200 aligns chip 218 x-axis to desired position for most electromagnetic radiation (e.g., maximum electromagnetic radiation transmission through chip 218 microsorter flow channels 203), by scanning nominal range, recording measured optical power values, and averaging positions for all flow channels 203.
   f. Align chip 218 y-axis to position, same method as above.
   g. Align chip theta (rotational) axis to position, same method as above.

3) System 200 re-aligns extinction ribbon 231 x-axis.
   a. Chip 218 is still flowing fluid (e.g., may be sheath only, and not sample or particles), at aligned position from step (2) above.
   b. System 200 aligns extinction x-axis to position for maximum electromagnetic radiation transmission through microsorter flow channels 203, by scanning nominal range, recording measured optical power values, and averaging positions for all channels 203.

4) System 200 aligns chip 218 peak ratio.
   a. System 200 flows sheath and sample to chip 218 (e.g., with beads, cells, or other particles as a calibration particle).
   b. System 200 calculates the desired peak ratio from the geometry of chip 218 pinholes. For example, for a plurality of pinholes, one could find a desired peak ratio (e.g., less than 1:1, or greater than 1:1).
   c. System 200 aligns chip 218 x-axis for peak ratio by scanning a nominal range, and for each channel 203 only use positions where a good event rate or the like is above a pre-determined threshold. System 200 then finds which valid position is closest to a target peak ratio.
   d. System 200 aligns chip 218 about the theta axis for peak ratio by scanning a nominal range, and for each channel 203 only use positions where a good event rate (i.e., events that are considered acceptable with respect to defined event acceptance attributes such as signal strength, threshold crossings, etc.) or the like is above a pre-determined threshold. Then performs a line fit of valid positions.
   e. If slope of the line fit is above a threshold, system 200 uses the sign of the slope to determine which direction to move theta axis, to reduce the line slope. System 200 then performs another scan and re-calculates.
   f. If slope of line fit is below a threshold, the theta peak ratio alignment of chip 218 is complete.

5) System 200 aligns side scatter ribbon in x-axis.
   a. System 200 flows sheath and sample through chip 218 with beads, cells, or other particles.
   b. System 200 aligns the side scatter ribbon 233 x-axis to position for most electromagnetic radiation, by scanning nominal range, recording measured side scatter values, and averaging positions for all channels.

6) System 200 aligns fluorescence ribbon 235 in the x, y, z axes.
   a. System 200 flows sheath and sample through chip 218 with beads, cells, or other particles.
   b. System 200 aligns fluorescent ribbon 233 x-axis to position for most electromagnetic radiation, by scanning nominal range, recording measured fluorescent values, and averaging positions for all channels.
   c. Aligns fluorescent ribbon 233 y-axis to position for most electromagnetic radiation, by scanning nominal range, recording measured fluorescent values, and averaging positions for all channels.

d. Aligns fluorescent ribbon 233 z-axis to position for most electromagnetic radiation, by scanning nominal range, recording measure fluorescent electromagnetic radiation values, and averaging positions for all channels.

It is to be understood that for any of the alignment methods described above, one or more of the steps and/or sub-steps delineated above may be eliminated, that the steps and/or sub-steps need not necessarily be performed in the order presented above, that one or more step, sub-steps and/or blocks of steps and/or sub-steps may be repeated; and/or additional and/or other steps and/or sub-steps may be interposed.

Exemplary Microfluidic Assembly/Chip 218 Alignment Methods:

In exemplary embodiments, system 200 may be configured and adapted to automatically align (e.g., via sensors 216 and processor 214) the pinhole array on chip or chips 218 of system 200 with the optical path between the segmented mirror (or other beam shaping optics) 225 and an optical detector subsystem (e.g., the optical extinction detector subsystem 231) to ensure that the maximum electromagnetic radiation is transmitted through chip 218 substantially unobstructed. The optical detector subsystem may function as an optical power detector array.

It is noted that each newly inserted chip 218 into the chip-holder or the like of system 200 may create microdisplacement of several (or several tens) of microns in any of multiple axes (x, y, z, yaw (theta), pitch, roll). As such, micron precision requirements of chip 218 or system 200 may warrant chip 218 to undergo an alignment procedure. In general, a chip-holder stage and/or a receptacle of system 200 may have one motorized stage per axis to enable software controlled automated alignment of chip 218.

In general, machine vision systems may use optical sensors or the like (e.g., point-wise scanning sensors that sense one sample at a time, one-dimensional array sensors that sense one line at a time, two-dimensional sensor arrays that sense an entire two-dimensional scene at a time). In exemplary embodiments, system 200 of the present disclosure may utilize a hybrid of point-wise scanning sensors and one-dimensional array sensors due, in part, to the need for high spatial resolution and other hardware design considerations. In certain embodiments, the area of interest on a chip 218 or the like may be roughly about 70 mm by about 4 mm.

In exemplary embodiments, chip 218 alignment of system 200 is a process of proactively moving (automatically) the chip 218 in stages or increments so that particular detection locations 222a (e.g., an operational row of pinholes) on a chip 218 may be properly positioned with respect to the optical transmission of the electromagnetic radiation (e.g., laser light) 227 to the detector assembly 226. This may involve optical transmission of the electromagnetic radiation 227 from the segmented mirrors (or other beam shaping optics) 225 to sensors and/or individual detectors on a fiber ribbon of an optical extinction subassembly 231.

In certain embodiments, it is noted that chips 218 used by system 200 may be disposable, so several new chips 218 may be required to be inserted into system 200 each day. Moreover, due to imprecisions or the like of some chip-holders/insertion methods, each inserted chip 218 may generally need to be aligned after insertion. It is also noted that, in general, a manual chip 218 alignment process may be a tedious, time-consuming, subjective and/or unreliable process.

In exemplary embodiments, the automatic (i.e., operatorless) alignment systems and methods of system 200 may be highly repeatable, with the alignment results (optical transmission) not varying significantly from one alignment repetition to another. In general, the automatic alignment systems and methods of chips 218 may be highly accurate, with the alignment position generally within about 5 microns of the desired position. Optionally, if such tight alignment tolerances are not required, the alignments may be accurate to within 10, to within 20 or even within 30 microns. Moreover, the automatic alignment systems and methods of chip 218 may be fully automated to self-navigate in the x, y, and theta (and other) axes spaces. Furthermore, the automatic alignment systems and methods of chips 218 of system 200 may be accomplished in a short amount of time (e.g., in less than about 5 minutes, in less than about 30 seconds, in less than about 5 seconds, or in less than about 1 second). As a non-limiting example, if higher accuracy is desired, the scanning increment may be approximately 5 microns and the time for alignment may be on the order of minutes. As another non-limiting example, if a more nominal accuracy is sufficient, the scanning increment may be approximately 30 microns and the time for alignment may be on the order of minutes.

Figure 10:
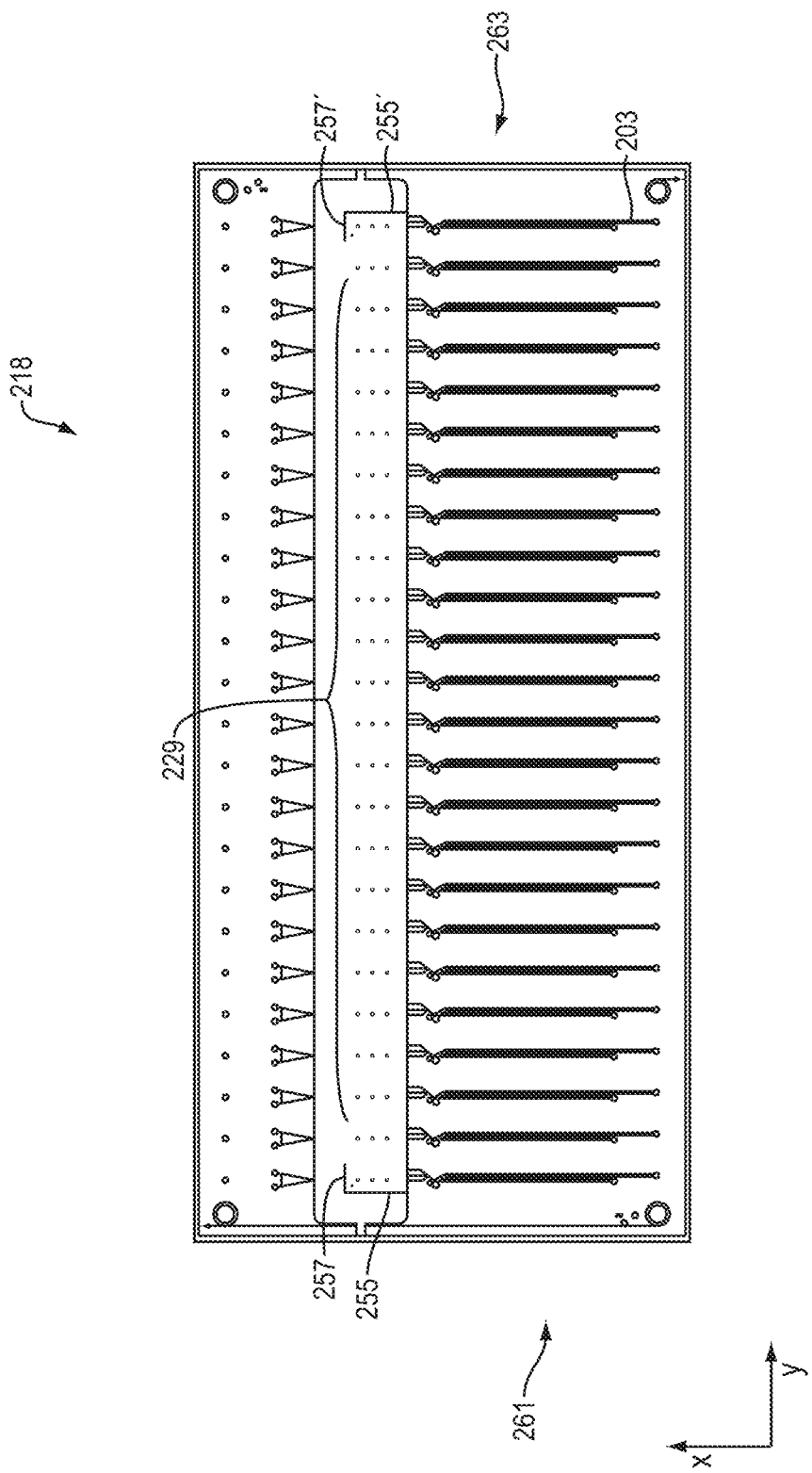
FIG. 10 illustrates another exemplary microfluidic assembly of the present disclosure.

In exemplary embodiments and as shown in FIG. 10, microfluidic chip 218 may include at least one fiducial marker. A fiducial is a reference point; a fiducial marker is an object placed in the field of view of an imaging system which appears in the image produced, for use as a point of reference or a measure. According to an aspect, chip 218 may include at least one Y-fiducial marker 255 and at least one X-fiducial marker 257. The X- and Y-fiducial markers may be elongated marks oriented perpendicular (or at another angle) to one another. For example, a Y-fiducial marker may have a detectable feature extending in an x-direction (i.e., in a direction substantially parallel to a microfluidic channel 203 on chip 218) and an X-fiducial marker may have a detectable feature extending in a y-direction (i.e., in a direction substantially perpendicular to a microfluidic channel 203 on chip 218). In certain embodiments, chip 218 includes a first Y-fiducial marker 255 and a first X-fiducial marker 257 proximal to a first end 261 of chip 218, and a second Y-fiducial marker 255' and a second X-fiducial marker 257' proximal to a second end 263 of chip 218. It is noted that chip 218 may include any number of Y-fiducial markers 255 and/or X-fiducial markers 257. Moreover, chip 218 may include only Y-fiducial markers 255 or only X-fiducial markers 257. In general, the fiducial marks may be any shape, number and/or orientation. Further, in general, the fiducial marks may include extinction, reflective, refractive, diffractive and/or even fluorescent elements, and thus, any excitation/detection system may be used to perform the operatorless chip alignment process. In a preferred aspect, the operatorless chip alignment process may use the same electromagnetic radiation 227 slated to-be-used to interrogate a sample flowing through the microfluidic channels 203 of the chip 218 and the optical extinction subassembly 231. In such instance, the fiducial elements may be extinction elements formed on a transmissive substrate, may be mask elements formed on a transmissive substrate, may be apertures formed on a non-transmissive substrate, etc.

In exemplary embodiments, system 200 may be configured and adapted to automatically align (e.g., via sensors 216 and processor 214) a pinhole array 229 on chip 218 with the optical path between the segmented minor (and beam shaping optics) 225 and the optical power detector array 231 to ensure that the maximum electromagnetic radiation is passing through chip 218 substantially unobstructed. In certain embodiments and as discussed below, such automatic alignment may be accomplished by utilizing the Y-fiducial markers 255 and/or the X-fiducial markers 257 or substantially only fiducial marker 255 and/or 257. In other embodiments and also as discussed below, such automatic alignment may be accomplished via a combination of fiducial marker 255 and/or 257 navigation along with navigation utilizing other artifacts/markers on chip 218.

For example, in one embodiment the fiducial markers 255, 257 may be located by system 200 and, based in part on known chip 218 topology or the like, system 200 may then calculate (or otherwise determine) the coordinates of the operational pinholes of chip 218. In exemplary embodiments, such operatorless adjustment may be achieved by: (i) a coarse-to-fine approach, (ii) the calculation of theta rather than scanning for various theta angles (theta axis), and/or (iii) sub-sample spatial resolution achieved based on a Gaussian fit.

In a further exemplary embodiment and as shown in FIGS. 11-16, system 200 may be programmed, configured and adapted to automatically align chip 218 by utilizing the following steps:
 (i) coarsely scan chip 218 in the y-direction for Y-fiducial markers 255 and/or 255' (refer to arrows in FIG. 12(i));
 (ii) determine the coarse position of the Y-axis ($Y_{coarse}$) for chip 218, i.e., the position of the Y-axis that provides the greatest intensity;
 (iii) coarsely scan chip 218 in the x-direction for X-fiducial markers 257 and/or 257' (refer to arrows in FIG. 12(i));
 (iv) determine the slant angle $Theta_{coarse}$ for chip 218 (refer to FIG. 13);
 (v) deslant chip 218 by $-Theta_{coarse}$ (refer to FIG. 13);
 (vi) re-scan chip 218 finely in the x-direction to get to the fine $X_{align}$ position (refer to FIG. 14(i));
 (vii) determine fine slant angle $Theta_{align}$ (refer to FIG. 14(ii));
 (viii) deslant by $-Theta_{align}$;
 (ix) fine scan in the y-direction around $Y_{coarse}$ and find fine $Y_{align}$ position (refer to FIG. 15);
 (x) move to the $X_{align}$, $Y_{align}$ position for chip 218; and
 (xi) acquire signal (e.g., electromagnetic radiation passing through chip 218) (refer to FIG. 16).

Figure 11:
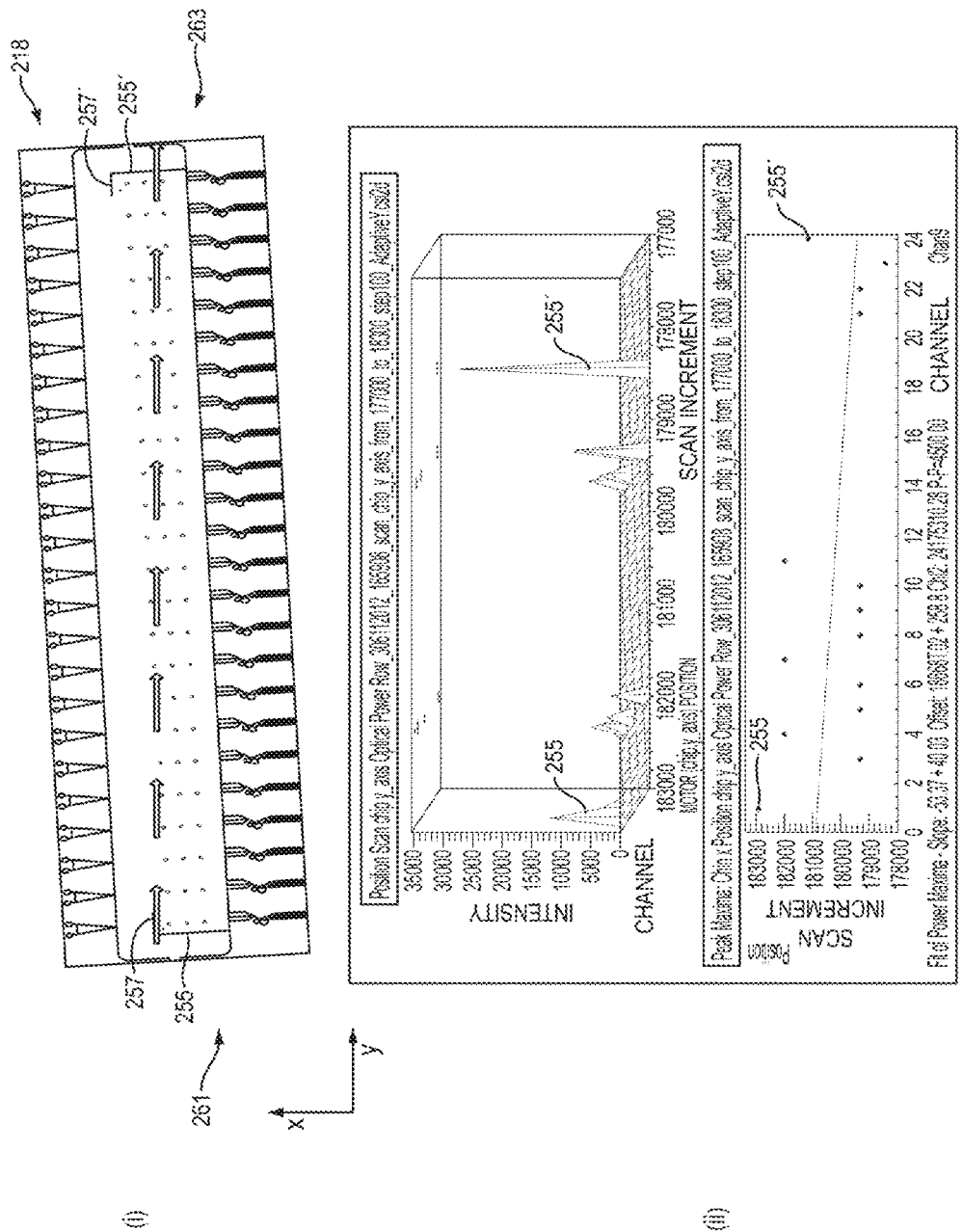
FIGS. 11-16 illustrate an exemplary process/method for aligning a microfluidic assembly of the present disclosure.

FIG. 11 illustrates a coarse scanning process wherein: (i) the microfluidic chip 218 is moved in the y-direction using a motor-driven stage to detect the Y-fiducials; and (ii) data is collected and plotted for each increment of the coarse scanning process. In the first three-dimensional graph, data is presented as signal intensity for each microfluidic channel and for each y-direction scanning increment or position. In this particular graph, the incremental scanning step in the y-direction is 100 microns. In the two-dimensional graph, the peak signal intensity is plotted with respect to each microfluidic channel and its scanned position.

Figure 12:
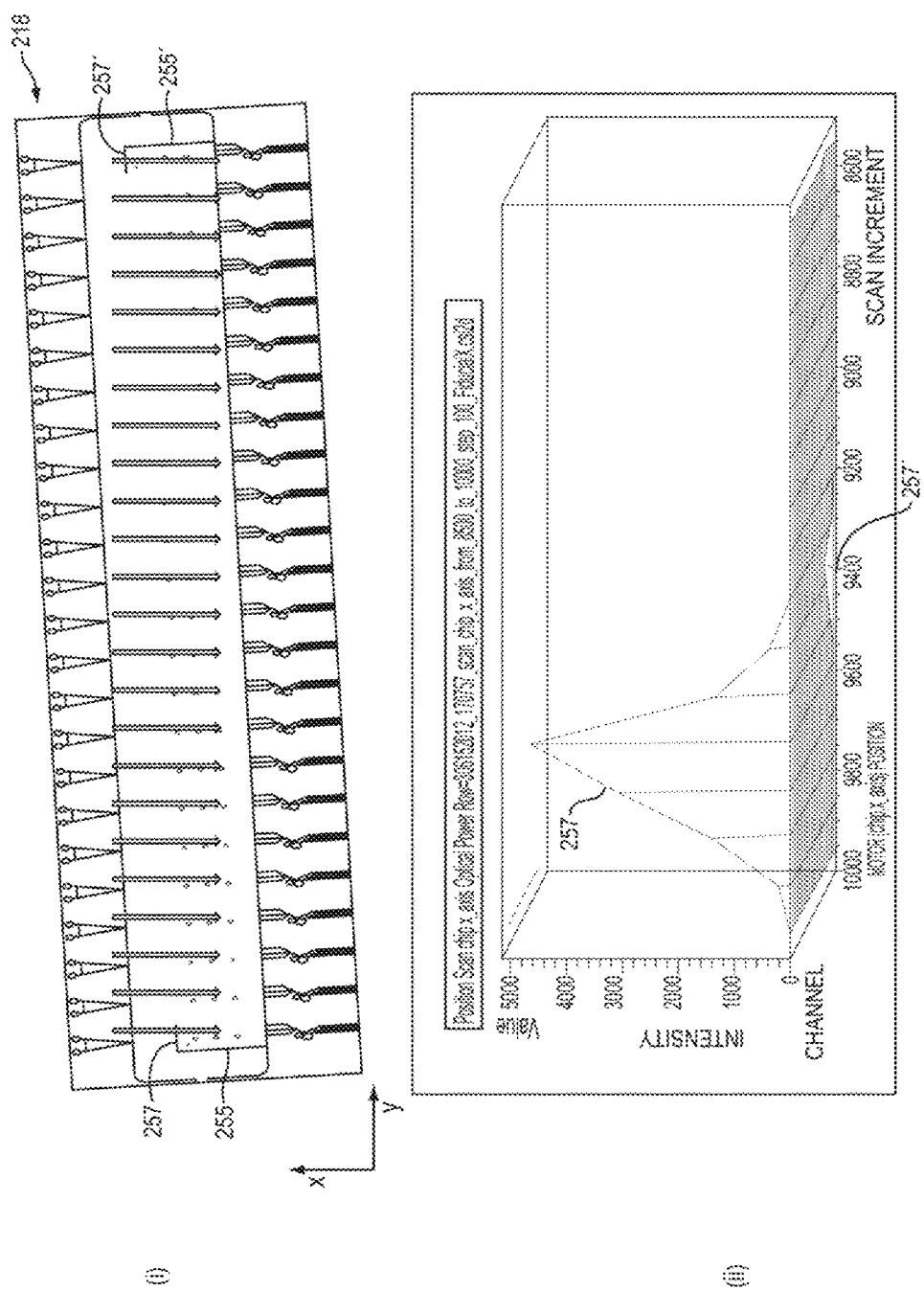

FIG. 12 illustrates a coarse scanning process wherein: (i) the microfluidic chip 218 is moved in the x-direction to detect the X-fiducials; and (ii) data is collected and plotted for each increment of the coarse scanning process. In the three-dimensional graph, data is presented as signal intensity for each microfluidic channel and for each x-direction scanning increment or position. In this particular graph, the incremental scanning step in the x-direction is 100 microns.

Figure 13:
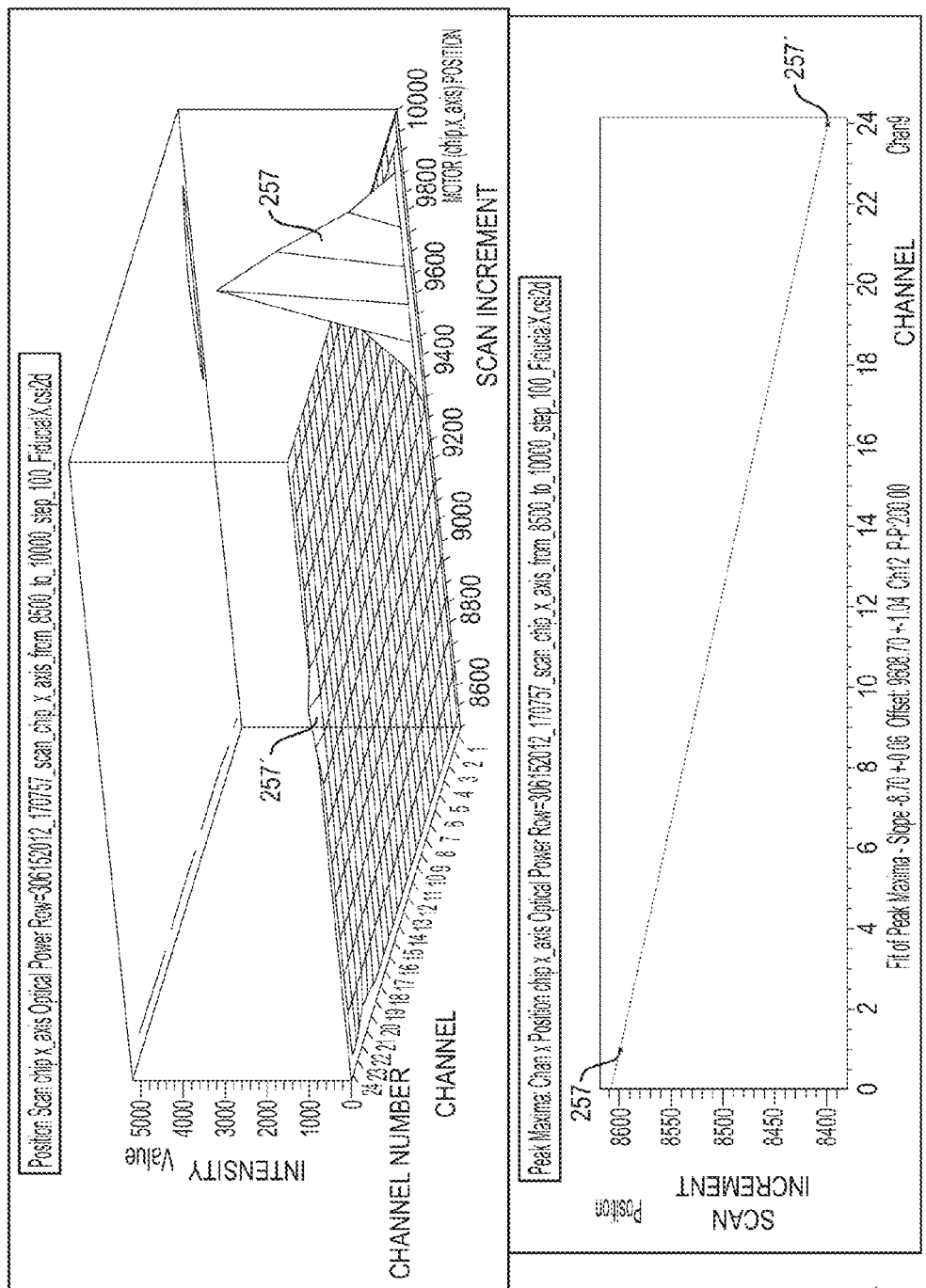

FIG. 13 illustrates that a course slant angle may be determined from data generated from the course scanning steps of FIG. 12. In the three-dimensional graph, data is presented as signal intensity for each microfluidic channel and for each x-direction scanning increment or position. In this particular graph, the incremental scanning step in the x-direction is 100 microns. In the lower two-dimensional graph, the peak signal intensity of the two fiducial markers 257, 257' are plotted across the channels. If the chip 218 was perfectly aligned, the difference between the scan increment for the first X-fiducial 257 would be the same as the scan increment for the second X-fiducial 257'. The difference between the scan increment value for the first X-fiducial and the second X-fiducial and the known distance between the fiducials is used to calculate a $theta_{course}$ value. The chip 218 may then be rotated by an amount equal to the negative of the $theta_{course}$ value to obtain a coarsely aligned angular position.

Figure 14:
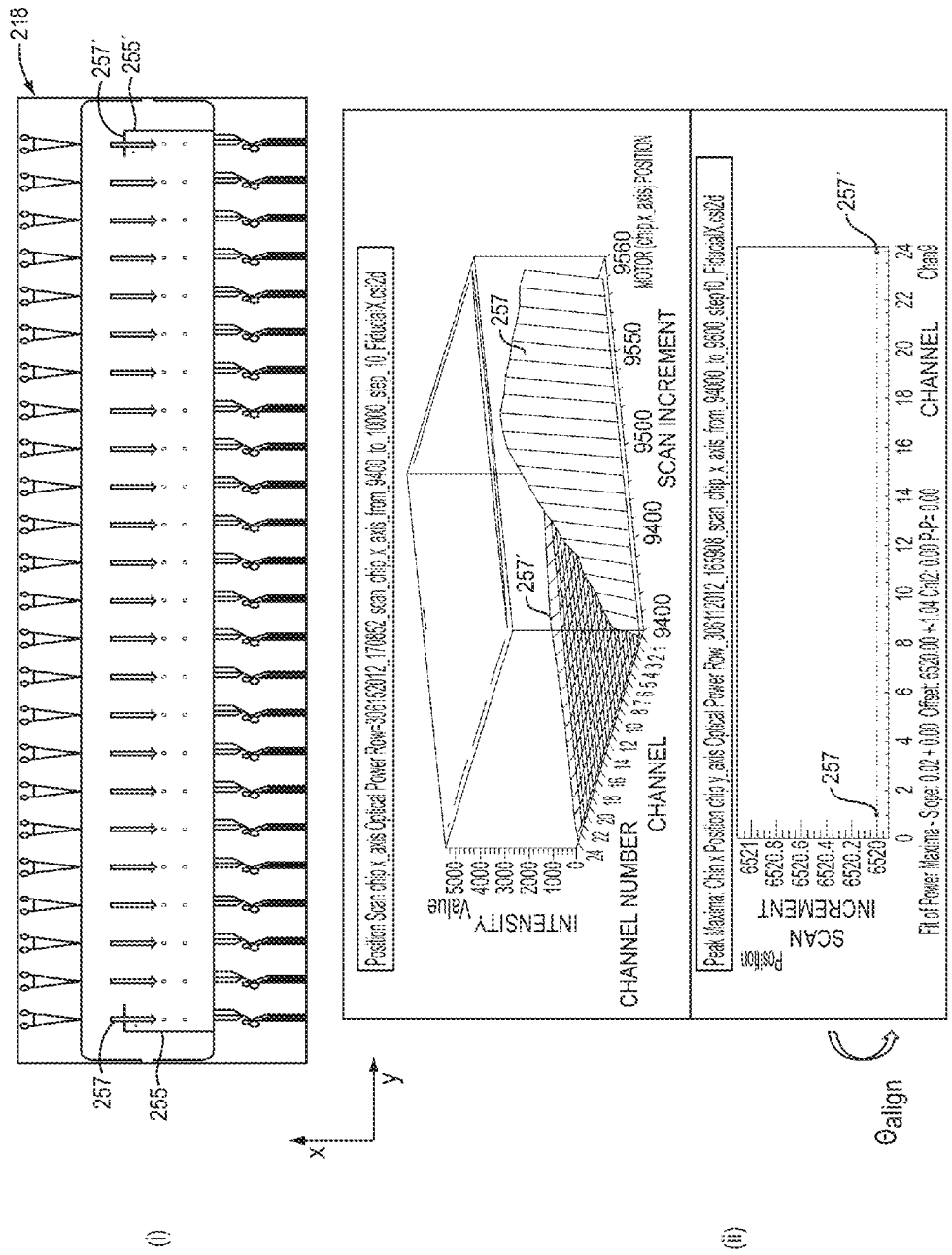

FIG. 14 illustrates a fine scanning process wherein: (i) the microfluidic chip 218 is moved in the x-direction to detect the X-fiducials; and (ii) data is collected, plotted and analyzed to determine a fine $X_{align}$ value and a fine $theta_{align}$ value based on this fine scanning process. In the three-dimensional graph, data is presented as signal intensity for each microfluidic channel and for each x-direction scanning increment or position. In this particular graph, the incremental scanning step in the x-direction is 10 microns. In the lower two-dimensional graph, the peak signal intensity of the two fiducial markers 257, 257' are plotted across the channels. The difference in the scan increment value for the first and second X-fiducial and the known distance between the fiducials is used to calculate a $theta_{align}$ value. The chip 218 may then be rotated by an amount equal to the negative of the $theta_{course}$ value to obtain a finely aligned angular position.

Figure 15:
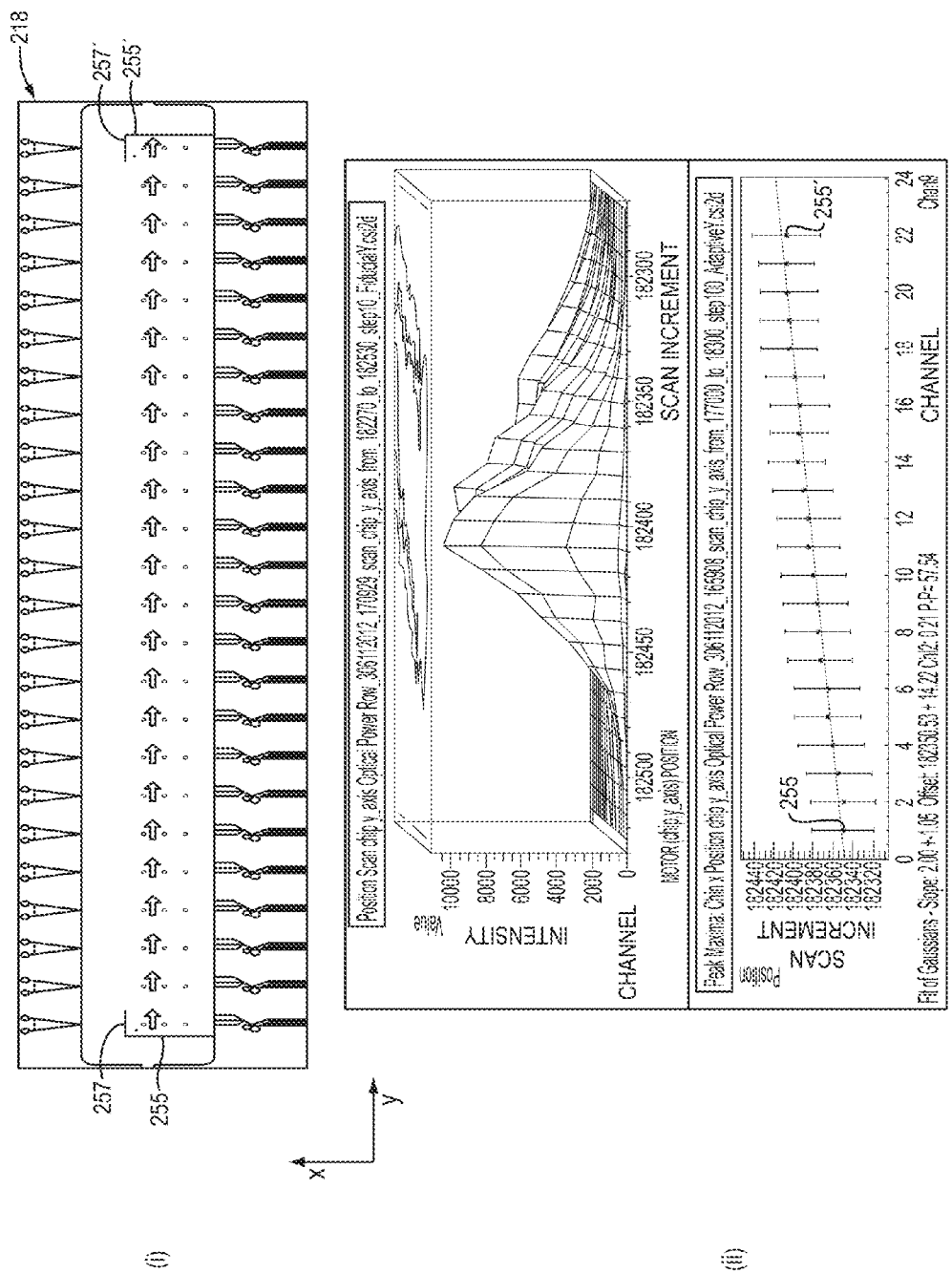

FIG. 15 illustrates a fine scanning process wherein: (i) the microfluidic chip 218 is moved in the y-direction to detect the Y-fiducials; and (ii) data is collected, plotted and analyzed to determine a fine $Y_{align}$ positioning value.

Figure 16:
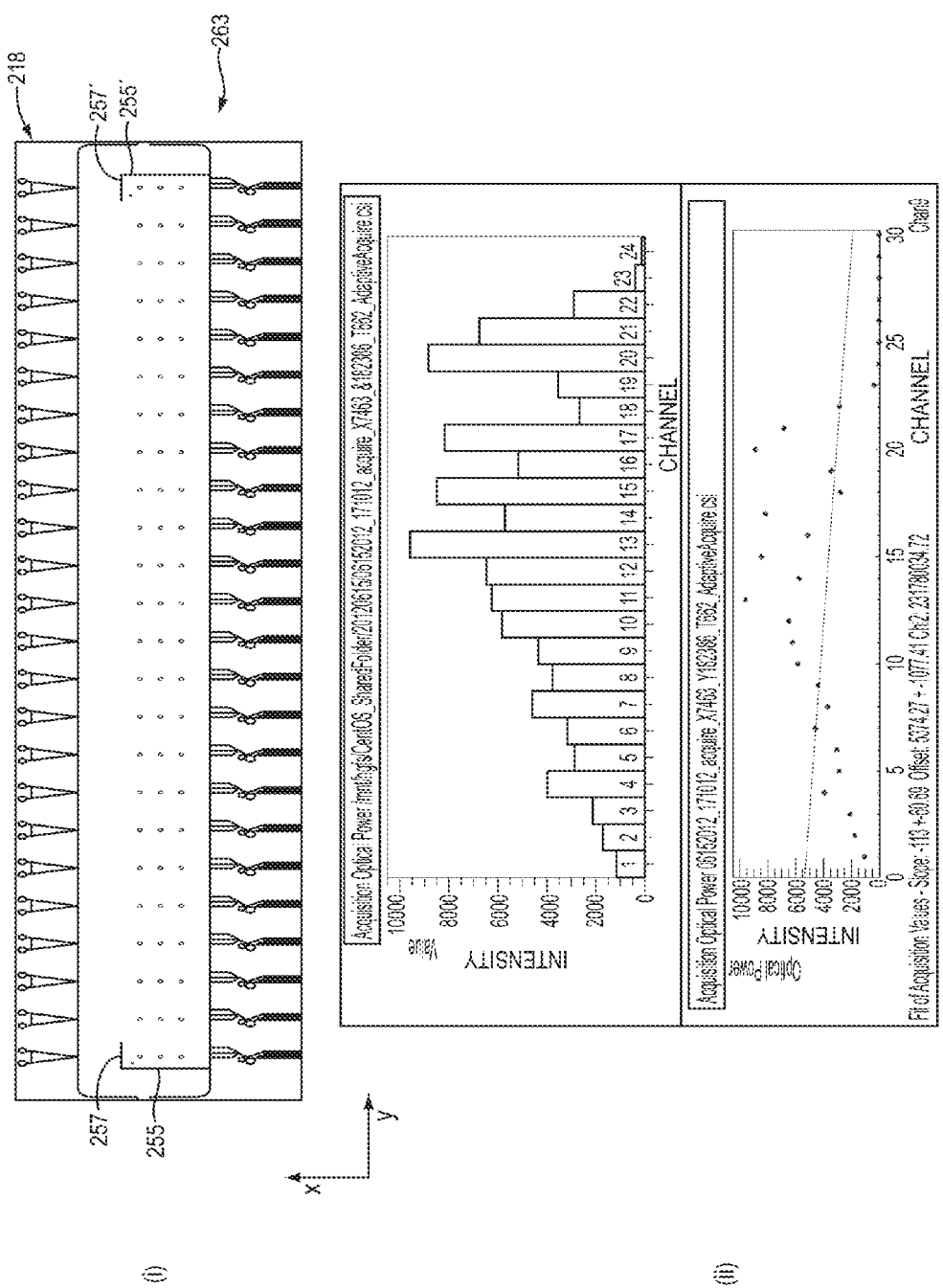

FIG. 16 illustrates the microfluidic chip 218 moved through its fine $X_{align}$ and $Y_{align}$ positioning values to its final aligned position. Each microfluidic channel is thus automatically properly aligned with the electromagnetic radiation source so that particle processing data may be acquired. Data may be acquired to verify the alignment.

During the scanning operations, microfluidic chip 218 may be motor driven in the x- or y-directions. Extinction data may be collected during each step. A typical course scan step dimension may range from 50 microns to 300 microns. Preferably, the course scan step dimension may be less than approximately 150 microns. As an example, the coarse scan step dimension associated with FIGS. 11 and 12 may be 100 microns. A typical fine scan step dimension may range from 5 microns to 50 microns. Preferably, the fine scan step dimension may be less than approximately 20 microns. As an example, the fine scan step dimension associated with FIGS. 14 and 15 may be 10 microns. In general, the coarse scan increment may be from 5 times to 20 times the fine scan increment. In a preferred embodiment, the coarse scan increment may be approximately 10 times the fine scan increment. The scan increments (coarse and/or fine) in the x-direction need not be the same as the scan increments (coarse and/or fine) in the y-direction. Theta is calculated based on known dimensions associated with the fiducials and the measured relative positions of the fiducial signals. During the deslant operations, microfluidic chip 218 may be motor driven around the z-axis.

In general, the X-fiducial(s) and the Y-fiducial(s) may be any length, orientation and/or shape. Typically, the X- and Y-fiducial(s) may be located outside of the pinhole array 229 and/or the signal collection region utilized during particle processing runs.

According to certain embodiments, only a single Y-fiducial may be provided. In such case, the microfluidic chip 218 may be scanned in the y-direction for the Y-fiducial, the chip 218 may be translated in the x-direction, and then chip 218 may be rescanned in the y-direction for the Y-fiducial at the second x-direction station. Thus theta may be determined based on a single Y-fiducial.

According to some embodiments, only a single X-fiducial may be provided. In such case, the microfluidic chip 218 may be scanned in the x-direction for the X-fiducial, the chip 218 may be translated in the y-direction, and then chip 218 may be rescanned in the x-direction for the X-fiducial at the second y-direction station. Thus theta may be determined based on a single X-fiducial.

According to some embodiments, theta may be determined based on the Y-fiducial(s) alone. The one or more X-fiducials may be used to locate the chip 218 in the x-direction. Alternatively, theta may be determined based on the X-fiducial(s) alone. The one or more Y-fiducials may be used to locate the chip 218 in the y-direction.

According to other embodiments, the coarse scan in the x-direction for the X-fiducials step (iii) may be eliminated from the alignment procedure.

According to even other embodiments, only coarse scans may be performed and the deslant operation may be based on the coarse scan data. Alternatively, only fine scans may be performed and the deslant operation may be based on the fine scan data. As even another alternative, only coarse scans in the x-direction may be performed and only fine scans in the y-direction may be performed (or vice versa).

In even another embodiment and as shown in FIGS. 17-24, a subset of the fiducial markers (e.g., Y-fiducial markers 255, 255, when the X-fiducial markers 257, 257 are obscured) may be located by system 200 and other artifacts/markers (pinhole rows, channels 203, actuation points, etc.) on chip 218 may be identified to navigate to and/or calculate the coordinates of the operational pinholes of chip 218.

More specifically and as shown in FIGS. 17-24, system 200 may be configured and adapted to automatically align chip 218 by utilizing the following steps:

(i) coarsely scan chip 218 in the y-direction for Y-fiducial markers 255 and/or 255' (refer to arrows in FIG. 17(i));
(ii) find coarse Y position value ($Y_{coarse}$) for chip 218;
(iii) coarsely scan chip 218 in the x-direction for pinholes ($X_{coarse}$) (refer to arrows in FIG. 18(i));
(iv) determine a fine slant $Theta_{align}$ for chip 218 based on the coarse scanning of the pinholes (e.g., using Radon Transform with sub-degree precision or other suitable mathematical algorithms);
(v) deslant chip 218 by the negative of the fine slant angle $-Theta_{align}$ (refer to deslanted chip 218 of FIG. 19);
(vi) re-scan chip 218 coarsely in the x-direction and determine the middle pinhole row $X_{coarse}$ (e.g., using an autocorrelation function on the integral of the optical transmission to find a pitch and then finding the second peak) (refer to FIGS. 19 and 20);
(vii) fine scan in the x-direction around $X_{coarse}$, (refer to FIG. 21) and then find $X_{align}$ (using, for example, a Gaussian fit) (refer to FIG. 22);
(viii) fine scan in the y-direction around $Y_{coarse}$, and find $Y_{align}$ (using, for example, a Gaussian fit) (refer to FIG. 23);
(ix) move to the $X_{align}$ and $Y_{align}$, position for chip 218; and
(x) acquire signal (e.g., electromagnetic radiation passing through chip 218) (refer to FIG. 24).

Figure 17:
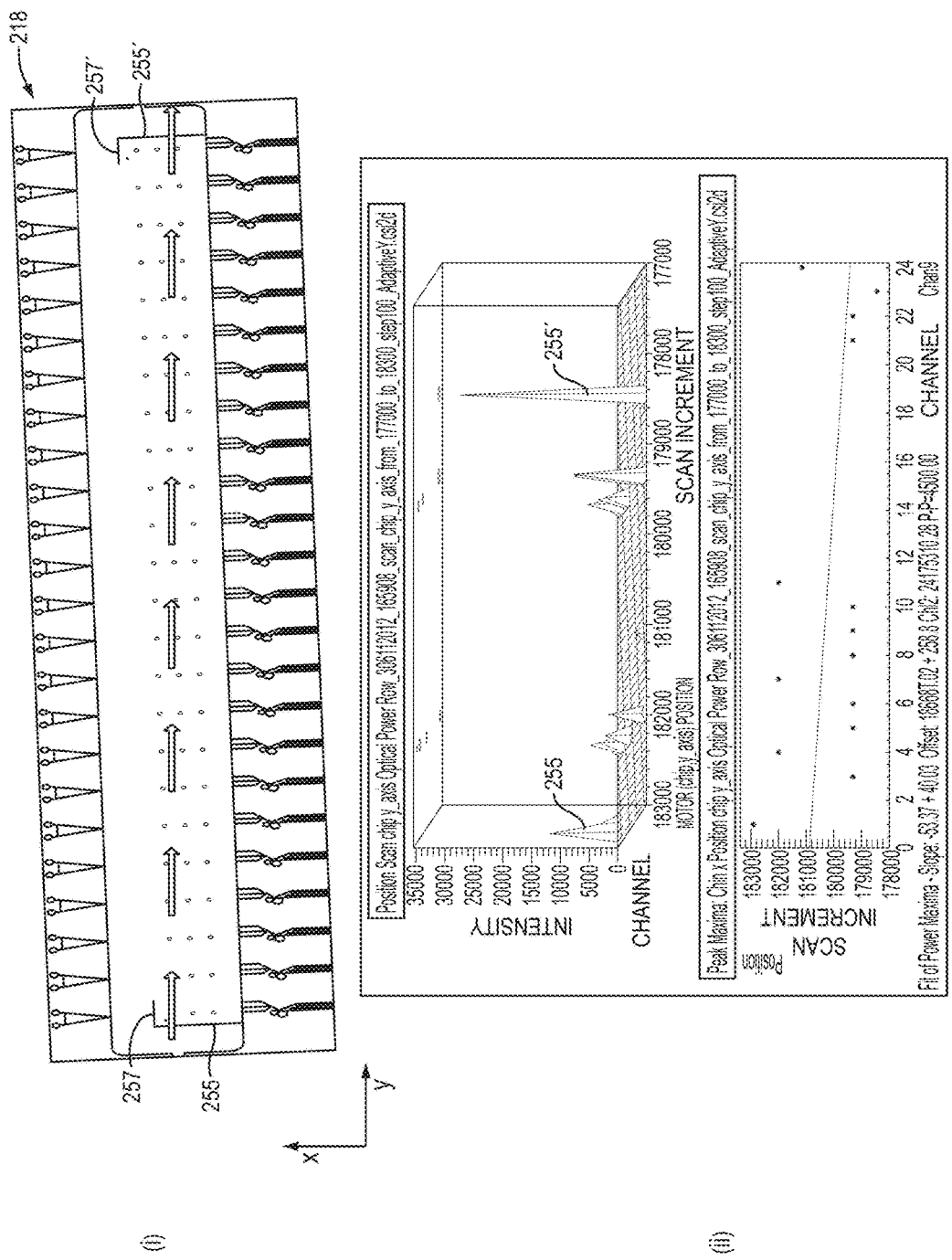
FIGS. 17-24 illustrate another exemplary process/method for aligning a microfluidic assembly of the present disclosure.

FIG. 17 illustrates a coarse scanning process wherein: (i) the microfluidic chip 218 is moved in the y-direction using a motor-driven stage to detect the Y-fiducials; and (ii) data is collected and plotted for each increment of the coarse scanning process. In the upper graph, data is three-dimensionally presented with a relative signal intensity being plotted for each microfluidic channel and for each y-direction scanning increment or position. In this exemplary graph, the incremental scanning step in the y-direction is 100 microns. In the lower graph, the peak signal intensity is plotted with respect to each microfluidic channel and its scanned position.

Figure 18:
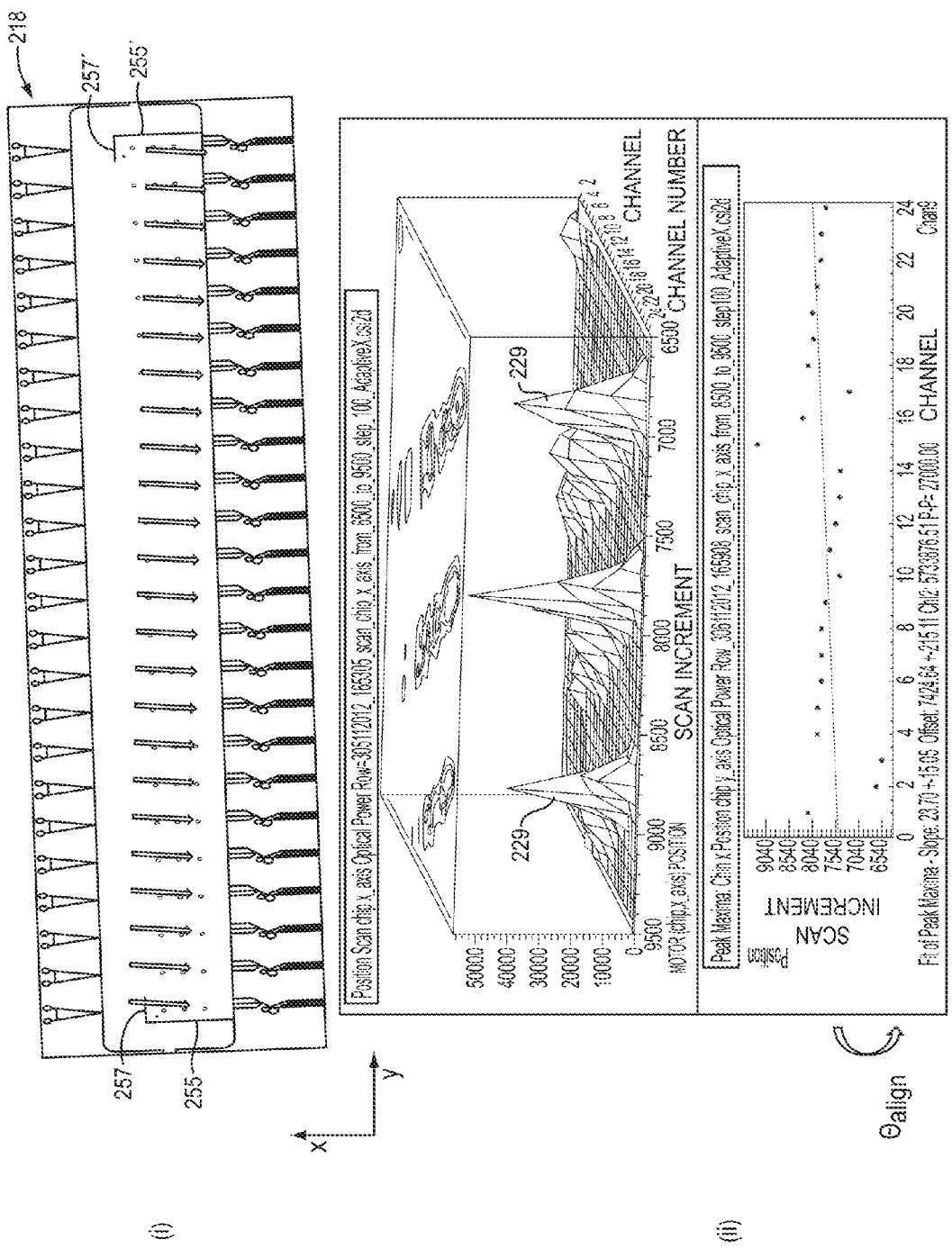

FIG. 18 illustrates a coarse scanning process wherein: (i) the microfluidic chip 218 is moved in the x-direction to detect the pinholes associated with each microfluidic channel; and (ii) data is collected and plotted for each increment of the coarse scanning process. In the three-dimensional graph, data is presented as relative signal intensity for each microfluidic channel and for each x-direction scanning increment or position. In this upper graph, the incremental scanning step in the x-direction is 100 microns. In the lower graph, the peak signal intensity for each pinhole is plotted with respect to each microfluidic channel and its scanned position.

Figure 19:
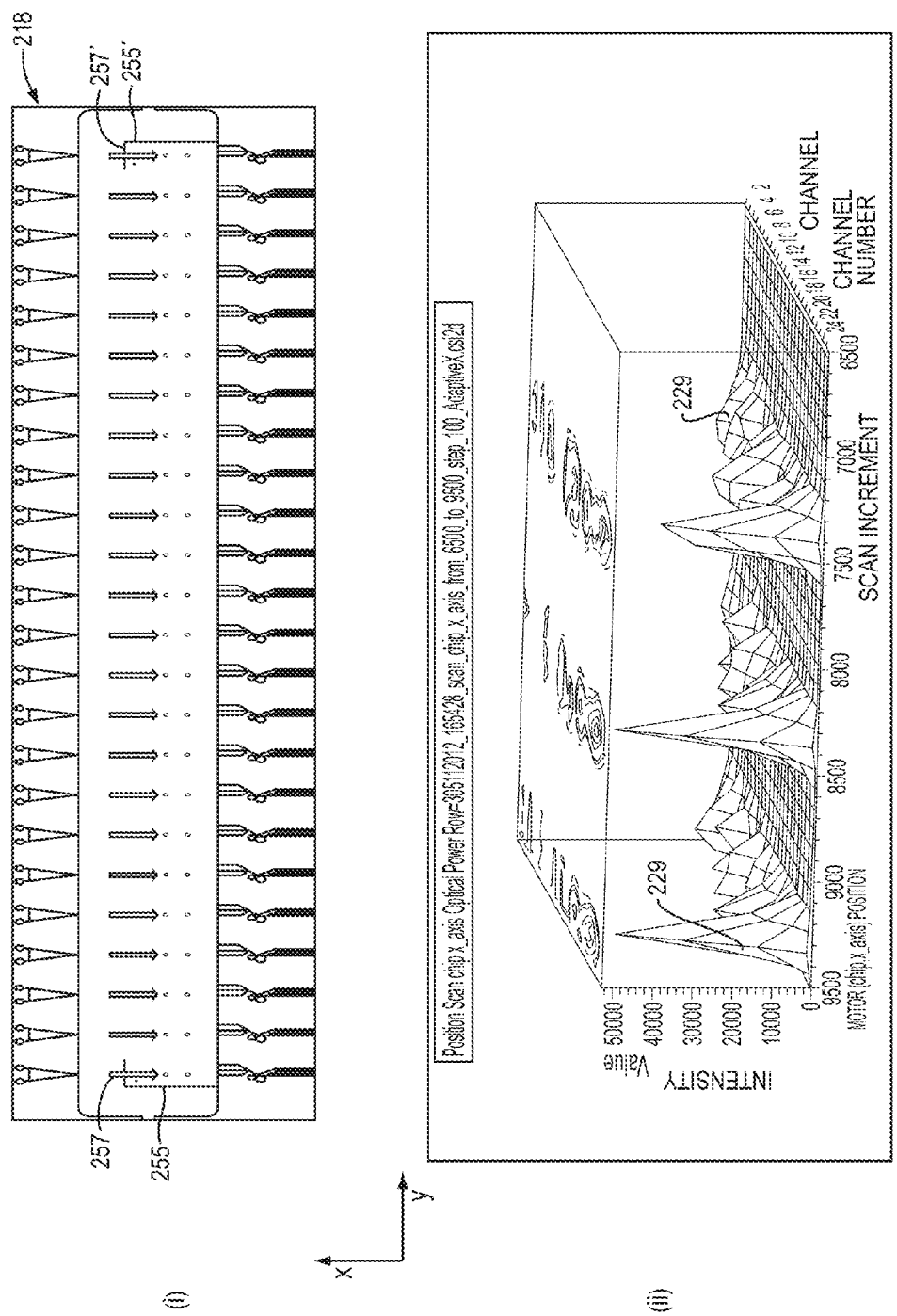

In FIG. 19 the microfluidic chip 218 has been deslanted by the negative of a slant angle $theta_{align}$ determined from data generated from the course scanning steps using a mathematical algorithm such as a Radon Transform. The deslanted chip 218 is coarsely scanned in the y-direction and signal intensity associated with each pinhole is measured (FIG. 19(i)). In the graph FIG. 19(ii), a relative signal intensity for each pinhole 229 is plotted for each microfluidic channel and for each y-direction scanning increment or position.

Figure 20:
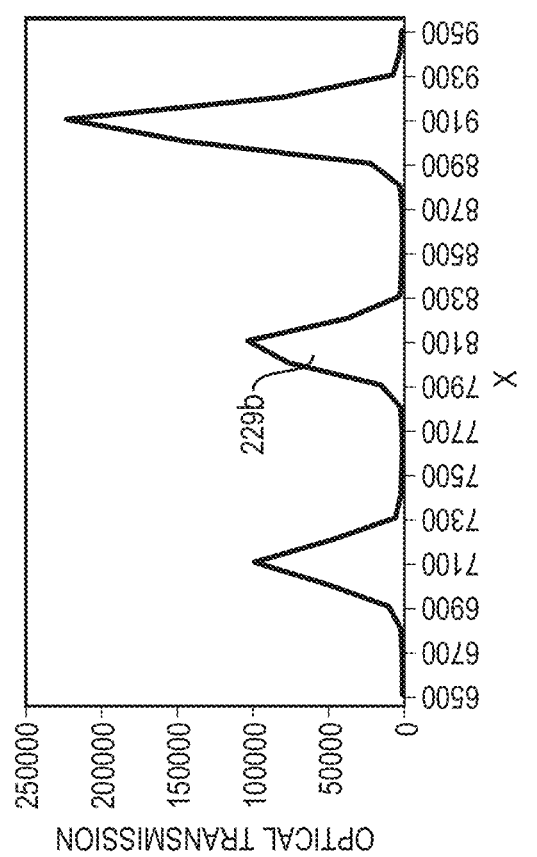

Referring to FIG. 20, the optical transmissions of the pinholes for the data collected in FIG. 19 are graphed as a function of scan increment and the location of the middle pinhole row is determined. This provides a coarse X position ($X_{coarse}$). The location of the middle pinhole row 229b may be determined using an autocorrelation function on the integral of the optical transmission to find a pitch and then finding the second peak.

Figure 21:
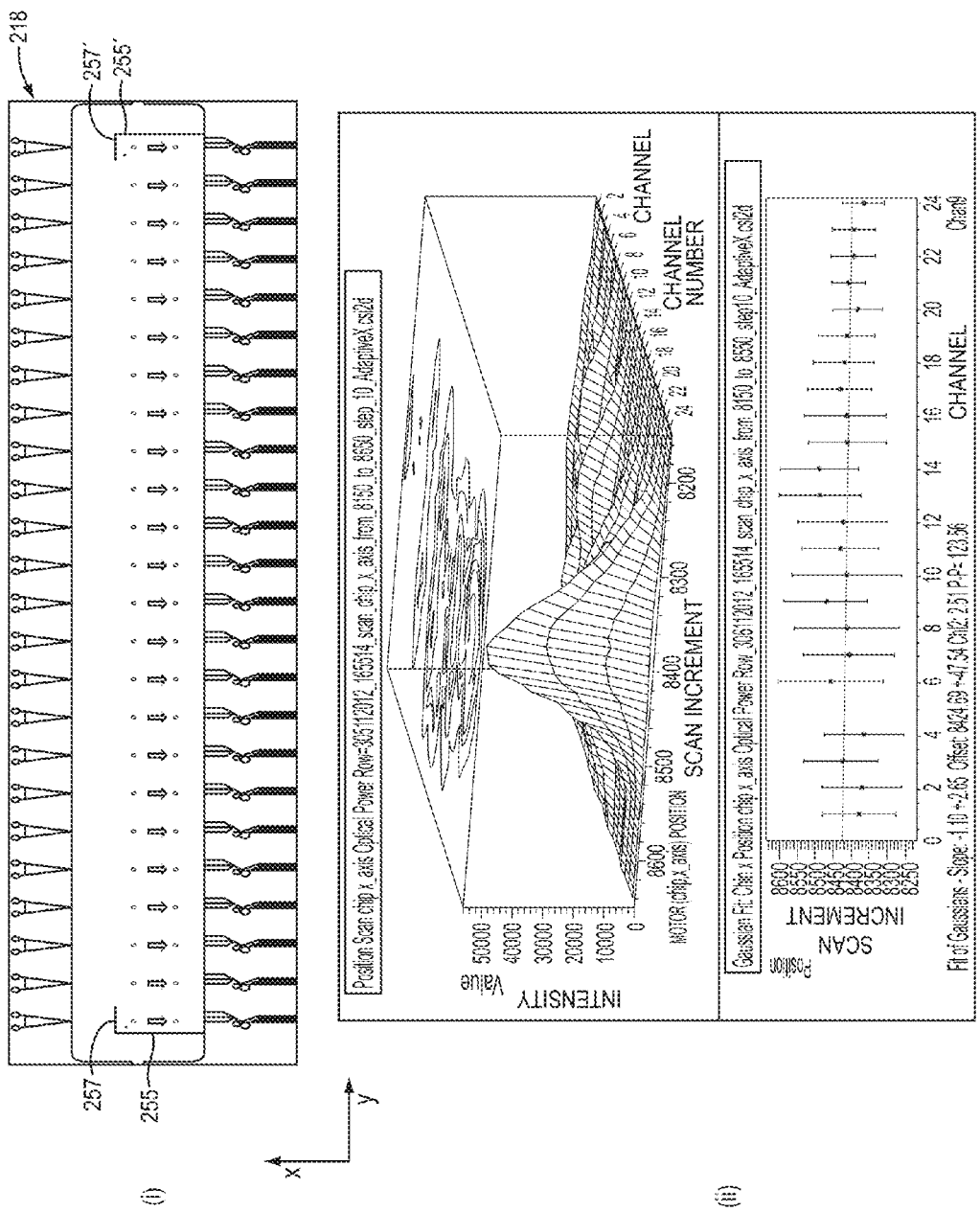

FIG. 21 illustrates a fine scanning process wherein: (i) the microfluidic chip 218 is moved in the x-direction to detect a signal emanating from the second pinholes; and (ii) data is collected, plotted and analyzed to determine a fine X position value ($X_{align}$). In the three-dimensional graph, data is presented as signal intensity for each of the middle pinholes associated with a microfluidic channel and for each x-direction scanning increment or position. In this graph, the incremental scanning step in the x-direction is 10 microns. In the lower two-dimensional graph, the peak signal intensity and the signal intensity spread for each second pinhole are plotted for each of the microfluidic channels.

Figure 22:
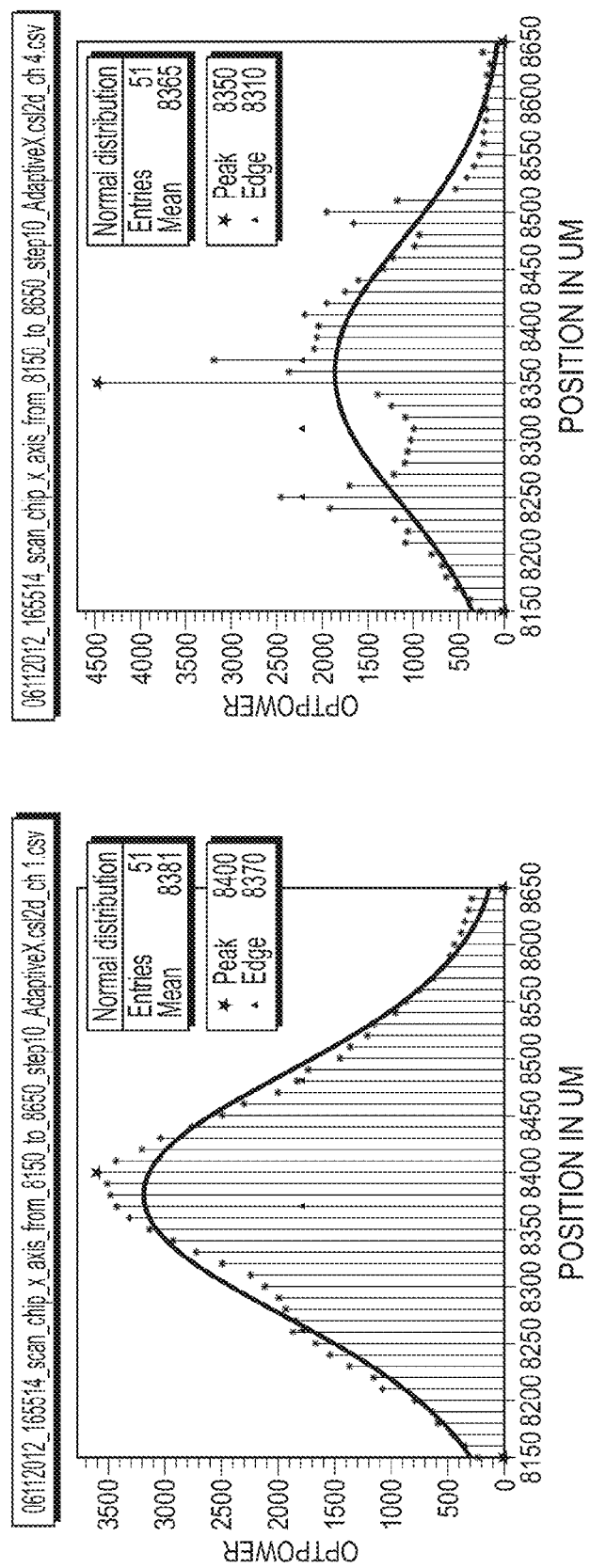

Generally, an excitation source has a Gaussian profile. It may be desirable to find the edge of the profile and/or the peak value. As shown in FIG. 22, a Gaussian fit of the pinhole intensity signal may be used to determined peak and edge values for each pinhole. FIG. 22(i) shows the optical power data for the second pinhole for the first microfluidic channel; FIG. 22(ii) shows the optical power data for the second pinhole for the fourth microfluidic channel.

Figure 23:
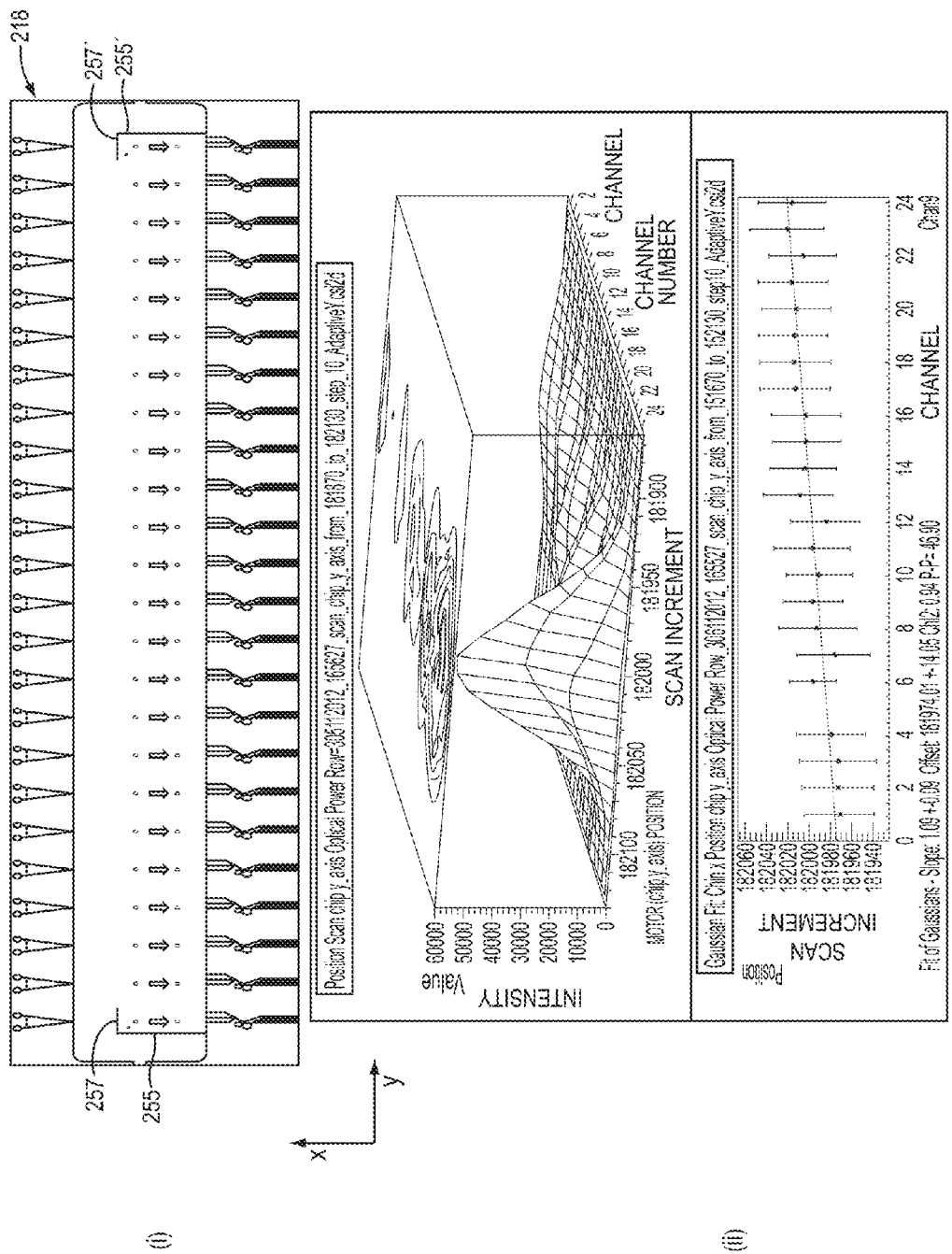

FIG. 23 illustrates a fine scanning process wherein: (i) the microfluidic chip 218 is moved in the y-direction to detect a signal emanating from the second pinholes; and (ii) data is collected, plotted and analyzed to determine a fine Y position value ($Y_{align}$). In the three-dimensional graph, data is presented as signal intensity for each of the middle pinholes associated with a microfluidic channel and for each y-direction scanning increment or position. In this graph, the incremental scanning step in the y-direction is 10 microns. In the lower two-dimensional graph, the peak signal intensity and the signal intensity spread for each second pinhole are plotted for each of the microfluidic channels. Again, a Gaussian fit of the pinhole intensity signal may be used to determined peak and edge values for each pinhole.

Figure 24:
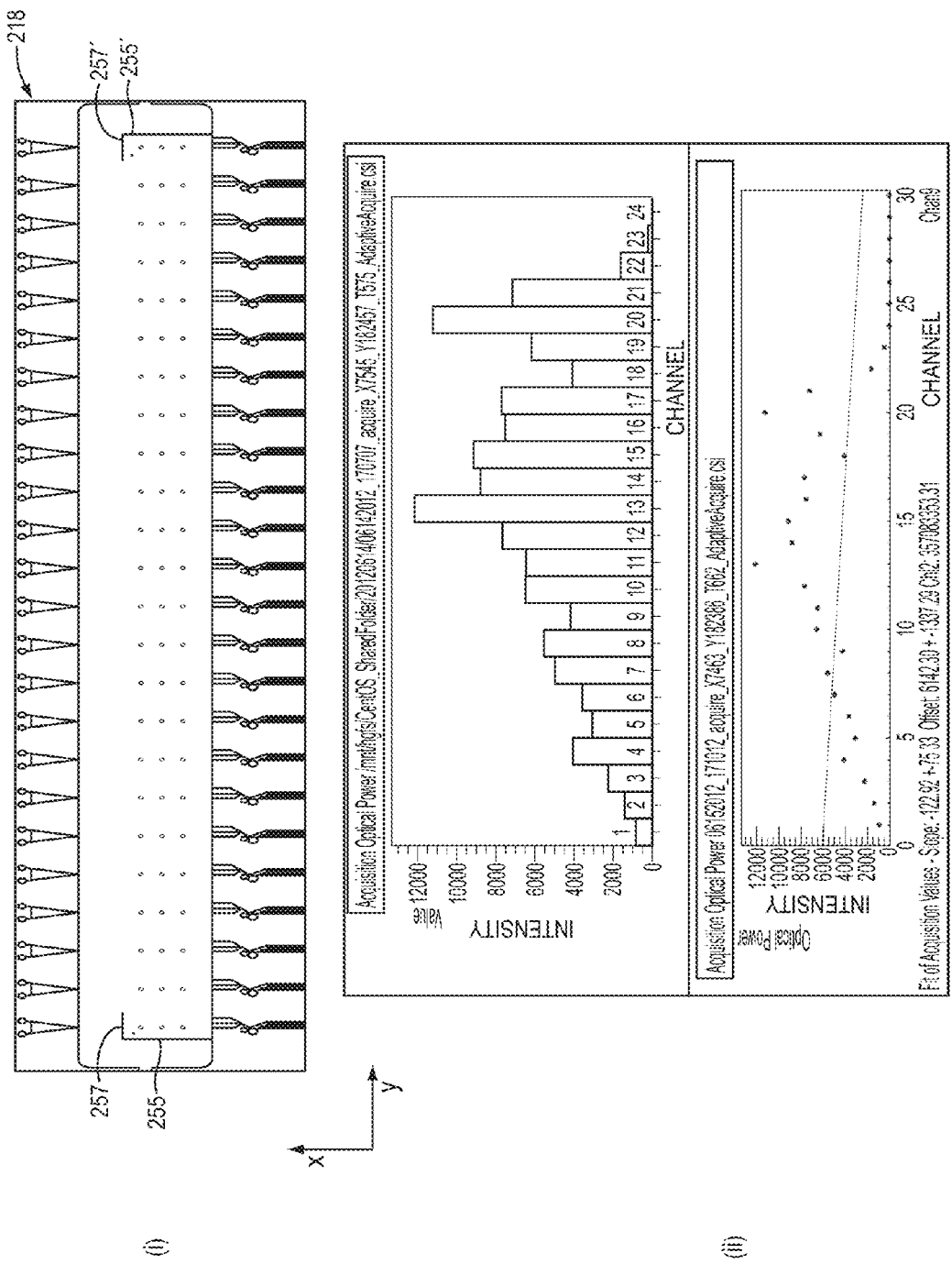

FIG. 24 illustrates that the microfluidic chip 218 is moved through its fine $X_{align}$ and $Y_{align}$ positioning values to its final aligned position. Each microfluidic channel is thus automatically properly aligned with the electromagnetic radiation source so that particle processing data may be acquired. Data may be acquired to verify the alignment.

According to certain embodiments, all fine scanning steps may use a Gaussian fit to determine the fine $X_{align}$ and/or $Y_{align}$ position values. As a non-limiting example, the fine scan increment may be 10 microns and the Gaussian fit may be of subset precision.

It is to be understood that for any of the processes described above, one or more of the steps and/or sub-steps delineated above may be eliminated, that the steps and/or sub-steps need not necessarily be performed in the order presented above, that one or more step, sub-steps and/or blocks of steps and/or sub-steps may be repeated; and/or additional and/or other steps and/or sub-steps may be interposed.

Although the systems, assemblies and methods of the present disclosure have been described with reference to exemplary embodiments thereof, the present disclosure is not limited to such exemplary embodiments and/or implementations. For example, certain aspects that have been described with respect to system 100 may be equally applicable to system 200 (and vice versa). Indeed, the systems, assemblies and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A method for automatically operating a particle processing system in an operatorless fashion during a particle processing operation, the method comprising:
   providing a stream of particles from a particle delivery assembly to a particle processing assembly, the particle processing assembly including a particle detection region and a particle processing region;
   driving the stream at an input oscillation frequency, amplitude, and phase to form droplets;
   generating a first image of the stream during the particle processing operation;
   determining, during the particle processing operation, a first value for a physical dimension of the stream from the first image;
   determining, during the particle processing operation, a first value of an operational characteristic of the stream based on the first determined value of the physical dimension of the stream, wherein the operational characteristic is selected from one of a drop delay time and a droplet break-off point;
   determining if the operational characteristic meets a predetermined criteria; and
   automatically adjusting, during the particle processing operation, an operational parameter associated with the particle delivery assembly, wherein the operational parameter is selected from at least one of the input oscillation frequency, amplitude, and phase, in response to determining that the operational characteristic does not meet the predetermined criteria.

2. The method of claim 1, further comprising:
   directing a radiation source from a signal source assembly into the particle processing assembly to interrogate the particles;
   receiving a signal at a signal detector assembly from the particle processing assembly; and
   collecting the particles from the particle processing assembly in a particle collection assembly.

3. The method of claim 1, further comprising:
   generating a second image of the droplet stream;
   determining a second value for the physical dimension of the stream from the second image;
   determining, during the particle processing operation, a second value of the operational characteristic of the stream based on the second determined value of the physical dimension of the stream;
   determining, during the particle processing operation, a difference between the first value of the operational characteristic and the second value of the operational characteristic; and
   setting the predetermined criteria equal to this difference.

4. The method of claim 1, wherein the particle processing assembly is provided as a microfluidic assembly having at least one microfluidic channel.

5. The method of claim 1, wherein the step of automatically adjusting includes a remote processor remotely controlling one or more of the operational parameters of the particle delivery assembly.

6. The method of claim 1, wherein the at least one operational characteristic includes a drop delay, the method further comprising automatically determining the drop delay during the particle processing operation by:
   driving the stream of particles at an input oscillation frequency and amplitude to form droplets;
   generating at least one image of the droplet stream between the particle detection region and a droplet break-off point;
   determining an undulation length of the stream;
   calculating a drop delay time for the stream to travel from the particle detection region to the droplet break-off point based on the undulation length of the stream and a distance between the particle detection region and the break-off point; and
   providing the calculated drop delay time to a controller of a charging device.

7. The method of claim 6, further comprising:
   determining the distance between the detection region and the break-off point based on a determination of the location of the break-off point during the particle processing operation.

8. The method of claim 6, further comprising:
comparing the automatically determined drop delay to one of a previously automatically determined drop delay and a predetermined drop delay value; and
providing an input to a controller of a droplet generator to control the input oscillation frequency, amplitude or phase based on the automatically determined drop delay.

9. The method of claim 1, wherein the at least one operational characteristic includes a droplet break-off point and wherein the first image of the stream encompasses the droplet break-off point, the method further comprising automatically determining the longitudinal position of the droplet break-off point by:
determining a first longitudinal zero-width stream location based on the first image signal where the width of the stream first goes to zero;
generating a second image of the stream that encompasses the droplet break-off point;
determining a second longitudinal zero-width stream location based on the second image signal where the width of the stream first goes to zero;
determining a difference between the first and second longitudinal zero-width stream locations; and
automatically adjusting the input oscillation phase if the difference between the first and second longitudinal zero-width stream locations exceeds a predetermined threshold criteria.

10. The method of claim 9, further comprising:
determining, based on the first image, where the width of the stream first achieves a local minimum above the first longitudinal zero-width stream location and determining a first local-minimum stream width at that local minimum location;
determining, based on the second image, where the width of the stream first achieves a local minimum above the second longitudinal zero-width stream location and determining a second local-minimum stream width at that local minimum location;
determining a difference between the first and second local-minimum stream widths; and
automatically adjusting the input oscillation amplitude if the difference between the first and second local-minimum stream widths exceeds a predetermined threshold criteria.

11. The method of claim 9, further comprising:
synchronizing the generation of the first and second images with the input oscillation frequency.

* * * * *